(12) United States Patent
De Kimpe et al.

(10) Patent No.: US 11,427,820 B2
(45) Date of Patent: Aug. 30, 2022

(54) METHODS AND MEANS FOR EFFICIENT SKIPPING OF EXON 45 IN DUCHENNE MUSCULAR DYSTROPHY PRE-MRNA

(71) Applicants: BioMarin Technologies B.V., Leiden (NL); Academisch Ziekenhuis Leiden, Leiden (NL)

(72) Inventors: Josephus Johannes De Kimpe, Utrecht (NL); Adriana Marie Rus, Hoofddorp (NL); Gerard Johannes Platenburg, Voorschoten (NL); Judith Christina Theodora Van Deutekom, Dordrecht (NL); Garrit-Jan Boudewijn Van Ommen, Amsterdam (NL)

(73) Assignees: BioMarin Technologies B.V., Leiden (NL); Academisch Ziekenbuls Leiden, Leiden (NL)

( * ) Notice: Subject to any disclaimer, the term of this patent is extended or adjusted under 35 U.S.C. 154(b) by 0 days.

(21) Appl. No.: 16/584,115

(22) Filed: Sep. 26, 2019

(65) Prior Publication Data
US 2020/0239886 A1    Jul. 30, 2020

Related U.S. Application Data

(63) Continuation of application No. 16/283,458, filed on Feb. 22, 2019, now abandoned, and a continuation of application No. 16/229,821, filed on Dec. 21, 2018, now abandoned, which is a continuation of application No. 15/390,836, filed on Dec. 27, 2016, now abandoned, which is a continuation of application No. 14/542,183, filed on Nov. 14, 2014, now Pat. No. 9,528,109, which is a continuation of application No. 14/200,251, filed on Mar. 7, 2014, now abandoned, which is a continuation of application No. 14/134,971, filed on Dec. 19, 2013, now abandoned, which is a continuation of application No. 14/097,210, filed on Dec. 4, 2013, now abandoned, which is a continuation of application No. 13/094,548, filed on Apr. 26, 2011, now Pat. No. 9,926,557, which is a continuation of application No. PCT/NL2009/005006, filed on Jan. 13, 2009, which is a continuation-in-part of application No. PCT/NL2008/050673, filed on Oct. 27, 2008, application No. 16/584,115, which is a continuation of application No. 16/229,534, filed on Dec. 21, 2018, now abandoned, which is a continuation of application No. 15/908,836, filed on Dec. 27, 2016, now abandoned, which is a
(Continued)

(51) Int. Cl.
| | |
|---|---|
| C12N 15/11 | (2006.01) |
| C12N 15/113 | (2010.01) |
| A61K 31/56 | (2006.01) |
| A61K 31/57 | (2006.01) |
| A61K 38/17 | (2006.01) |
| A61K 31/7088 | (2006.01) |
| A61K 45/06 | (2006.01) |
| A61K 31/573 | (2006.01) |
| A61K 31/58 | (2006.01) |
| A61K 48/00 | (2006.01) |

(52) U.S. Cl.
CPC ............ *C12N 15/113* (2013.01); *A61K 31/56* (2013.01); *A61K 31/57* (2013.01); *A61K 31/573* (2013.01); *A61K 31/58* (2013.01); *A61K 31/7088* (2013.01); *A61K 38/1719* (2013.01); *A61K 45/06* (2013.01); *A61K 48/00* (2013.01); *C12N 2310/11* (2013.01); *C12N 2310/111* (2013.01); *C12N 2310/31* (2013.01); *C12N 2310/313* (2013.01); *C12N 2310/314* (2013.01); *C12N 2310/315* (2013.01); *C12N 2310/3181* (2013.01); *C12N 2310/321* (2013.01); *C12N 2310/3231* (2013.01); *C12N 2310/3233* (2013.01); *C12N 2310/346* (2013.01); *C12N 2320/31* (2013.01); *C12N 2320/33* (2013.01)

(58) Field of Classification Search
CPC . C12N 15/111; C12N 15/113; C12N 2310/11; C12N 2310/321; C12N 2320/33
See application file for complete search history.

(56) References Cited

U.S. PATENT DOCUMENTS

| | | |
|---|---|---|
| 5,034,506 A | 7/1991 | Summerton et al. |
| 5,418,139 A | 5/1995 | Campbell |

(Continued)

FOREIGN PATENT DOCUMENTS

| | | |
|---|---|---|
| CA | 2319149 A1 | 10/2001 |
| CA | 2526893 A1 | 11/2004 |

(Continued)

OTHER PUBLICATIONS

Aartsma-Rus, A., et al., "Antisense Mediated Exon Skipping; A Versatile Tool with Therapeutic and Research Applications," RNA, vol. 13 (10), pp. 1609-1624, 2007.
(Continued)

*Primary Examiner* — Dana H Shin
(74) *Attorney, Agent, or Firm* — Rimon, P.C.; Dale L. Rieger

(57) ABSTRACT

The. invention relates to a method for inducing or promoting skipping of exon 45 of DMD pre-mRNA in a Duchenne Muscular Dystrophy patient, preferably in an isolated (muscle) cell, the method comprising providing said cell with an antisense molecule that binds to a continuous stretch of at least 21 nucleotides within said exon. The invention further relates to such antisense molecule used in said method.

Figure 1:
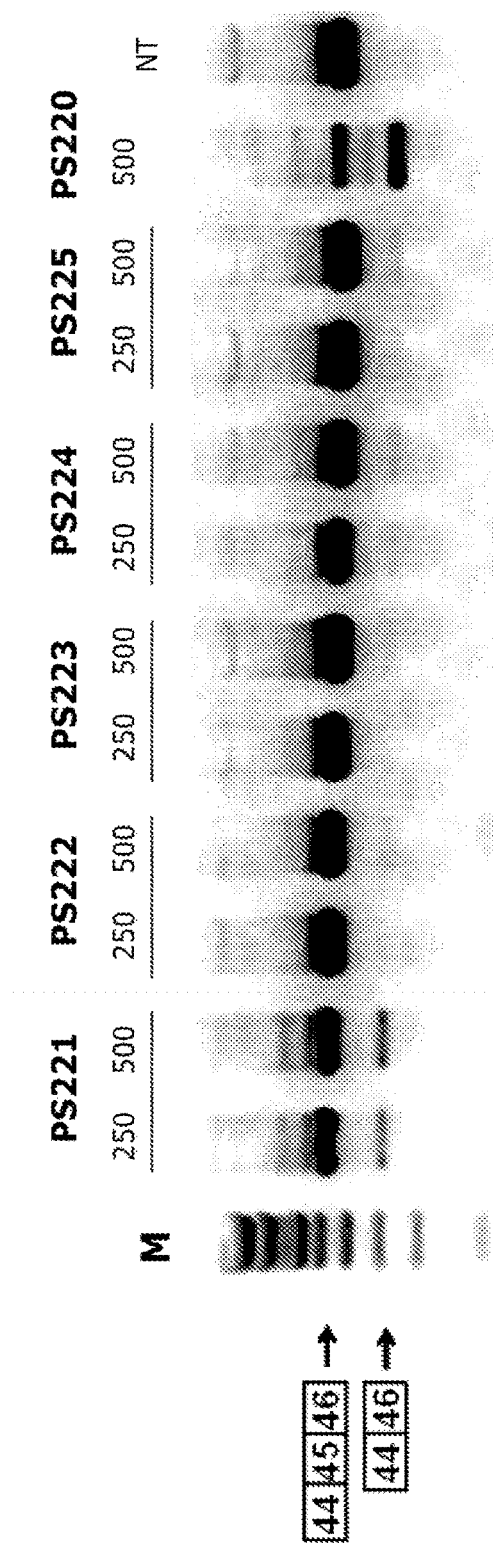

10 Claims, 2 Drawing Sheets
Specification includes a Sequence Listing.

Related U.S. Application Data continuation of application No. 14/542,183, filed on Nov. 14, 2014, now Pat. No. 9,528,109, which is a continuation of application No. 14/200,251, filed on Mar. 7, 2014, now abandoned, which is a continuation of application No. 14/134,971, filed on Dec. 19, 2013, now abandoned, which is a continuation of application No. 14/097,210, filed on Dec. 4, 2013, now abandoned, which is a continuation of application No. 13/094,548, filed on Apr. 26, 2011, now Pat. No. 9,926,557, which is a continuation of application No. PCT/NL2009/050006, filed on Jan. 13, 2009, which is a continuation-in-part of application No. PCT/NL2008/050673, filed on Oct. 27, 2008.

(56) References Cited

U.S. PATENT DOCUMENTS

| | | |
|---|---|---|
| 5,541,308 A | 7/1996 | Hogan et al. |
| 5,593,974 A | 1/1997 | Rosenberg et al. |
| 5,608,046 A | 3/1997 | Cook et al. |
| 5,624,803 A | 4/1997 | Noonberg et al. |
| 5,627,263 A | 5/1997 | Ruoslahti et al. |
| 5,658,764 A | 8/1997 | Pergolizzi et al. |
| 5,741,645 A | 4/1998 | Orr et al. |
| 5,766,847 A | 6/1998 | Jaeckle et al. |
| 5,853,995 A | 12/1998 | Lee |
| 5,869,252 A | 2/1999 | Bouma et al. |
| 5,916,808 A | 6/1999 | Kole et al. |
| 5,962,332 A | 10/1999 | Singer et al. |
| 5,968,909 A | 10/1999 | Agrawal et al. |
| 5,976,879 A | 11/1999 | Kole et al. |
| 6,124,100 A | 9/2000 | Jin |
| 6,130,207 A | 10/2000 | Dean et al. |
| 6,133,031 A | 10/2000 | Monia et al. |
| 6,165,786 A | 12/2000 | Bennet et al. |
| 6,172,208 B1 | 1/2001 | Cook |
| 6,172,216 B1 | 1/2001 | Bennett et al. |
| 6,210,892 B1 | 4/2001 | Bennett et al. |
| 6,251,589 B1 | 6/2001 | Tsuji et al. |
| 6,280,938 B1 | 8/2001 | Ranum et al. |
| 6,300,060 B1 | 10/2001 | Kantoff et al. |
| 6,322,978 B1 | 11/2001 | Kahn et al. |
| 6,329,501 B1 | 12/2001 | Smith et al. |
| 6,355,481 B1 | 3/2002 | Li et al. |
| 6,355,690 B1 | 3/2002 | Tsuji |
| 6,369,038 B1 | 4/2002 | Blumenfeld et al. |
| 6,379,698 B1 | 4/2002 | Leamon |
| 6,399,575 B1 | 6/2002 | Smith et al. |
| 6,514,755 B1 | 2/2003 | Ranum et al. |
| 6,623,927 B1 | 9/2003 | Brahmachari et al. |
| 6,653,466 B2 | 11/2003 | Matsuo |
| 6,653,467 B1 | 11/2003 | Matsuo et al. |
| 6,670,461 B1 | 12/2003 | Wengel et al. |
| 6,727,355 B2 | 4/2004 | Matsuo et al. |
| 6,794,192 B2 | 9/2004 | Parums et al. |
| 6,875,736 B2 | 4/2005 | Rana |
| 6,902,896 B2 | 6/2005 | Ranum et al. |
| 6,982,150 B2 | 1/2006 | Sheetz et al. |
| 7,001,994 B2 | 2/2006 | Zhu |
| 7,034,009 B2 | 4/2006 | Pavco et al. |
| 7,118,893 B2 | 10/2006 | Ranum et al. |
| 7,189,530 B2 | 3/2007 | Botstein et al. |
| 7,202,210 B2 | 4/2007 | Wolfman et al. |
| 7,250,404 B2 | 7/2007 | Feigner et al. |
| 7,320,965 B2 | 1/2008 | Sah et al. |
| 7,355,018 B2 | 4/2008 | Glass |
| 7,405,193 B2 | 7/2008 | Lodish et al. |
| 7,442,782 B2 | 10/2008 | Ranum et al. |
| 7,514,551 B2 | 4/2009 | Rabbani et al. |
| 7,534,879 B2 | 5/2009 | Van Deutekom |
| 7,589,189 B2 | 9/2009 | Ichiro et al. |
| 7,655,785 B1 | 2/2010 | Bentwich |
| 7,742,782 B2 | 6/2010 | Kim et al. |
| 7,771,727 B2 | 8/2010 | Fuselier et al. |
| 7,807,816 B2 | 10/2010 | Wilson et al. |
| 7,902,160 B2 | 3/2011 | Matsuo et al. |
| 7,960,541 B2 | 6/2011 | Wilton et al. |
| 7,973,015 B2 | 7/2011 | Van Ommen et al. |
| 8,084,601 B2 | 12/2011 | Popplewell et al. |
| 8,232,384 B2 | 7/2012 | Wilton et al. |
| 8,263,760 B2 | 9/2012 | De Kimpe et al. |
| 8,268,962 B2 | 9/2012 | Heemskerk et al. |
| 8,304,398 B2 | 11/2012 | 'T Hoen et al. |
| 8,324,371 B2 | 12/2012 | Popplewell et al. |
| 8,361,979 B2 | 1/2013 | Aartsma-Rus et al. |
| 8,450,474 B2 | 5/2013 | Wilton et al. |
| 8,455,634 B2 | 6/2013 | Wilton et al. |
| 8,455,635 B2 | 6/2013 | Wilton et al. |
| 8,455,636 B2 | 6/2013 | Wilton et al. |
| 8,476,423 B2 | 7/2013 | Wilton et al. |
| 8,486,907 B2 | 7/2013 | Wilton et al. |
| 8,519,097 B2 | 8/2013 | Heemskerk et al. |
| 8,524,880 B2 | 9/2013 | Wilton et al. |
| 8,609,065 B2 | 12/2013 | Kuik-Romeijn et al. |
| 8,637,483 B2 | 1/2014 | Wilton et al. |
| 8,759,507 B2 | 6/2014 | Van Deutekom et al. |
| 8,802,645 B2 | 8/2014 | Van Ommen et al. |
| 8,865,883 B2 | 10/2014 | Sazani et al. |
| 9,057,066 B2 | 6/2015 | Hung et al. |
| 9,079,934 B2 | 7/2015 | Watanabe et al. |
| 9,139,828 B2 | 9/2015 | Platenburg et al. |
| 9,243,026 B2 | 1/2016 | Matsuo et al. |
| 9,243,245 B2 | 1/2016 | De Kimpe et al. |
| 9,499,818 B2 | 11/2016 | Van Deutekom et al. |
| 9,528,109 B2 | 12/2016 | De Kimpe et al. |
| 2001/0056077 A1 | 12/2001 | Matsuo |
| 2002/0049173 A1 | 4/2002 | Bennett et al. |
| 2002/0055481 A1 | 5/2002 | Matsuo et al. |
| 2002/0109476 A1 | 8/2002 | Kim |
| 2002/0115824 A1 | 8/2002 | Engler et al. |
| 2002/0165150 A1 | 11/2002 | Ben-Sasson |
| 2003/0045488 A1 | 3/2003 | Brown et al. |
| 2003/0073215 A1 | 4/2003 | Baker et al. |
| 2003/0082763 A1 | 5/2003 | Baker et al. |
| 2003/0082766 A1 | 5/2003 | Baker et al. |
| 2003/0109476 A1 | 6/2003 | Kmiec et al. |
| 2003/0124523 A1 | 7/2003 | Asselbergs et al. |
| 2003/0130224 A1 | 7/2003 | Monahan et al. |
| 2003/0134790 A1 | 7/2003 | Langenfeld |
| 2003/0175389 A1 | 9/2003 | Shaposhnikov |
| 2003/0235845 A1 | 12/2003 | Van Ommen et al. |
| 2003/0236214 A1 | 12/2003 | Wolff et al. |
| 2004/0101852 A1 | 5/2004 | Bennett et al. |
| 2004/0132684 A1 | 7/2004 | Sampath et al. |
| 2004/0219565 A1 | 11/2004 | Kauppinen et al. |
| 2004/0226056 A1 | 11/2004 | Roch et al. |
| 2005/0048495 A1 | 3/2005 | Baker et al. |
| 2005/0096284 A1 | 5/2005 | McSwiggen |
| 2005/0222009 A1 | 10/2005 | Lamensdorf et al. |
| 2005/0246794 A1 | 11/2005 | Khvorova et al. |
| 2005/0277133 A1 | 12/2005 | McSwiggen |
| 2005/0288246 A1 | 12/2005 | Iversen et al. |
| 2006/0003322 A1* | 1/2006 | Bentwich ............ C12N 15/113 435/6.16 |
| 2006/0024715 A1 | 2/2006 | Liu et al. |
| 2006/0074034 A1 | 4/2006 | Collins et al. |
| 2006/0099612 A1 | 5/2006 | Nakao et al. |
| 2006/0099616 A1 | 5/2006 | Van Ommen et al. |
| 2006/0147952 A1 | 7/2006 | Van Ommen et al. |
| 2006/0148740 A1 | 7/2006 | Platenburg |
| 2006/0160121 A1 | 7/2006 | Mounts et al. |
| 2007/0021360 A1 | 1/2007 | Nyce et al. |
| 2007/0082861 A1 | 4/2007 | Matsuo et al. |
| 2007/0134655 A1 | 6/2007 | Bentwich |
| 2007/0141628 A1 | 6/2007 | Cunningham et al. |
| 2007/0275914 A1 | 11/2007 | Manoharan et al. |
| 2007/0292408 A1 | 12/2007 | Singh et al. |
| 2007/0299027 A1 | 12/2007 | Hung et al. |
| 2008/0015158 A1 | 1/2008 | Ahmed et al. |
| 2008/0015185 A1 | 1/2008 | Ahmed et al. |
| 2008/0039418 A1 | 2/2008 | Freier |
| 2008/0113351 A1 | 5/2008 | Naito et al. |

(56) References Cited

U.S. PATENT DOCUMENTS

| | | |
|---|---|---|
| 2008/0200409 A1 | 8/2008 | Wilson et al. |
| 2008/0207538 A1 | 8/2008 | Lawrence et al. |
| 2008/0209581 A1 | 8/2008 | Van Ommen et al. |
| 2008/0249294 A1 | 10/2008 | Haeberli et al. |
| 2009/0092981 A1 | 4/2009 | Swayze et al. |
| 2009/0099066 A1 | 4/2009 | Moulton et al. |
| 2009/0228998 A1 | 9/2009 | Van Ommen et al. |
| 2009/0269755 A1* | 10/2009 | Aartsma-Rus .......... A61P 35/00 435/6.11 |
| 2009/0312532 A1 | 12/2009 | Van Deutekom |
| 2010/0081627 A1 | 4/2010 | Sampath et al. |
| 2010/0099750 A1 | 4/2010 | McSwiggen et al. |
| 2010/0130591 A1 | 5/2010 | Sanzi et al. |
| 2010/0168212 A1 | 7/2010 | Popplewell et al. |
| 2010/0184833 A1 | 7/2010 | De Kimpe et al. |
| 2010/0216238 A1 | 8/2010 | Baker et al. |
| 2010/0248239 A1 | 9/2010 | Highsmith et al. |
| 2010/0286235 A1 | 11/2010 | Renzi et al. |
| 2011/0015253 A1 | 1/2011 | Wilton et al. |
| 2011/0015258 A1 | 1/2011 | Wilton et al. |
| 2011/0046203 A1 | 2/2011 | Wilton et al. |
| 2011/0054005 A1 | 3/2011 | Naito et al. |
| 2011/0166081 A1 | 7/2011 | Campbell et al. |
| 2011/0184050 A1 | 7/2011 | De Kimpe et al. |
| 2011/0263682 A1 | 10/2011 | De Kimpe et al. |
| 2011/0263686 A1 | 10/2011 | Wilton et al. |
| 2011/0294753 A1 | 12/2011 | De Kimpe et al. |
| 2012/0022134 A1 | 1/2012 | De Kimpe et al. |
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0046342 A1 | 2/2012 | Van Deutekom et al. |
| 2012/0046348 A1 | 2/2012 | Valiant et al. |
| 2012/0108652 A1 | 5/2012 | Popplewell et al. |
| 2012/0122801 A1 | 5/2012 | Platenburg |
| 2012/0202752 A1 | 8/2012 | Lu |
| 2012/0270925 A1 | 10/2012 | Wilton et al. |
| 2013/0072671 A1 | 3/2013 | Van Deutekom |
| 2013/0116310 A1 | 5/2013 | Wilton et al. |
| 2013/0211062 A1 | 8/2013 | Watanabe et al. |
| 2013/0217755 A1 | 8/2013 | Wilton et al. |
| 2013/0253033 A1 | 9/2013 | Wilton et al. |
| 2013/0253180 A1 | 9/2013 | Wilton et al. |
| 2013/0274313 A1 | 10/2013 | Wilton et al. |
| 2013/0302806 A1 | 11/2013 | Van Deutekom |
| 2013/0331438 A1 | 12/2013 | Wilton et al. |
| 2014/0045763 A1 | 2/2014 | Aguilera Diez et al. |
| 2014/0113955 A1 | 4/2014 | De Kimpe et al. |
| 2014/0128592 A1 | 5/2014 | De Kimpe et al. |
| 2014/0213635 A1 | 7/2014 | Van Deutekom |
| 2014/0221458 A1 | 8/2014 | De Kimpe et al. |
| 2014/0275212 A1 | 9/2014 | Van Deutekom |
| 2014/0298496 A1 | 10/2014 | Krainer et al. |
| 2014/0343266 A1 | 11/2014 | Watanabe et al. |
| 2014/0350076 A1 | 11/2014 | Van Deutekom |
| 2014/0357698 A1 | 12/2014 | Van Deutekom et al. |
| 2014/0357855 A1 | 12/2014 | Van Deutekom et al. |
| 2014/0378527 A1 | 12/2014 | Van Deutekom et al. |
| 2015/0045413 A1 | 2/2015 | De Visser et al. |
| 2015/0080563 A2 | 3/2015 | Van Deutekom et al. |
| 2015/0148404 A1 | 5/2015 | De Visser et al. |
| 2015/0191725 A1 | 7/2015 | Van Deutekom |
| 2015/0203849 A1 | 7/2015 | Van Deutekom et al. |
| 2015/0218559 A1 | 8/2015 | Van Deutekom et al. |
| 2015/0322434 A1 | 11/2015 | Van Deutekom et al. |
| 2015/0361424 A1 | 12/2015 | Van Deutekom |
| 2016/0040161 A1 | 2/2016 | Packard et al. |
| 2016/0053254 A1 | 2/2016 | De Kimpe et al. |
| 2016/0053262 A1 | 2/2016 | Platenburg et al. |
| 2016/0168570 A1 | 6/2016 | Van Deutekom et al. |
| 2016/0194636 A1 | 7/2016 | Van Deutekom et al. |
| 2016/0251658 A1 | 9/2016 | Van Deutekom et al. |
| 2016/0264967 A1 | 9/2016 | Van Deutekom et al. |
| 2016/0304864 A1 | 10/2016 | De Kimpe et al. |
| 2016/0355810 A1 | 12/2016 | Van Deutekom et al. |
| 2017/0029818 A1 | 2/2017 | De Visser et al. |
| 2017/0029820 A1 | 2/2017 | Aguilera Diez et al. |
| 2017/0044534 A1 | 2/2017 | Van Deutekom |
| 2017/0107512 A1 | 4/2017 | De Kimpe et al. |

FOREIGN PATENT DOCUMENTS

| | | |
|---|---|---|
| CN | 101501193 A | 8/2009 |
| EP | 0438512 A1 | 7/1991 |
| EP | 0558697 A1 | 9/1993 |
| EP | 0614977 A2 | 9/1994 |
| EP | 0438512 B1 | 12/1997 |
| EP | 0850300 A1 | 7/1998 |
| EP | 1015628 A1 | 7/2000 |
| EP | 1054058 A1 | 11/2000 |
| EP | 1133993 A1 | 9/2001 |
| EP | 1160318 A2 | 12/2001 |
| EP | 1191097 A1 | 3/2002 |
| EP | 1191098 A2 | 3/2002 |
| EP | 1380644 A1 | 1/2004 |
| EP | 1487493 A2 | 12/2004 |
| EP | 1495769 A1 | 1/2005 |
| EP | 1501931 A2 | 2/2005 |
| EP | 1544297 A2 | 6/2005 |
| EP | 1567667 A1 | 8/2005 |
| EP | 1568769 A1 | 8/2005 |
| EP | 1619249 A1 | 1/2006 |
| EP | 1191098 B9 | 6/2006 |
| EP | 1857548 A1 | 11/2007 |
| EP | 2119783 A1 | 11/2009 |
| EP | 2135948 A2 | 12/2009 |
| EP | 2344637 B1 | 12/2014 |
| JP | 2002-325582 A | 11/2002 |
| KR | 20030035047 A | 5/2003 |
| WO | WO-9301286 A2 | 1/1993 |
| WO | WO-9428175 A1 | 12/1994 |
| WO | 95/16718 A1 | 6/1995 |
| WO | WO-9516718 A1 | 6/1995 |
| WO | WO-9521184 A1 | 8/1995 |
| WO | WO-9530774 A1 | 11/1995 |
| WO | WO-9712899 A1 | 4/1997 |
| WO | WO-9730067 A1 | 8/1997 |
| WO | WO-9818920 A1 | 5/1998 |
| WO | WO-9843993 A2 | 10/1998 |
| WO | WO-9849345 A1 | 11/1998 |
| WO | WO-9853804 A1 | 12/1998 |
| WO | WO-9916871 A2 | 4/1999 |
| WO | WO-9955857 A2 | 11/1999 |
| WO | WO-9963975 A2 | 12/1999 |
| WO | WO-0024885 A2 | 5/2000 |
| WO | WO-0076554 A1 | 12/2000 |
| WO | WO-0116312 A2 | 3/2001 |
| WO | 01/32832 A2 | 5/2001 |
| WO | WO-0159102 A2 | 8/2001 |
| WO | WO-0179283 A1 | 10/2001 |
| WO | WO-0183503 A2 | 11/2001 |
| WO | WO-0183695 A2 | 11/2001 |
| WO | WO-0224906 A1 | 3/2002 |
| WO | WO-0226812 A1 | 4/2002 |
| WO | WO-0229006 A2 | 4/2002 |
| WO | WO-0229056 A2 | 4/2002 |
| WO | WO-03002739 A1 | 1/2003 |
| WO | WO-03004511 A2 | 1/2003 |
| WO | WO-03013437 A2 | 2/2003 |
| WO | WO-03014145 A2 | 2/2003 |
| WO | WO-03037172 A2 | 5/2003 |
| WO | WO-03062258 A1 | 7/2003 |
| WO | WO-03095647 A2 | 11/2003 |
| WO | WO-2004011060 A2 | 2/2004 |
| WO | WO-2004015106 A1 | 2/2004 |
| WO | WO-2004016787 A1 | 2/2004 |
| WO | WO-2004037854 A1 | 5/2004 |
| WO | 2004/047741 A2 | 6/2004 |
| WO | WO-2004047741 A2 | 6/2004 |
| WO | WO-2004048570 A1 | 6/2004 |

(56) References Cited

FOREIGN PATENT DOCUMENTS

| | | |
|---|---|---|
| WO | WO-2004083432 A1 | 9/2004 |
| WO | WO-2004083446 A2 | 9/2004 |
| WO | WO-2004101787 A1 | 11/2004 |
| WO | WO-2004108157 A2 | 12/2004 |
| WO | 2005/021727 A2 | 3/2005 |
| WO | WO-2005019453 A2 | 3/2005 |
| WO | WO-2005023836 A2 | 3/2005 |
| WO | 2005/035550 A1 | 4/2005 |
| WO | WO-2005035550 A2 | 4/2005 |
| WO | WO-2005085476 A1 | 9/2005 |
| WO | WO-2005086768 A2 | 9/2005 |
| WO | WO-2005105995 A2 | 11/2005 |
| WO | 2005/115479 A2 | 12/2005 |
| WO | WO-2005115439 A2 | 12/2005 |
| WO | WO-2005115479 A2 | 12/2005 |
| WO | WO-2005116204 A1 | 12/2005 |
| WO | WO-2006000057 A1 | 1/2006 |
| WO | WO-2006007910 A1 | 1/2006 |
| WO | WO-2006017522 A2 | 2/2006 |
| WO | WO-2006031267 A2 | 3/2006 |
| WO | WO-2006054262 A2 | 5/2006 |
| WO | WO-2006083800 A2 | 8/2006 |
| WO | WO-2006108052 A2 | 10/2006 |
| WO | WO-2006112705 A2 | 10/2006 |
| WO | WO-2006121277 A1 | 11/2006 |
| WO | WO-2006121960 A2 | 11/2006 |
| WO | WO-2007002904 A2 | 1/2007 |
| WO | WO-2007004979 A1 | 1/2007 |
| WO | 2007/018563 A2 | 2/2007 |
| WO | WO-2007044362 A2 | 4/2007 |
| WO | WO-2007089584 A2 | 8/2007 |
| WO | WO-2007089611 A2 | 8/2007 |
| WO | WO-2007123402 A2 | 11/2007 |
| WO | WO-2007135105 A1 | 11/2007 |
| WO | WO-2008011170 A2 | 1/2008 |
| WO | WO-2008018795 A1 | 2/2008 |
| WO | WO-2008021136 A2 | 2/2008 |
| WO | WO-2008039418 A2 | 4/2008 |
| WO | WO-2008043561 A2 | 4/2008 |
| WO | WO-2008103060 A1 | 8/2008 |
| WO | WO-2008103755 A1 | 8/2008 |
| WO | WO-2009005793 A2 | 1/2009 |
| WO | WO-2009008727 A2 | 1/2009 |
| WO | WO-2009015384 A1 | 1/2009 |
| WO | WO-2009054725 A2 | 4/2009 |
| WO | WO-2009099326 A1 | 8/2009 |
| WO | WO-2009101399 A1 | 8/2009 |
| WO | WO-2009120887 A2 | 10/2009 |
| WO | WO-2009135322 A1 | 11/2009 |
| WO | WO-2009139630 A2 | 11/2009 |
| WO | WO-2009144481 A2 | 12/2009 |
| WO | WO-2009151600 A2 | 12/2009 |
| WO | WO-2010001088 A1 | 1/2010 |
| WO | WO-2010006237 A2 | 1/2010 |
| WO | WO-2010014592 A1 | 2/2010 |
| WO | WO-2010044894 A1 | 4/2010 |
| WO | WO-2010048586 A1 | 4/2010 |
| WO | WO-2010050802 A2 | 5/2010 |
| WO | WO-2010110835 A1 | 9/2010 |
| WO | WO-2010115993 A1 | 10/2010 |
| WO | WO-2010123369 A1 | 10/2010 |
| WO | WO-2010144485 A1 | 12/2010 |
| WO | WO-2011032045 A1 | 3/2011 |
| WO | WO-2011057350 A1 | 5/2011 |
| WO | WO-2011078797 A2 | 6/2011 |
| WO | WO-2011097614 A1 | 8/2011 |
| WO | WO-2011097641 A1 | 8/2011 |
| WO | WO-2012012443 A2 | 1/2012 |
| WO | WO-2012021985 A1 | 2/2012 |
| WO | WO-2012029986 A1 | 3/2012 |
| WO | WO-2012109395 A1 | 8/2012 |
| WO | WO-2012150960 A1 | 11/2012 |
| WO | WO-2013082548 A1 | 6/2013 |
| WO | WO-2013082578 A1 | 6/2013 |
| WO | WO-2013100190 A1 | 7/2013 |
| WO | WO-2013120003 A1 | 8/2013 |
| WO | WO-2013170385 A1 | 11/2013 |

OTHER PUBLICATIONS

Aartsma-Rus, A., et al., "Antisense-Induced Exon Skipping for Duplications in Duchenne Muscular Dystrophy," BMC Medical Genetics, vol. 8 (43), 9 pages, 2007.

Aartsma-Rus, A., et al., "Antisense-Induced Multiexon Skipping for Duchenne Muscular Dystrophy Makes More Sense," American Journal of Human Genetics, vol. 74, pp. 83-92, 2004.

Aartsma-Rus, A., et al., "Comparative Analysis of Antisense Oligonucleotide Analogs for Targeted DMD Exon 46 Skipping in Muscle Cells," Gene Therapy, vol. 11 (18), pp. 1391-1398, 2004.

Aartsma-Rus, A., et al., "Exonic Sequences Provide Better Targets for Antisense Oligonucleotides Than Splice Site Sequences in the Modulation of Duchenne Muscular Dystrophy Splicing," Oligonucleotides, vol. 20 (2), pp. 69-77, 2010.

Aartsma-Rus, A., et al., "Exploring the Frontiers of Therapeutic Exon Skipping for Duchenne Muscular Dystrophy by Double Targeting within One or Multiple Exons," Molecular Therapy, vol. 14 (3), pp. 401-407, Sep. 2006.

Aartsma-Rus, A., et al., "Functional Analysis of 114 Exon-Internal AONs for Targeted DMD Exon Indication for Steric Hindrance of SR Protein Binding Sites," Oligonucleotides, vol. 15, pp. 284-297, 2005.

Aartsma-Rus, A., et al., "Guidelines for Antisense Oligonucleotide Design and Insight Into Splice-Modulating Mechanisms," Molecular Therapy, vol. 17 (3), pp. 548-553, Mar. 2009 (attached Supplementary Table, 7 pages).

Aartsma-Rus, A., et al., "Targeted Exon Skipping as a Potential Gene Correction Therapy for Duchenne Muscular Dystrophy," Neuromuscular Disorders, vol. 12, pp. S71-S77, 2002.

Aartsma-Rus, A., et al., "Theoretic Applicability of Antisense-Mediated Exon Skipping for Duchenne Muscular Dystrophy Mutations," Human Mutation, vol. 30 (3), pp. 293-299, 2009.

Aartsma-Rus, A., et al., "Therapeutic Antisense-Induced Exon Skipping in Cultured Muscle Cells from Six Different DMD Patients," Human Molecular Genetics, vol. 12 (8), pp. 907-914, 2003.

Aartsma-Rus, A., et al., "Therapeutic Modulation of DMD Splicing by Blocking Exonic Splicing Enhancer Sites with Antisense Oligonucleotides," Annals of the New York Academy of Sciences, vol. 1082, pp. 74-76, 2006.

Abbs, S., et al., "A Convenient Multiplex PCR System for the Detection of Dystrophin Gene Deletions: A Comparative Analysis with cDNA Hybridisation Shows Mistypings by Both Methods," Journal of Medical Genetics, vol. 28, pp. 304-311, 1991.

Academisch Ziekenhuis Leiden, "Comparative analysis of AONs for inducing the skipping of exon 45 from the dystrophin gene in human control muscle cells," 2 pages, Oct. 23, 2014.

Academisch Ziekenhuis Leiden, *Academisch Ziekenhuis Leiden v. University of Western Australia, University of Western Australia v. Academisch Ziekenhuis Leiden*, "Academisch Ziekenhuis Leiden's Response to Motion of University of Western Australia to Designate As Companion Cases to Extend the Briefing Schedules," 6 pages, Nov. 18, 2016 [Interference Nos. 106,007, 106,008, 106,013].

Academisch Ziekenhuis Leiden, Letter in Response to Article 94(3) EPC relating to EP2594641, 7 pages, Oct. 23, 2014.

Academisch Ziekenhuis Leiden, List of Exhibits (as of Apr. 3, 2015), 18 pages, Apr. 3, 2015 [Patent Interference No. 106,008 (RES)].

Academisch Ziekenhuis Leiden, List of Exhibits (as of Apr. 3, 2015), 18 pages, filed Apr. 3, 2015 [Patent Interference No. 106,007 (RES)].

Academisch Ziekenhuis Leiden, List of Exhibits (as of Feb. 17, 2015) 3 pages, Feb. 17, 2015 [Patent Interference No. 106,013 (RES)].

Academisch Ziekenhuis Leiden, List of Exhibits (as of Feb. 17, 2015), 18 pages, Feb. 17, 2015 [Patent Interference No. 106,007 (RES)].

(56) References Cited

OTHER PUBLICATIONS

Academisch Ziekenhuis Leiden, List of Exhibits (as of Feb. 17, 2015), 18 pages, Feb. 17, 2015 [Patent Interference No. 106,008 (RES)].
Academisch Ziekenhuis Leiden, List of Exhibits (as of May 5, 2015), 18 pages, filed May 5, 2015 [Patent Interference No. 106,008 (RES)].
Academisch Ziekenhuis Leiden, List of Exhibits (as of May 5, 2015) 18 pages, filed May 5, 2015 [Patent Interference No. 106,007 (RES)].
Academisch Ziekenhuis Leiden, List of Proposed Motions, 6 pages, Sep. 10, 2014 [Patent Interference No. 106,007 (RES)].
Academisch Ziekenhuis Leiden, Opposition 1 (35 U.S. C. §112(a)), 93 pages, Feb. 17, 2015 [Patent Interference No. 106,007 (RES)].
Academisch Ziekenhuis Leiden, Opposition 1 (35 U.S.C. § 112(a)), 83 pages, Feb. 17, 2015 [Patent Interference No. 106,008 (RES)].
Academisch Ziekenhuis Leiden, Opposition 1 (Standing Order ,I 203.1 and 37 C.F.R. § 41.202 (a) and (e)), 20 pages, Feb. 17, 2015 [Patent Interference No. 106,013 (RES)].
Academisch Ziekenhuis Leiden, Opposition 2 (Indefiniteness), 31 pages, Feb. 17, 2015 [Patent Interference No. 106,007 (RES)].
Academisch Ziekenhuis Leiden, Opposition 2 (Indefiniteness), 32 pages, Feb. 17, 2015 [Patent Interference No. 106,008 (RES)].
Academisch Ziekenhuis Leiden, Opposition 3 (35 U.S.C. § 135(b)), 44 pages, Feb. 17, 2015 [Patent Interference No. 106,008 (RES)].
Academisch Ziekenhuis Leiden, Opposition 3 (Standing Order 1J 203.1 and 37 C.F.R. §41.202(a) and (e)), 20 pages, Feb. 17, 2015 [Patent Interference No. 106,007 (RES)].
Academisch Ziekenhuis Leiden, Opposition 4 (To Not Exclude Evidence), 22 pages, May 5, 2015 [Patent Interference No. 106,007 (RES)].
Academisch Ziekenhuis Leiden, Patentee's letter to European Patent Office in the examination of EP 2602322, 4 pages, Dec. 9, 2013.
Academisch Ziekenhuis Leiden, Patentee's Response to Office Action to European Patent Office in the examination of EP 2602322, 6 pages, Oct. 21, 2014.
Academisch Ziekenhuis Leiden, Reply 1 (For Judgment that UWA's Claims are Unpatentable Under 35 U.S.C. §§ 102 and 103), 17 pages, Apr. 3, 2015 [Patent Interference No. 106,007 (RES)].
Academisch Ziekenhuis Leiden, Reply 2 (To Deny the Benefit of AU 2004903474), 11 pages, filed Apr. 3, 2015 [Patent Interference No. 106,007 (RES)].
Academisch Ziekenhuis Leiden, Reply 2 (To Deny the Benefit of AU 2004903474), 12 pages, Apr. 3, 2015 [Patent Interference No. 106,008 (RES)].
Academisch Ziekenhuis Leiden, Reply 3 (For Judgment of Unpatentability based on Myriad), 12 pages, Apr. 3, 2015, [Patent Interference No. 106,007 (RES)].
Academisch Ziekenhuis Leiden, Reply 3 (For Judgment of Unpatentability based on Myriad), 13 pages, Apr. 3, 2015 [Patent Interference No. 106,008 (RES)].
Academisch Ziekenhuis Leiden, Reply 4 (In Support of Responsive Motion 4 to Add Two New Claims), 17 pages, Apr. 3, 2015 [Patent Interference No. 106,007 (RES)].
Academisch Ziekenhuis Leiden, Reply Brief of Appellant Academisch Ziekenhuis Leiden, US Court of Appeals for the Federal Circuit, Case: 16/2262, 40 pages, Apr. 25, 2017.
Academisch Ziekenhuis Leiden, Request for an Opinion under Section 74(A) in relation to Patent No. EP (Uk) 16192498, 33 pages, Apr. 20, 2009.
Academisch Ziekenhuis Leiden, Request for Oral Argument, 3 pages, Apr. 10, 2015 [Patent Interference No. 106,007 (RES)].
Academisch Ziekenhuis Leiden, Request for Oral Argument, 3 pages, Apr. 10, 2015 [Patent Interference No. 106,008 (RES)].
Academisch Ziekenhuis Leiden, Responsive Motion 4 (to Add Two New Claims), 57 pages, Dec. 23, 2014 [Patent Interference No. 106,008 (RES)].
Academisch Ziekenhuis Leiden, Substantive Motion 1 (For Judgment that UWA Claims are Unpatentable.Under 35 U.S.C. sections 102 and 103) 69 pages, Nov. 18, 2014 [Patent Interference No. 106,007 (RES)].
Academisch Ziekenhuis Leiden, Substantive Motion 1 (for Judgment that UWA's Claims are Un patentable Under 35 U.S.C. §§ 102 and 103), 69 pages, filed Nov. 18, 2014 [Patent Interference No. 106,008 (RES)].
Academisch Ziekenhuis Leiden, Substantive Motion 2 (To Deny UWA the Benefit of AU 20049034 74), 23 pages, Nov. 18, 2014 [Patent Interference No. 106,007 (RES)].
Academisch Ziekenhuis Leiden, Substantive Motion 2 (To Deny UWA the Benefit of AU20049034 7 4, 24 pages, Nov. 18, 2014 [Patent Interference No. 106,008 (RES)].
Academisch Ziekenhuis Leiden, Substantive Motion 3 (For Judgment of Unpatentability based on Myriad), 19 pages, Nov. 18, 2014 [Patent Interference No. 106,007 (RES)].
Academisch Ziekenhuis Leiden, Substantive Motion 3 (For Judgment of Unpatentability Based on Myriad), 20 pages, Nov. 18, 2014 [Patent Interference No. 106,008 (RES)].
Academisch Ziekenhuis Leiden, *University of Western Australia* (U.S. Pat. Nos. 7,960,541, 7,807,816) v. *Academisch Ziekenhuis Leiden* (U.S. Appl. No. 13/550,210), Academisch Ziekenhuis Leiden's List of Proposed Motions, 8 pages, filed Sep. 10, 2014 [Patent Interference No. 106,008 (RES)].
Academisch Ziekenhuis Leiden, *University of Western Australia* (U.S. Pat. No. 8,455,636) v. *Academisch Ziekenhuis Leiden* (U.S. Appl. No. 11/233,495), Academisch Ziekenhuis Leiden Responsive Motion 4 (to Add Two New Claims), 65 pages, filed Dec. 23, 2014 [Patent Interference No. 106,007 (RES)].
Academisch Ziekenhuis Leiden, *University of Western Australia* (U.S. Pat. No. 7,960,541 and 7,807,816) v. *Academisch Ziekenhuis Leiden* (U.S. Appl. No. 13/550,210), Academisch Ziekenhuis Leiden Reply 1 (for Judgment that UWA's Claims are Unpatentable Under 35 U.S.C. §§ 102 and 103), 17 pages, filed Apr. 3, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden Reply 4 (in Support of Responsive Motion 4 to Add Two New Claims), 17 pages, filed Apr. 3, 2015 [Patent Interference No. 106,008 (RES)].
Academisch Ziekenhuis Leiden, *University of Western Australia* (U.S. Pat. Nos. 7,960,541 and 7,807,816) v. *Academisch Ziekenhuis Leiden* (U.S. Appl. No. 13/550,210), Academisch Ziekenhuis Leiden's Opposition 4 (To Not Exclude Evidence), 21 pages, filed May 5, 2015 [Patent Interference No. 106,008 (RES).
Academisch Ziekenhuis Leiden, *University of Western Australia* v. *Academisch Ziekenhuis Leiden*, "Principal Brief of Appellee Academisch Ziekenhuis Leiden," 69 pages, filed Mar. 28, 2017 [Interference No. 106,013].
Agrawal, S., et al., "Antisense therapeutics: is it as simple as complementary base recognition?," Molecular Medicine Today, vol. 6, pp. 72-81, Feb. 2000.
Alter, J., et al., "Systemic delivery of morpholino oligonucleotide restores dystrophin expression bodywide and improves dystrophic pathology," Nature Medicine, 12(2), pp. 175-177, Feb. 2006.
Amalfitano, A., et al., "Dystrophin Gene, protein and cell biology: Structure and mutation of the dystrophin gene," Cambridge University Press, pp. 1-28, 1997.
Anderson, J., et al., "Correlated NOS-Iµ and myf5 expression by satellite cells in mdx mouse muscle regeneration during NOS manipulation and deflazacort treatment," Neuromuscular Disorders, vol. 13(5), pp. 388-396, Jun. 2003.
Anonymous, Third Party's Statement, Japanese Application No. 2002-529499, dated Oct. 29, 2010, 28 pages (English Translation attached).
Anthony et al., "Dystrophin quantification and clinical correlations in Becker muscular dystrophy: implications for clinical trials," Brain 134(Pt 12):3547-3559 (2011).
Arap, W., et al., "Steps toward mapping the human vasculature by phage display," Nature Medicine, vol. 8, No. 2, pp. 121-127, Feb. 2002.

(56) References Cited

OTHER PUBLICATIONS

Arechavala-Gomeza, V., et al., "Comparative Analysis of Antisense Oligonucleotide Sequences for Targeted Skipping of Exon 51 During Dystrophin Pre-mRNA Splicing in Human Muscle," Human Gene Therapy, vol. 18 (9), pp. 798-810, 2007.
Aronin, N., "Expanded CAG Repeats in the Crosshairs," Nature Biotechnology, May 2009, vol. 27 (5), pp. 451-452.
Arruda, V.R., "The Role of Immunosuppression in Gene- and Cell-Based Treatments for Duchenne Muscular Dystrophy," Molecular Therapy, vol. 15, No. 6, pp. 1040-1041, Jun. 2007.
Arzumanov, A., et al., "Inhibition of HIV-1 Tat-Dependent Trans Activation by Steric Block Chimeric 2'-O- Methyl/LNA Oligoribonucleotides," Biochemistry, 2001, vol. 40 (48), pp. 14645-14654.
Atdbio, Ltd., "DNA Duplex Stability," http://www.atdbio.com/content/53/DNA-duglex-stability, 10 pages, 2008.
Austin, R.C., et al., "Cloning and Characterization of Alternatively Spliced lsoforms of Dp71," Human Molecular Genetics, 1995, vol. 4 (9), pp. 14 75/1483.
Austin, R.C., et al., "Expression and Synthesis of Alternatively Spliced Variants of Dp71 in Adult Human Brain," Neuromuscular Disorders, 2000, vol. 10(3), pp. 187-193.
Australian Government, IP Australia, Office Action for Australian Patent Application No. 2009240879, 3 pages, Jun. 22, 2011.
AVI Biopharma, Inc., "Grounds of Appeal" filed in the opposition proceeding of Ep 1619249, dated Aug. 23, 2013, 41 pages.
AVI Biopharma, Inc., Notice of Opposition filed against EP1619249, 47 pages, Jun. 23, 2009.
AVI Biopharma, Inc., Reply of the Opponent to the Grounds of Appeal, dated Jan. 8, 2014, 31 pages.
AVI Biopharma, Inc., Request for UK IPO Opinion (Section 74A & Rule 93)—EP(UK) 1619249, 24 pages, Mar. 9, 2009.
AVI Biopharma, Inc., Schematic of dystrophin exon 53 sequence with alignment of SES/AON of D61 and AON of D82-D83, 1 page, Jan. 8, 2014.
Axelrod et al., "Intestinal Transport of Gentamicin with a Novel, Glycosteroid Drug Transport Agent,".Pharmaceutical Research, vol. 15, No. 12, pp. 1876-1881, 1998.
Barabino, S.M., et al., "Antisense Probes Targeted to an Internal Domain in U2 snRNP Specifically Inhibit the Second Step of Pre-mRNA Splicing," Nucleic Acids Research, 1992, vol. 20 (17), pp. 4457-4464.
Barany, F., "The Ligase Chain Reaction in a PCR World," PCR Methods and Applications, 1991, vol. 1 (1 ), pp. 5-16.
Beggs, A.H., et al., "Detection of 98% of DMD/BMD Gene Deletions by Polymerase Chain Reaction," Human Genetics, 1990, vol. 86 (1), pp. 45-48.
Beggs, et al., "Homo Sapiens Dystrophin (DMD) Gene, Exon 55 and Partial CDS," National Center for Biotechnology Information, Database GenBank [Online], GenBank Accession No. AF213440.1, 2 pages, Jan. 27, 2002.
Bernasconi et al., "Cortisol increases transfection efficiency of cells," FEBS Lett. 419(1):103-106 (1997).
Bijvoet, A.G., et al., "Recombinant Human Acid a-Glucosidase: High Level Production in Mouse Milk, Biochemical Characteristics, Correction of Enzyme Deficiency in GSDII KO Mice.," Human Molecular Genetics, 1998, vol. 7 (11), pp. 1815-1824.
BioMarin Press Release, May 31, 2016.
Bionity.Com, "Leiden University Medical Center and Prosensa B.V. Announce First Successful Clinical Study with RNA-based Therapeutic PRO051," Jan. 3, 2008, 1 page, http://www.bionity.com/news/e/76185.
Biopharmaceutiques, Merging Pharma & Biotech, Edition 48, 3 pages, Jan. 10, 2008, http://www.biopharmacentiques.com/en/num/48.html.
Biospace, "Leiden University Medical Center and ProSensa B.V. Announce The New England Journal of Medicine Publication of First Successful Clinical Study with RNA-based Therapeutic PRO051 in Duchenne Muscular Dystrophy," 2 pages, http://www.biospace.com/news_print.aspx?NewsEntityID=81383, Dec. 27, 2007.

Boado, R., et al., "Antisense-Mediated Down-Regulation of the Human Huntingtin Gene," The Journal of Pharmacology and Experimental Therapeutics, vol. 295, No. 1, pp. 239-243, 2000.
Board of Patent Appeals and Interferences, Ex Parte Kimishige Ishizaka, Christine L. Martens and Kevin W. Moore, 24 U.S.P.Q.2d 1621, Appeal No. 91/2539, pp. 1-10, Apr. 30, 1992.
Board of Patent Appeals and Interferences, Ex parte Olav A Kristensen, 10 U.S.P.Q.2d 1701, Appeal No. 87/0697, pp. 1-5, Jan. 17, 1989.
Board of Patent Appeals and Interferences, Ex Parte Prebin M. Remark, 15 U.S.P.Q.2d 1498, Appeal No. 87/2422, pp. 1-12, Jan. 25, 1990.
Board of Patent Appeals and Interferences, Order—Motion Times—37 C.F.R., §41.104(c) 6 pages, entered Jul. 18, 2014.
Board of Patent Appeals and Interferences, Standing Order, 81 pages, entered Mar. 8, 2011.
Bonifazi, E., et al., "Use of RNA Fluorescence In Situ Hybridization in the Prenatal Molecular Diagnosis of Myotonic Dystrophy Type I," Clinical Chemistry, vol. 52 (2), pp. 319-322, 2006.
Braida, C., et al., "Variant CCG and GGC Repeats Within the CTG Expansion Dramatically Modify Mutational Dynamics and Likely Contribute Toward Unusual Symptoms in Some Myotonic Dystrophy Type 1 Patients," Human Molecular Genetics, vol. 19, No. 8, pp. 1399-1412, Jan. 2010.
Braun et al., "In vitro and in vivo effects of glucocorticoids on gene transfer to skeletal muscle," FEBS Lett. 454(3):277-282 (1999).
Bremmer-Bout, M., et al., "Targeted Exon Skipping in Transgenic hDMD Mice: A Model for Direct Preclinical Screening of Human-Specific Antisense Oligonucleotides," Molecular Therapy, vol. 10, No. 2, pp. 232-240, Aug. 2004.
Brett, D., et al., "EST Comparison Indicates 38% of Human mRNAs Contain Possible Alternative Splice Forms," FEBS Letters, vol. 474 (1), pp. 83-86, 2000.
Brolin, C., et al., "Antisense mediated exon skipping therapy for duchenne muscular dystrophy (DMD)," Artificial DNA, RNA & XNA, vol. 2, No. 1, pp. 6-15, Jan. 2011.
Brown, M.D., et al., "Gene Delivery with Synthetic (Non Viral) Carriers," International Journal of Pharmaceutics, vol. 229 (1-2), pp. 1-21, 2001 (Abstract).
Buck, G.A., et al., "Design Strategies and Performance of Custom DNA Sequencing Primers," BioTechniques, vol. 27 (3), pp. 528-536, 1999.
Buczko, W., et al., "Modulation of Plasminogen Activator Inhibitor Type-1 Biosynthesis in Vitro and in Vivo with Oligo(nucleoside phosphorothioate)s and Related Constructs," Pharmacology & Therapeutics, vol. 76, No. 1-3, pp. 161-175, 1997.
Burnett, R., et al., "DNA Sequence-Specific Polyamides Alleviate Transcription Inhibition Associated with Long GAA.TTC Repeats in Friedreich's Ataxia," Proceedings of the National Academy of Sciences of the United States of America, 2006, vol. 103 (31), pp. 11497-11502.
Bushby et al., "Report on the 124th ENMC International Workshop. Treatment of Duchenne muscular dystrophy; defining the gold standards of management in the use of corticosteroids. Apr. 2-4, 2004, Naarden, The Netherlands," Neuromuscul. Disord. 14(8-9):526-534 (2004).
Canadian Intellectual Property Office, Office Action for Canadian Patent Application No. 2,524,255, 2 pages, Jul. 6, 2011.
Caplen, N.J., et al., "Rescue of polyglutamine-mediated cytotoxicity by double-stranded RNA-mediated RNA Interference Human Molecular Genetics," Human Molecular Genetics, 2002, vol. 11 (2), pp. 175-184.
Cartegni, L., et al., "Correction of Disease-Associated Exon Skipping by Synthetic Exon-Specific Activators," Nature Structural Biology, vol. 10 (2), pp. 120-125, 2003.
Cartegni, L., et al., "Listening to Silence and Understanding Nonsense: Exonic Mutations that Affect Splicing," Nature Review Genetics, 2002, vol. 3 (4), pp. 285-298.
Case-Green, S.C., et al., "Studies on the Base Pairing Properties of Deoxyinosine by Solid Phase Hybridisation to Oligonucleotides," Nucleic Acids Research, vol. 22 (2), pp. 131-136, 1994.

(56) References Cited

OTHER PUBLICATIONS

Cavanaugh, D.L., Third-Party Submission Under 35 U.S.C. §122(e) and 37 C.F.R. § 1.290 for U.S. Appl. No. 11/233,495, 6 pages, Jun. 5, 2013.
Chamberlain, "Dystrophin Levels Required for Genetic Correction of Duchenne Muscular Dystrophy," Basic and Applied Myology, vol. 7 (3-4), pp. 251-255, 1997.
Chan et al., "Antisense oligonucleotides: from design to therapeutic application," Clin. Exp. Pharmacol. Physiol. 33(5-6):533-540 (2006).
Chaubourt, E., et al., "Muscular Nitric Oxide Synthase (muNOS) and Utrophin," Journal of Physiology Paris, 2002, vol. 96 (1-2), pp. 43-52.
Cirak et al., "Exon skipping and dystrophin restoration in patients with Duchenne muscular dystrophy after systemic phosphorodiamidate morpholino oligomer treatment: an open-label, phase 2, dose-escalation study," Lancet 378(9791):595-605 (2011).
Cooper, T.A., "Neutralizing Toxic Rna," Science, vol. 325, pp. 272-273, Jul. 2009.
Coulter, L.R., et al., "Identification of a New Class of Exonic Splicing Enhancers by In Vivo Selection," Molecular and Cellular Biology, 1997, vol. 17 (4), pp. 2143-2150.
Crooke, S.T., "Basic Principles of Antisense Therapeutics, Handbook of Experimental Pharmacology: Antisense Research and Application," Springer-Verlag Berlin Heidelberg, 1998, vol. 131, pp. 1-50.
Dahlqvist, C., et al., "Functional Notch Signaling is Required for BMP4-Induced Inhibition of Myogenic Differentiation," Development, 2003, vol. 130 (24), pp. 6089-6099.
De Angelis, F.G., et al., "Chimeric snRNA Molecules Carrying Antisense Sequences Against The Splice Junctions of Exon 51 of the Dystrophin Pre-mRNA Induce Exon Skipping and Restoration of a Dystrophin Synthesis in 848-50 DMD Cells," Proceedings of the National Academy of Sciences of the United States of America, Jul. 9, 2002, vol. 99 (14), pp. 9456-9461.
Declaration of Judith C.T. van Deutekom under 37 C.F.R. 1.131 filed in U.S. Appl. No. 13/094,548. The declaration is dated Sep. 30, 2012.
Denny, P., et al., "Oligo-Riboprobes. Tools for in Situ Hybridization," Histochemistry, 1988, vol. 89 (5), pp. 481-483.
Devor, E.J., et al., "Oligonucleotide Yield, Resuspension, and Storage," Integrated DNA Technologies, pp. 1-11, 2005.
Dickson, G., et al., "Screening for Antisense Modulation of Dystrophin Pre-mRNA Splicing," Neuromuscular Disorders, 2002, vol. 12 (Suppl 1), pp. S67-S70.
Dinham, R., Opinion Under Section 74(A) in relation to Patent No. EP (UK) 1619249 in the name of Academisch Ziekenhuis Leiden, 14 pages, Jun. 4, 2009.
Dirksen, W.P., et al., "Mapping the SF2/Asf Binding Sites in the Bovine Growth Hormone Exonic Splicing Enhancer," The Journal of Biological Chemistry, 2000, vol. 275 (37), pp. 29170-29177.
Dorchies, O.M., et al., "Green Tea Extract and its Major Polyphenol (-)-Epigallocatechin Gallate Improve Muscle Function in a Mouse Model for Duchenne Muscular Dystrophy," American Journal of Physiology—Cell Physiology, vol. 290 (2), pp. C616-C625, 2006.
Duboc, D., et al., "Effect of Perindopril on the Onset and Progression of Left Ventricular Dysfunction in Duchenne Muscular Dystrophy," Journal of the American College of Cardiology, 2005, vol. 45 (6), pp. 855-857.
Dubowitz, V., "Foreword," Neuromuscular Disorders, 12, pp. S1-S2, 2002.
Dubowitz, V., "Special Centennial Workshop—101st ENMC International Workshop: Therapeutic Possibilities in Duchenne Muscular Dystrophy, Nov. 30-Dec. 2, 2001, Naarden, The Netherlands," Neuromuscular Disorders, vol. 12, pp. 421-431, 2002.
Dunckley, M.G., et al., "Modification of Splicing in the Dystrophin Gene in Cultured Mdx Muscle Cells by Antisense Oligoribonucleotides," Human Molecular Genetics, 1995, vol. 5 (1), pp. 1083-1090.
Dunckley, M.G., et at, "Modulation of Splicing in the DMD Gene by Antisense Oligoribonucleotides," Nucleosides & Nucleotides, 1997, vol. 16 (7-9), pp. 1665-1668.

Ede, N.J., et al., "Routine Preparation of Thiol Oligonucleotides: Application to the Synthesis of Oligonucleotide-Peptide Hybrids," Bioconjugate Chemistry, 1994, vol. 5 (4), pp. 373-378.
Eder, I.E., et al., "Inhibition of LNCaP prostate cancer cells by means of androgen receptor antisense oligonucleotides," Cancer Gene Therapy, vol. 7, No. 7, pp. 997-1007, 2000.
El-Andaloussi, S., et al., "Induction of Splice Correction by Cell-Penetrating Peptide Nucleic Acids," The Journal of Gene Medicine, 2006, vol. 8 (10), pp. 1262-1273 (Abstract).
Erba, H.P., et al., "Structure, Chromosome Location, and Expression of the Human γ-Actin Gene: Differential Evolution, Location, and Expression of the Cytoskeletal β- and γ-Actin Genes," Molecular and Cellular Biology, 1988, vol. 8 (4), pp. 1775-1789.
Errington, S.J., et al., "Target Selection for Antisense Oligonucleotide Induced Exon Skipping in the Dystrophin Gene," The Journal of Gene Medicine, 2003, vol. 5 (6), pp. 518-527.
Espinos, E., et al., "Efficient Non-Viral DNA-Mediated Gene Transfer to Human Primary Myoblasts Using Electroporation," Neuromuscular Disorders, 2001, vol. 11 (4), pp. 341-349.
European Patent Office, Communication pursuant to Article 94(3) EPC, Application No. 10177969.2-1404, Aug. 22, 2013, 5 pages.
European Patent Office, Communication pursuant to Article 94(3) EPC, Application No. 10718717.1-1401, Dec. 19, 2013, 5 pages.
European Patent Office, Decision to refuse a European Patent application, Application No. 01979073.2-1402, Jan. 7, 2015, 10 pages.
European Patent Office, European Search Report, Annex, Application No. EP 03077205, dated Dec. 10, 2003, 6 pages.
European Patent Office, Extended European Search Report, Application No. 10177969.2-2401, dated Dec. 16, 2010, 7 pages.
European Patent Office, International Search Report, International Application No. PCT/NL2008/050673, dated Feb. 9, 2009, 8 pages.
European Patent Office, International Search Report, PCT/NL2013/050306, dated Jul. 19, 2013, 6 pages.
European Patent Office, Office Action for European Patent Application No. EP05076770.6, 5 pages, dated Jan. 29, 2007.
European Patent Office, Translation of Japanese Patent Application No. 2000-125448 (D64), 31 pages, dated Sep. 27, 2000.
European Patent Office, Translation of Japanese Patent Application No. 2000-256547 (D66), 42 pages, dated Aug. 23, 2001.
Evers, M.M., et al., "Targeting Several CAG Expansion Diseases by a Single Antisense Oligonucleotide," PLoS ONE, vol. 6 (9), pp. 1-11, Sep. 2011.
Exondys 51™ prescribing information highlights (eteplirsen label) (dated Sep. 2016).
Fainsod, A., et al., "The Dorsalizing and Neural Inducing Gene Follistatin is an Antagonist of BMP-4," Mechanisms of Development, 1997, vol. 63 (1), pp. 39-50.
FDA News Release, Sep. 19, 2016.
Federal Angecy for Medicines and Health Products, Letter from Federal Agency for Medicines and Health Products to Prosensa, regarding a Phase 1/11, open label, escalating dose, pilot study to assess the effect, safety, tolerability and pharmacokinetics of multiple subcutaneous doses of PRO051 in patients with Duchenne muscular dystrophy, 2 pages, Jan. 9, 2008.
Feener, C.A., et al., "Alternative Splicing of Human Dystrophin mRNA Generates Isoforms at the Carboxy Terminus," Nature, 1989, vol. 338 (6215), pp. 509-511.
Fiszer, A., et al., "An Evaluation on Oligonucleotide-Based Therapeutic Strategies for PolyQ Diseases," BMC Molecular Biology, 2012, vol. 13 (1), pp. 1-12.
Fluiter, K., et al., "In Vivo Tumor Growth Inhibition and Biodistribution Studies of Locked Nucleic Acid (LNA) Antisense Oligonucleotides," Nucleic Acids Research, 2003, vol. 31 (3), pp. 953-962.
Folini, M., et al., "Antisense oligonucleotide-mediated inhibition of hTERT, but not hTERC, induces rapid cell growth decline and apoptosis in the absence of telomere shortening in human prostate cancer cells," European Journal of Cancer, vol. 41, No. 4, pp. 624-634, 2005.
Fu, Y.H., et al., "An Unstable Triplet Repeat in a Gene Related to Myotonic Muscular Dystrophy," Science, 1992, vol. 255 (5049), pp. 1256-1258.

(56) References Cited

OTHER PUBLICATIONS

Furling, D., et al., "Viral Vector Producing Antisense RNA Restores Myotonic Dystrophy Myoblast Functions," Gene Therapy, 2003, vol. 1 0 (9), pp. 795-802.

Gagnon, K.T., et al, "Allele-Selective Inhibition of Mutant Huntingtin Expression with Antisense Oligonucleotides Targeting the Expanded CAG Repeat," Biochemistry, 2010, vol. 49 (47), pp. 10166-10178.

Galderisi, U., et al., "Antisense Oligonucleotides as Therapeutic Agents," Journal of Cellular Physiology, 1999, vol. 181 (2), pp. 251-257.

Galderisi, U., et al., "Myotonic Dystrophy: Antisense Oligonucleotide Inhibition of DMPK Gene Exression in Vitro," Biochemical and Biophysical Research Communications, 1996, vol. 221 (3), pp. 750-754.

Garcia-Blanco, M.A., et al., "Alternative Splicing in Disease and Therapy," Nature Biotechnology, May 2004, vol. 22 (5), pp. 535-546.

Gen Bank, Accession No. AZ993191.1, 2M0278E12F Mouse 10kb plasmid UUGC2M library Mus muscu genomic clone UUGC2M0278E12 F, genomic survey sequence, entry created and last updated on Apr. 27, 2001, 2 pages.

Genbank, Accession No. EW162121.1, rfat0126_k17 .y1 fat Sus scrofa cDNA 5-, mRNA sequence, entry created on Aug. 13, 2007, last updated on Mar. 3, 2011, 2 pages.

Ghosh, P. et at, "Mannose 6-Phosphate Receptors: New Twists in the Tale," Natural Reviews Molecular Cell Biology, Mar. 2003, vol. 4 (3), pp. 202-212.

Ginjaar, 1.8., et al., "Dystrophin Nonsense Mutation Induces Different Levels of Exon 29 Skipping and Leads to Variable Phenotypes within One BMD Family," European Journal of Human Genetics, 2000, vol. 8 (10), pp. 793-796.

Glaxosmithkline, Inc., Press Release, "GSK and Prosensa Announce Primary Endpoint Not Met in Phase I11 Study of Drisapersen in Patients With Duchenne Muscular Dystrophy," 3 pages, Sep. 20, 2013.

Goemans et al., "Comparison of ambulatory capacity and disease progression of Duchenne muscular dystrophy subjects enrolled in the drisapersen DMD114673 study with a matched natural history cohort of subjects on daily corticosteroids," Neuromuscul. Disord. 27(3):203-213 (2017) (Epub Nov. 25, 2016).

Goemans, N.M., et al., "Systemic Administration of PRO051 in Duchenne's Muscular Dystrophy," The New England Journal of Medicine, vol. 364 (16), pp. 1513-1522, 2011.

Gollins, H., et al., "High-Efficiency Plasmid Gene Transfer Into Dystrophic Muscle," Gene Therapy, 2003, vol. 10(6), pp. 504-512.

Gonzalez-Barriga et al., "Design and Analysis of Effects of Triplet Repeat Oligonucleotides in Cell Models for Myotonic Dystrophy," vol. 2, No. e81, pp. 1-23, 2013.

Grady, D., "Early Drug Test Shows Promise in Treating Muscular Dystrophy," International Herald Tribune, Jan. 2008, Health and Science, p. 9.

Grady, D., "Promising Dystrophy Drug Clears Early Test," The New York Times, 2 pages, Dec. 27, 2007.

Gramolini, A.O., et al., "Expression of the Utrophin Gene During Myogenic Differentiation," Nucleic Acids Research, 1999, vol. 27 (17), pp. 3603-3609.

Granchelli, J.A., et al., "Pre-Clinical Screening of Drugs Using the mdx Mouse," Neuromuscular Disorders, 2000, vol. 1 O (4-5), pp. 235-239.

Gryaznov, S.M., "Oligonucleotide N3'- PS' Phosphoramidates as Potential Therapeutic Agents," Biochimica et Biophysica Acta, 1999, vol. 1489, pp. 131-140.

Habara, Y., et al., "In Vitro Splicing Analysis Showed that Availability of a Cryptic Splice Site is not a Determinant for Alternative Splicing Patterns Caused by +1 G-A Mutations in lntrons of the Dystrophin Gene," Journal of Medical Genetics, vol. 46 (8), pp. 542-547, 2009.

Hagiwara, Y., et al., "A Novel Point Mutation (G$^{-1}$to T) in a 5' Splice Donor Site of lntron 13 of The Dystrophin Gene Results in Exon Skipping and is Responsible for Becker Muscular Dystrophy.," American Journal of Human Genetics, 1994, vol. 54 (1), pp. 53-61.

Hanoa, V. et al., "The AUUCU Repeats Responsible for Spinocerebellar Ataxia Type 10 Form Unusual RNA Hairpins," The Journal of Biological Chemistry, 2005, vol. 280 (32), pp. 29340-29345.

Hansen, S., "Product Development—Addition by subtraction," BioCentury, The Bernstein Report on BioBusiness, Jan. 7, 2008, p. A28.

Hardiman et al., "Methylprednisolone selectively affects dystrophin expression in human muscle cultures," Neurology 43(2):342-345 (1993).

Harding, P.L., et al., "The Influence of Antisense Oligonucleotide Length on Dystrophin Exon Skipping," Molecular Therapy, Jan. 2007, vol. 15 (1), pp. 157-166.

Harrison, J.G., et al., "Synthesis and Hybridization Analysis of a Small Library of Peptide—Oligonucleotide Conjugates," Nucleic Acids Research, 1998, vol. 26 (13), pp. 3136-3145.

Hashol T, L., et al., "Antisense Downregulation of Mutant Huntingtin in a Cell Model," Journal of Gene Medicine, 2003, vol. 5 (6), pp. 528-538.

Hassan, A.B., "Keys to the Hidden Treasures of the Mannose 6-Phosphate/insulin-Like Growth Factor 2 Receptor," American Journal of Pathology, Jan. 2003, vol. 162 (1), pp. 3-6.

Heemskerk, H., et al., "Development of Antisense-Mediated Exon Skipping as a Treatment for Duchenne Muscular Dystrophy," Annals of the New York Academy of Sciences, 2009, vol. 1175, pp. 71-79.

Heemskerk, H.A., et al., "In Vivo Comparison of 2'-O-Methyl Phosphorothioate and Morpholino Antisense Oligonucleotides for Duchenne Muscular Dystrophy Exon Skipping," The Journal of Gene Medicine, 2009, vol. 11 (3), pp. 257-266.

Heemskerk, H.A., et al., "Preclinical PK and PD Studies on 2'-O-Methyl--phosphorothioate RNA Antisense Oligonucleotides in the mdx Mouse Model," Molecular Therapy, Jun. 2010, vol. 18 (6), pp. 1210-1217.

Henderson, A.M., et al., "The Basic Helix-Loop-Helix Transcription Factor HESR1 Regulates Endothelial Cell Tube Formation," The Journal of Biological Chemistry, vol. 276 (9), pp. 6169-6176, 2001.

Highfield, R., "Roger Highfield rounds up latest snippets of science, from a new treatment for muscular dystrophy, detecting tumours to the benefits of cooking vetables," Science: Boffin log, Jan. 1, 2008, 5 pages.

Hoffman, E.P., "Skipping Toward Personalized Molecular Medicine," The New England Journal of Medicine, Dec. 2007, vol. 357 (26), pp. 2719-2722.

Hoffman, E.P., et al., "Somatic Reversion/Suppression of the Mouse mdx Phenotype in Vivo," Journal of the Neurological Sciences, 1990, vol. 99 (1), pp. 9-25.

Hua, Y., et al., "Antisense Correction of SMN2 Splicing in the CNS Rescues Necrosis in a Type Ill SMA Mouse Model," Genes and Development, 2010, vol. 24 (15), pp. 1634-1644.

Hussein et al. "The effects of glucocorticoid therapy on the inflammatory and dendritic cells in muscular dystrophies," Int. J. Exp. Pathol. 87(6):451-461 (2006).

Hussey, N.D., et al., "Analysis of Five Duchenne Muscular Dystrophy Exons and Gender Determination Using Conventional Duplex Polymerase Chain Reaction on Single Cells," Molecular Human Reproduction, 1999, vol. 5 (11), pp. 1089-1094.

Hyndman, A.G., "High Affinity Binding of Transferrin in Cultures of Embryonic Neurons from the Chick Retina," Brain Research, 1991, vol. 564 (1), pp. 127-131.

Iezzi, S., et al, "Deacetylase Inhibitors Increase Muscle Cell Size by Promoting Myoblast Recruitment and Fusion through Induction of Follistatin," Developmental Cell, May 2004, vol. 6(5), pp. 673-684.

Ikezawa, M., et al., "Dystrophin Gene Analysis on 130 Patients with Duchenne Muscular Dystrophy with a Special Reference to Muscle mRNA Analysis," Brain & Development, 1998, vol. 20 (3), pp. 165-168.

International Preliminary Examining Authority—European Patent Office, International Preliminary Examination Report for International Application No. PCT/NL01/00697, 2 pages, Aug. 1, 2002.

(56) References Cited

OTHER PUBLICATIONS

International Searching Authority—European Patent Office, Annex to the European Search Report—Application No. EP03077205, dated Nov. 19, 2003, 1 page.
International Searching Authority—US, International Search Report, International Application No. PCT/US10/48532,5 pages, dated Jan. 26, 2011.
International Searching Authority—European Patent Office, International Preliminary.Report on Patentability and Written Opinion, International Application No. PCT/EP2007/054842, dated Nov. 21, 2008, 8 pages.
International Searching Authority—European Patent Office, International Search Report, International Application No. PCT/EP2007/054842 3 pages, dated Aug. 21, 2007.
International Searching Authority—European Patent Office, International Search Report, International Application No. PCT/NL 2008/050673, 8 pages, dated Sep. 2, 2009.
International Searching Authority—European Patent Office, International Search Report, International Application No. PCT/NL01/00697, 2 pages, dated Dec. 21, 2001.
International Searching Authority—European Patent Office, International Search Report, International Application No. PCT/NL2004/000196, 7 pages, dated Dec. 10, 2004.
International Searching Authority—European Patent Office, International Search Report, International Application No. PCT/NL2006/000209, 4 pages, dated Oct. 5, 2006.
International Searching Authority—European Patent Office, International Search Report, International Application No. PCT/NL2008/050470, 4 pages, dated Jul. 2, 2009.
International Searching Authority—European Patent Office, International Search Report, International Application No. PCT/NL2008/050475, 30 pages, dated Jun. 25, 2009.
International Searching Authority—European Patent Office, International Search Report, International Application No. PCT/NL2009/050006, 5 pages, dated Jul. 31, 2009.
International Searching Authority—European Patent Office, International Search Report, International Application No. PCT/NL2009/050113, 8 pages, dated Jun. 30, 2010.
International Searching Authority—European Patent Office, International Search Report, International Application No. PCT/NL2010/050230, 5 pages, dated Jun. 24, 2010.
International Searching Authority—European Patent Office, International Search Report, International Application No. PCT/NL2013/050487, 8 pages, dated Dec. 20, 2013.
Ito, T., et al., "One of three Examined Purine-Rich Sequences Selected from Dystrophin Exons Exhibits Splicing Enhancer Activity," Acta Myologica, 2001, vol. 20, pp. 151-153.
Ito, T., et al., "Purine-Rich Exon Sequences are Not Necessarily Splicing Enhancer Sequence in the Dystrophin Gene," The Kobe Journal of Medical Sciences, Oct. 2001, vol. 47 (5), pp. 193-202.
Itoh et al., "Allergic Contact Dermatitis Due to Topical Drugs Contaiing Corticosteroids," Skin Research, 24(2), pp. 270-271, 1982.
Jou, C., et al., "Deletion Detection in the Dystrophin Gene by Multiplex Gap Ligase Chain Reaction and lmmunochromatographic Strip Technology," Human Mutation, 1995, vol. 5 (1), pp. 86-93.
KA Tholieke Universiteit Leuven, Letter from Katholieke Universiteit Leuven to Dr. N. Goemans, Child Neurology regarding Study Phase 1/11, PRO051-02, 5 pages, dated Jan. 22, 2008 (translation provided).
Kandimalla, E.R., et al., "Effects of Phosphorothioate Oligodeoxyribonucleotide and Oligoribonucleotides on Human Complement and Coagulation," Bioorganic & Medicinal Chemistry Letters, vol. 8, No. 16, pp. 2103-2108, 1998.
Karras, J.G., et al., "Deletion of Individual Exons and Induction of Soluble Murine Interleukin—5 Receptor-α Chain Expression through Antisense Oligonucleotide-Mediated Redirection of Pre- mRNA Splicing," Molecular Pharmacology, 2000, vol. 58 (2), pp. 380-387.

Kendall, G.C., et at, "Dantrolene Enhances Antisense-Mediated Exon Skipping in Human and Mouse Models of Duchenne Muscular Dystrophy," Science Translational Medicine, vol. 4 (164), 26 pages, Dec. 12, 2012.
Kerr, K., et al., "BMP Regulates Skeletal Myogenesis at Two Steps," Molecular and Cellular Proteomics, 2003, vol. 2 (9), pp. 976.
Khan, "Corticosteroid therapy in Duchenne muscular dystrophy," J. Neurol. Sci. 120:8-14 (1993).
Kinali, M., et al., "Local Restoration of Dystrophin Expression With the Morpholino Oligomer AV1-4658 in Duchenne Muscular Dystrophy: A Single-Blind, Placebo-Controlled, Dose-Escalation, Proof-of-Concept Study," The Lancet. Neurology, 2009, vol. 8 (10), pp. 918-928.
Kneppers et al., Point mutation screening for 16 exons of the dystrophin gene by multiplex single-strand conformation polymorphism analysis, 1995, Human Mutation, vol. 5, pp. 235-242.
Kohler, W., "Experimenteel middel voor Duchenne," http://www.ntc.nl/nieuws/2007/12/27/experimenteel-middel-voor-duchenne-11458530-a1030722, 4 pages with English Translation, Dec. 27, 2007.
Krainer, A., Declaration of Dr. Adrian Krainer, 7 pages, Jul. 21, 2010, (submitted in Third Party's Statement for JP Application No. 2002-529499 on Oct. 29, 2010).
Kurreck, J., et al., "Design of Antisense Oligonucleotides Stabilized by Locked Nucleic Acids," Nucleic Acids Research, 2002, vol. 30 (9), pp. 1911-1918.
Langlois, M.A., et al., "Hammerhead Ribozyme-Mediated Destruction of Nuclear Foci in Myotonic Dystrophy Myoblasts," Molecular Therapy, 2003, vol. 7 (5), pp. 670-680.
Laptev, A.V., et al., "Specific Inhibition of Expression of a Human Collagen Gene (col. 1A1) with Modified Antisense Oligonucleotides. The Most Effective Target Sites are Clustered in Double Stranded Regions of the Predicted Secondary Structure for the mRNA," Biochemistry, 1994, vol. 33 (36), pp. 11033-11039.
Lebedev, Y., et al.,"Oligonucleotides containing 2-aminoadenine and 5-methylcytosine are more effective as primers for PCR amplification than their nonmodified counterparts," Genetic Analysis: Biomolecular Engineering, vol. 13, pp. 15-21, 1996.
Lee, J.E., et al., "RNase H-Mediated Degradation of Toxic RNA in Myotonic Dystrophy Type 1," Proceedings of the National Academy of Sciences of the United States of America, Mar. 2012, vol. 109 (11), pp. 4221-4226.
Lee, J.H., et al., "Receptor Mediated Uptake of Peptides that Bind the Human Transferrin Receptor," European Journal of Biochemistry / FEBS, 2001, vol. 268 (7), pp. 2004-2012.
Lewin, B., "Genes VII," Oxford University Press, 2000, Chapters: 1, 5, 22; pp. 29, 126, 129, 686, 704, 705.
Lewin, B., "Nuclear Splicing," Genes VII, Chapter 22, pp. 704-705, Jan. 2000.
Liu, H.X., et al., "A Mechanism for Exon Skipping Caused by Nonsense or Missense Mutations in BRCA1 and Other Genes," Nature Genetics, Jan. 2001, vol. 27 (1), pp. 55-58.
Liu, H.X., et al., "Identification of Functional Exonic Splicing Enhancer Motifs Recognized by Individual SR Proteins," Genes & Development, 1998, vol. 12 (13), pp. 1998-2012.
Liu, W., et al., "Specific Inhibition of Huntington's Disease Gene Expression by siRNAs in Cultured Cells," Proceedings of the Japan Academy, 2003, vol. 79, pp. 293-298.
Liu, Y.C., et al., "Efficiency of DNA Transfection of Rat Heart Myoblast Cells H9c2(2-1) by Either Polyethyleneimine or Electroporation," Applied Biochemistry and Biotechnology, 2011, vol. 164 (7), pp. 1172-1182.
Lonza Cologne AG, "Amaxa Cell Line Nucleofector Kit V" for C2C12, 4 pages, 2009.
Lu, Q.L., et al., "Functional Amounts of Dystrophin Produced by Skipping the Mutated Exon in the mdx Dystrophic Mouse ," Nature Medicine, Aug. 2003, vol. 9 (8), pp. 1009-1014.
Lu, Q.L., et al., "Massive Idiosyncratic Exon Skipping Corrects the Nonsense Mutation in Dystrophic Mouse Muscle and Produces Functional Revertant Fibers by Clonal Expansion," The Journal of Cell Biology, 2000, vol. 148 (5), pp. 985-995.

(56) References Cited

OTHER PUBLICATIONS

Lu, Q.L., et al., "Non-Viral Gene Delivery in Skeletal Muscle: A Protein Factory," Gene Therapy, 2003, vol. 10 (2), pp. 131-142.

Lu, Q.L., et al., "Systemic Delivery of Antisense Oligoribonucleotide Restores Dystrophin Expression in Body-Wide Skeletal Muscles," Proceedings of the National Academy of Sciences of the United States of America, Jan. 2005, vol. 102 (1), pp. 198-203.

Ludolph, D.C., et al., "Transcription Factor Families: Muscling in on the Myogenic Program," FASEB Journal, 1995, vol. 9 (15), pp. 1595-1604.

Magana, J.J., et al., "Perspectives on Gene Therapy in Myotonic Dystrophy Type 1," Journal of Neuroscience Research, 2011, vol. 89 (3), pp. 275-285.

Mann, C.J., et al., "Antisense-Induced Exon Skipping and Synthesis of Dystrophin in the mdx Mouse," Proceedings of the National Academy of Sciences of the United States of America, Jan. 2001, vol. 98 (1), pp. 42-47.

Mann, C.J., et al., "Improved Antisense Oligonucleotide Induced Exon Skipping in the mdx Mouse Model of Muscular Dystrophy," The Journal of Gene Medicine, 2002, vol. 4 (6), pp. 644-654.

Manning et at, "What has the mdx mouse model of Duchenne muscular dystrophy contributed to our understanding of this disease?" J. Muscle Res. Cell Motil. 36(2):155-167 (2015).

Manzur et al., "Glucocorticoid corticosteroids for Duchenne muscular dystrophy (Review)," Cochrane Database Syst. Rev. 1:1-72 (2008).

Martin, F.H., et al., "Base Pairing Involving Deoxyinosine: Implications for Probe Design," Nucleic Acids Research, vol. 13 (24), pp. 8927-8938, 1985.

Martiniuk, F., et al., "Correction of Glycogen Storage Disease Type II by Enzyme Replacement with a Recombinant Human Acid Maltase Produced by Over-Expression in a CHO-DHFR(Neg) Cell Line," Biochemical and Biophysical Research Communications, Oct. 2000, vol. 276 (3), pp. 917-923 (Abstract).

Matsuo, M., "Duchenne/Becker Muscular Dystrophy: From Molecular Diagnosis to Gene Therapy," Brain & Development, 1996, vol. 18 (3), pp. 167-172.

Matsuo, M., et al., "Duchenne and Becker Muscular Dystrophy: From Gene Diagnosis to Molecular Therapy," IUBMB Life, 2002, vol. 53 (3), pp. 147-152.

Matsuo, M., et al., "Exon Skipping during Splicing of Dystrophin mRNA Precursor due to an Intraexon Deletion in the Dystrophin Gene of Duchenne Muscular Dystrophy Kobe," The Journal of Clinical Investigation, 1991, vol. 87 (6), pp. 2127-2131.

Matsuo, M., et al., "Partial Deletion of a Dystrophin Gene Leads to Exon Skipping and to Loss of an Intra-Exon Hairpin Structure from the Predicted mRNA Precursor," Biochemical and Biophysical Research Communications, 1992, vol. 182 (2), pp. 495-500.

Matteucci, M., "Structural Modifications Toward Improved Antisense Oligonucleotides," Perspective in Drug Discovery and Design, 1996, vol. 4 (1), pp. 1-16.

McClorey, G., et al., "Antisense Oligonucleotide-Induced Exon Skipping Restores Dystrophin Expression in Vitro m a Canine Model of DMD," Gene Therapy, vol. 13, pp. 1373-1381, 2006.

McClorey, G., et al., "Induced Dystrophin Exon Skipping in Human Muscle Explants," Neuromuscular Disorders, 2006, vol. 16 (9-10), pp. 583-590.

Medical News Today, "New Clinical Trial Results Show How Personalized Medicine Will Alter Treatment of Genetic Disorders," http://www.medicalnewstoday.com/releases/92777.php, 2 pages, Dec. 29, 2007.

Merlini and Sabatelli, "Improving clinical trial design for Duchenne muscular dystrophy," BMC Neurol. 15:153 (2015).

Miller, K.J., et al., "Antisense Oligonucleotides: Strategies for Delivery," Pharmaceutical Science and Technology Today, Dec. 1998, vol. 1 (9), pp. 377-386.

Monaco, A.P., et al., "An Explanation for the Phenotypic Differences between Patients Bearing Partial Deletions of the DMD Locus," Genomics, 1988, vol. 2 (1), pp. 90-95.

Moon, I.J., et al., "Target Site Search and Effective Inhibition of Leukaemic Cell Growth by a Covalently Closed Multiple Anti-Sense Oligonucleotide to c-myb," The Biochemical Journal, 2000, vol. 346, pp. 295-303.

Moxley et al., "Practice parameter: corticosteroid treatment of Duchenne dystrophy: report of the Quality Standards Subcommittee of the American Academy of Neurology and the Practice Committee of the Child Neurology Society," Neurology 64(1):13-20 (2005).

Mulders, S.A., et al., "Molecular Therapy in Myotonic Dystrophy: Focus on RNA Gain-of Function," Human Molecular Genetics, 2010, vol. 19 (R1), pp. R90-R97.

Mulders, S.A., et al., "Triplet-Repeat Oligonucleotide-Mediated Reversal of RNA Toxicity in Myotonic Dystrophy," Proceedings of the National Academy of Sciences of the United States of America, Aug. 2009, vol. 106 (33), pp. 13915-13920.

Munroe, S.H., "Antisense RNA Inhibits Splicing of Pre-mRNA in Vitro," The EMBO Journal, 1988, vol. 7 (8), pp. 2523-2532.

Muntoni et al., "128th ENMC International Workshop on 'Preclinical optimization and Phase I/II Clinical Trials Using Antisense Oligonucleotides in Duchenne Muscular Dystrophy' Oct. 22-24, 2004, Naarden, The Netherlands," Neuromuscul. Disord. 15(6):450-457 (2005) (Epub Apr. 18, 2005).

Muntoni et al., "Steroids in Duchenne muscular dystrophy: from clinical trials to genomic research," Neuromuscul. Disord. 12 Suppl 1:S162-S165 (2002).

Muntoni, F., et al., "149th ENMC International Workshop and 1st TREAT-NMD Workshop on: "Planning Phase 1 /11 Clinical trials using Systemically Delivered Antisense Oligonucleotides in Duchenne Muscular Dystrophy"," Neuromuscular Disorders, 2008, vol. 18, pp. 268-275.

Muntoni, F., et al., "A Mutation in the Dystrophin Gene Selectively Affecting Dystrophin Expression in the Heart," The Journal of Clinical Investigation, Aug. 1995, vol. 96 (2), pp. 693-699.

Muntoni, F., et al., "Targeting RNA to Treat Neuromuscular Disease," Nature Reviews Drug Discovery, Aug. 2011, vol. 10 (8), pp. 621-637.

Nakamori, M, et al., "Stabilization of Expanded (CTG)•(CAG) Repeats by Antisense Oligonucleotides," Molecular Therapy, vol. 19, No. 12, pp. 2222-2227, Dec. 2011.

Nakamura, A., et al., "Exon Skipping Therapy for Duchenne Muscular Dystrophy," Neuropathology, 2009, vol. 29 (4), pp. 494-501.

Nakamura, et al., "The Latest Finding on Muscular Dystrophy," Medical Online, vol. 42, No. 4, pp. 382-386, 2008 (English translation attached 5 pgs.).

Nederlandsch Octrooibureau, "Comparative analysis of AONs for inducing the skipping of exon 45 or 53 from the dystrophin gene in human control muscle cells," EP1619249, 3 pages, Aug. 23, 2013.

Nederlandsch Octrooibureau, "Comparative Analysis of AONs for inducing the skipping of exon 53 from the dystrophin gene in human control muscle cells," EP1619249, 3 pages, Jan. 8, 2014.

Nederlandsch Octrooibureau, Grounds of Appeal—EP1619249, 16 pages, Aug. 23, 2013.

Nederlandsch Octrooibureau, List of all submitted documents—EP1619249, 4 pages, Jan. 8, 2014.

Nederlandsch Octrooibureau, List of all submitted documents-EP1619249, 4 pages, Aug. 23, 2013.

Nederlandsch Octrooibureau, Patentee Letter in EP1619249 Opposition Appeal Proceedings, 25 pages, Jun. 10, 2014.

Nederlandsch Octrooibureau, Patentee's Letter in Response to EPO Communication regarding EP 13170245.8, 4 pages, Apr. 15, 2015.

Nederlandsch Octrooibureau, Patentee's Letter in Response to EPO Communication regarding EP 13170245.8, 5 pages, Oct. 20, 2014.

Nederlandsch Octrooibureau, Patentee's response to communication dated Jul. 29, 2009 from the Opposition Division of EPO in relation to European Patent Application (EP 05 076 770.6), Jan. 27, 2010, 41 pages.

Nederlandsch Octrooibureau, Reply to the Grounds of Appeal—EP1619249, 35 pages, Jan. 8, 2014.

Nederlandsch Octrooibureau, Response to Communication pursuant to Article 94(3) EPC, European Patent Application No. 10718717.1, Apr. 14, 2014, 3 pages.

(56) References Cited

OTHER PUBLICATIONS

Nederlandsch Octrooibureau, Response to Communication pursuant to Rule 161 (2) and Rule 162 EPC, European Patent Application No. 10718717.1, Jun. 4, 2012, 3 pages.
Nederlandsch Octrooibureau, Sequence of Exon 45, Putative SES Fragments and Oligonucleotides—EP1619249, 1 page, Aug. 23, 2013.
Nederlandsch Octrooibureau, Sequence of Exon 46, Putative SES Fragments and Oligonucleotides—EP1619249, 1 page, Aug. 23, 2013.
Nederlandsch Octrooibureau, Sequence of Exon 53, putative SES fragments and oligonucleotides-EP1619249, D75, 1 page, Aug. 23, 2013.
Nederlandsch Octrooibureau, Sequence of Exon 53, putative SES fragments and oligonucleotides further comprising oligonucleotides of WO 2006/000057, EP1619249, D86, 1 page, Jan. 8, 2014.
Nelie Zurcher Zeitung AG, "New Treatment Approach to Rare Muscle Disease," 4 pages, Jan. 9, 2008 (with English Translation).
Nelson et al., "The Properties of Nucleotide Bases Affect the Three-Dimensional Structure of Nucleic Acids," Lehninger Principles of Biochemistry, Third Edition, p. 331, 2000.
Nishio, H., et al., "Identification of a Novel First Exon in the Human Dystrophin Gene and of a New Promoter Located More Than 500 Kb Upstream of the Nearest Known Promoter," The Journal of Clinical Investigation, 1994, vol. 94 (3), pp. 1037-1042.
Opalinska, J.B., et al., "Nucleic-Acid Therapeutics: Basic Principles and Recent Applications," Nature Reviews. Drug Discovery, Jul. 2002, vol. 1 (7), pp. 503-514.
O'Shaughnessy, J., et al., "Superior Survival With Capecitabine Plus Docetaxel Combination Therapy in Anthracycline-Pretreated Patients With Advanced Breast Cancer: Phase 111 Trial Results," Journal of Clinical Oncology, 2002, vol. 20 (12), pp. 2812-2823.
Pasternak et al., "A chemical synthesis of LNA-2, 6-diaminopurine riboside, and the influence of 2'-O-methyl-2, 6-diaminopurine and LNA-2, 6-diaminopurine ribosides on the thermodynamic properties of 2'-O-methyl RNA/RNA heteroduplexes," Nucleic Acids Research, vol. 35, No. 12, pp. 4055-4063, 2007.
Patel, K., et al., "The Function of Myostatin and Strategies of Myostatin Blockade-New Hope for Therapies Aimed at Promoting Growth of Skeletal Muscle," Neuromuscular Disorders, 2005, vol. 15 (2), pp. 117-126.
Patent Trial and Appeal Board, Declaration - 37 C.F.R., §41.203(b), 7 pages, entered Jul. 18, 2014.
Patent Trial and Appeal Board, *University of Western Australia* (U.S. Pat. No. 8,455,636) v. *Academisch Ziekenhuis Leiden* (U.S. Appl. No. 11/233,495), Decision—Motions—37 C.F.R. § 41.125(a), 53 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Decision—Motions—37 C.F.R. § 41.125(a) (Substitute), 53 pages, entered May 12, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Errata, filed May 23, 2016, 2 pages [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Judgment—Motions—37 C.F.R. § 41.127, 3 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Redeclaration—37 C.F.R. § 41.203(c), 2 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495); *University of Western Australia* (U.S. Pat. Nos. 7,960,541 and 7,807,816) v. *Academisch Ziekenhuis Leiden* (U.S. Appl. No. 13/550,210), Order—Oral Argument—37 C.F.R. § 41.124, 2 pages, entered Mar. 29, 2016 [Patent Interference Nos. 106,007 (RES) and 106,008 (RES)].
Patent Trial and Appeal Board, *University of Western Australia* (U.S. Pat. No. 8,455,636) v. *Academisch Ziekenhuis Leiden* (U.S. Appl. No. 11/233,495), Withdrawal and Reissue of Decision on Motions, 2 pages, entered May 12, 2016 [Patent Interference No. 106,007 (RES)].
Patent Trial and Appeal Board, *University of Western Australia* (U.S. Pat. No. 8,486,907) v. *Academisch Ziekenhuis Leiden* (U.S. Appl. No. 14/198,992), Decision—Priority—37 CFR § 41.125(a), 18 pages, entered Sep. 29, 2015 [Patent Interference No. 106,013 (RES)].
Patent Trial and Appeal Board, *University of Western Australia* (U.S. Pat. No. 8,486,907) v. *Academisch Ziekenhuis Leiden* (U.S. Appl. No. 14/198,992), Judgment- 37 CFR § 41.127, 2 pages, entered Sep. 29, 2015 [Patent Interference No. 106,013 (RES)].
Patent Trial and Appeal Board, *University of Western Australia* (U.S. Pat. No. 8,486,907) v. *Academisch Ziekenhuis Leiden* (U.S. Appl. No. 14/198,992), Order to Show Cause—37 C.F.R. § 41.104(a), 3 pages, Jun. 22, 2015 [Patent Interference No. 106,013 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Declaration 37 C.F.R. § 41.203(b), entered Jul. 24, 2014, 7 pages [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Order—Motion Times—37 CFR §41.104(C), entered Jul. 24, 2014, 6 pages [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Decision—Motions—37 C.F.R. § 41.125(a), 20 pages, Sep. 20, 2016 [Patent Interference No. 106,008 (RES)].
Patent Trial and Appeal Board, *University of Western Australia* (U.S. Pat. Nos. 7,960,541 and 7,807,816) v. *Academisch Ziekenhuis Leiden* (U.S. Appl. No. 13/550,210), Judgment—Motions—37 C.F.R. § 41.127, entered Sep. 20, 2016, 3 pages [Patent Interference No. 106,008 (RES)].
Patent Trial and Appeal Board, *University of Western Australia* (U.S. Pat. No. 8,486,907) v. *Academisch Ziekenhuis Leiden* (U.S. Appl. No. 14/198,992), Decision—Motions—37 C.F.R. § 41.125(a), 12 pages, Jun. 22, 2015 [Patent Interference No. 106,013 (RES)].
Peterson, TC., et al., "Selective Down-Regulation of c-jun Gene Expression by Pentoxifylline and c-jun Antisense Interrupts Platelet-Derived Growth Factor Signaling: Pentoxifylline Inhibits Phosphorylation of c-Jun on Serine 73," Molecular Pharmacology, 2002, vol. 61 (6), pp. 1476-1488.
Phillips, M.I., "Antisense Inhibition and Adeno-Associated Viral Vector Delivery for Reducing Hypertension," Hypertension, 1997, vol. 29 (1 Pt 2), pp. 177-187.
Politano, L., et al., "Gentamicin Administration in Duchenne Patients With Premature Stop Codon. Preliminary Results," Acta Myologica, 2003, vol. 22 (1), pp. 15-21.
Popplewell, L.J., et al., "Design of phosphorodiamidate morpholino oligomers (PMOs) for the Induction of exon skipping of the human DMD gene," (Abstract), Human Gene Therapy, 19 (10), Oct. 2008.
Popplewell, L.J., et al., "Design of Phosphorodiamidate Morpholino Oligomers (PMOs) for the Induction of Exon Skipping of the Human DMD Gene," Molecular Therapy, Mar. 2009, vol. 17 (3), pp. 554-561 (with attached Supplemental data, 1 page).
Popplewell, L.J., et al., Poster of "Design of Phosphorodiamidate Morpholino Oligomers (PMOs) For the Induction of Exon Skipping of the Human DMD Gene," 5th Annual Conference of the British Society for Gene & Cell Therapy, Apr. 7-9, 2008, 1 page.
Popplewell, L.J., Information Disclosure Statement for U.S. Appl. No. 14/045,841, filed Sep. 1, 2015, 3 pages, (attached non-patent literature document, 1 page).
Pramono, Z. A., et al., "Induction of Exon Skipping of the Dystrophin Transcript in Lymphoblastoid Cells by Transfecting an Antisense

(56) References Cited

OTHER PUBLICATIONS

Oligodeoxynucleotide Complementary to an Exon Recognition Sequence," Biochemical and Biophysical Research Communications, 1996, vol. 226 (2), pp. 445-449.

Radley, H.G., et al., "Duchenne Muscular Dystrophy: Focus on Pharmaceutical and Nutritional Interventions," The International Journal of Biochemistry & Cell Biology, 2007, vol. 39 (3), pp. 469-477.

Rando, T.A., "Oligonucleotide-Mediated Gene Therapy for Muscular Dystrophies," Neuromuscular Disorders, 2002, vol. 12 (Suppl 1), pp. S55-S60.

Redorbit News, "LUMC and Prosensa Report Positive Results of DMD Study," Dec. 28, 2007, 1 page.

Reitter, B., "Deflazacort vs. Prednisone in Duchenne Muscular Dystrophy: Trends of an Ongoing Study," Brain & Development, 1995, vol. 17 Suppl, pp. 39-43.

Reuser, A. J., et al., "Uptake and Stability of Human and Bovine Acid a-Glucosidase in Cultured Fibroblasts and Skeletal Muscle Cells from Glycogenosis Type 11 Patients," Experimental Cell Research, 1984, vol. 155 (1), pp. 178-189.

Rhodes, J., "Biomarin Bulks Up," Biocentury, pp. 6-8, Dec. 8, 2014.

Rigo, F., et al., "Antisense Oligonucleotide-Based Therapies for Diseases Caused by pre- mRNA Processing Defects," Advances in Experimental Medicine and Biology, 2014, vol. 825, pp. 303-352.

Roberts, R.G., et al., "Direct Detection of Dystrophin Gene Rearrangements by Analysis of Dystrophin mRNA in Peripheral Blood Lymphocytes," American Journal of Human Genetics, 1991, vol. 49 (2), pp. 298-310.

Roberts, R.G., et al., "Direct Diagnosis of Carriers of Duchenne and Becker Muscular Dystrophy by Amplification of Lymphocyte RNA," Lancet, 1990, vol. 336 (8730), pp. 1523-1526.

Roberts, R.G., et al., "Exon Structure of the Human Dystrophin Gene," Genomics, 1993, vol. 16 (2), pp. 536-538.

Roberts, R.G., et al., "Searching for the 1 in 2,400,000: A Review of Dystrophin Gene Point Mutations," Human Mutation, 1994, vol. 4 (1), pp. 1-11.

Rolland, J.F., et al., "Overactivity of Exercise-Sensitive Cation Channels and their Impaired Modulation by IGF-1 In mdx Native Muscle Fibers: Beneficial Effect of Pentoxifylline," Neurobiology of Disease, 2006, vol. 24 (3), pp. 466-474.

Rosen, G., et al., "Combination Chemotherapy and Radiation Therapy in the Treatment of Metastatic Osteogenic Sarcoma," Cancer, 1975, vol. 35 (3), pp. 622-630.

Sah, D.W., et al., "Oligonucleotide Therapeutic Approaches for Huntington Disease," The Journal of Clinical Investigation, Feb. 2011, vol. 121 (2), pp. 500-507.

Samoylova, T., et al., "Elucidation of Muscle-Binding Peptides by Phage Display Screening," Muscle & Nerve, Apr. 1999, vol. 22 (4), pp. 460-466.

Sarepta Therapeutics Inc., Notice of Opposition to European patent EP 2636741 81, 72 pages, Jan. 27, 2017.

Sarepta Therapeutics, Inc., "Sarepta Therapeutics and University of Western Australia Announce Exclusive Worldwide Licensing Agreement for Exon-Skipping Program in Duchenne Muscular Dystrophy," News Release, EP1619249, 3 pages, Apr. 2013.

Sarepta Therapeutics, Inc., Third party observations pursuant to Article 115 EPC and Rule 114 EPC against European patent application EP 10718717.1, Oct. 16, 2015, 19 pages.

Scanlon, K. J., "Anti-Genes: siRNA, Ribozymes and Antisense," Current Pharmaceutical Biotechnology, 2004, vol. 5(5), pp. 415-420.

Schnell, F., "Declaration of Dr. Fred Schnell In Support of Appeal of the Opposition Division's Decision to Maintain EP-1619249 in amended form," 6 pages, Jan. 8, 2014.

Segalat, L., et al., "CAPON Expression in Skeletal Muscle is Regulated by Position, Repair, NOS Activity, and Dystrophy," Experimental Cell Research, 2005, vol. 302 (2), pp. 170-179.

Sertic, J., et al., "Deletion Screening of the Duchenne/Becker Muscular Dystrophy Gene in Croatian Population," Collegium Antropologicum, 1997, vol. 21 (1), pp. 151-156.

Shapiro, M.B., et al., "RNA Splice Junctions of Different Classes of Eukaryotes: Sequence Statistics and Functional Implications in Gene Expression," Nucleic Acids Research, 1987, vol. 15 (17), pp. 7155-7174.

Sherratt, T.G., et al., "Exon Skipping and Translation in Patients with Frameshift Deletions in the Dystrophin Gene," American Journal of Human Genetics, 1993, vol. 53 (5), pp. 1007-1015.

Shiga, N., et al., "Disruption of the Splicing Enhancer Sequence within Exon 27 of the Dystrophin Gene by a Nonsense Mutation Induces Partial Skipping of the Exon and is Responsible for Becker Muscular Dystrophy," The Journal of Clinical Investigation, Nov. 1997, vol. 100 (9), pp. 2204-2210.

Simoes-Wust, A.P., et al., "bcl-xL Antisense Treatment Induces Apoptosis in Breast Carcinoma Cells," International Journal of Cancer, 2000, vol. 87 (4), pp. 582-590.

Singh, V., et al., "Proportion and Pattern of Dystrophin Gene Deletions in North Indian Duchenne and Becker Muscular Dystrophy Patients," Human Genetics, vol. 99 (2), pp. 206-208, 1997.

Sironi, M., et al., "The Dystrophin Gene is Alternatively Spliced Throughout its Coding Sequence," FEBS Letters, 2002, vol. 517 (1-3), pp. 163-166.

Smith, B.F., et al., "Muscle-specific Peptide #5," XP-002442550, 1 pages, Mar. 23, 1999.

Sontheimer, E., Second Declaration of Erik Sontheimer, PhD., 44 pages, Dec. 23, 2014 [Patent Interference No. 106,008 (RES)].

Sontheimer, E.J., *University of Western Australia* (U.S. Pat. Nos. 7,960,541 and 7,807,816) v. *Academisch Ziekenhuis Leiden* (U.S. Appl. No. 13/550,210), 3rd Declaration of Erik J. Sontheimer, PhD. 123 pages, filed Feb. 17, 2015 [Patent Interference No. 106,007 (RES)].

Sontheimer, Erik, Declaration of Erik Sontheimer, PhD., 112 pages, Nov. 17, 2014 [Patent Interference No. 106,008 (RES)].

Spitali, P., et al., "Exon Skipping-Mediated Dystrophin Reading Frame Restoration for Small Mutations," Human Mutation, vol. 30 (11), pp. 1527-1534, 2009.

Squires, K.E., "An Introduction to Nucleoside and Nucleotide Analogues," Antiviral Therapy, 6 (Suppl. 3), pp. 1-14, 2001.

Sterrenburg, E., et al., "Gene Expression Profiling Highlights Defective Myogenesis in DMD Patients and a Possible Role for Bone Morphogenetic Protein 4," Neurobiology of Disease, vol. 23 (1), pp. 228-236, 2006.

Summerton, J., "Morpholino Antisense Oligomers: The Case for an RNase H-lndependent Structural Type," 1999, vol. 1489 (1), pp. 141-158.

Summerton, J., et al., "Morpholino Antisense Oligomers: Design, Preparation, and Properties," Antisense & Nucleic Acid Drug Development, 1997, vol. 7 (3), pp. 187-195.

Surono, A, et al., "Chimeric RNA/Ethylene-Bridged Nucleic Acids Promote Dystrophin Expression in Myocytes of Duchenne Muscular Dystrophy by Inducing Skipping of the Nonsense Mutation-Encoding Exon," Human Gene Therapy, 2004, vol. 15 (8), pp. 749-757.

Surono, A, et al., "Six Novel Transcripts that Remove a Huge Intron Ranging from 250 to 800 kb are Produced by Alternative Splicing of the 5' Region of the Dystrophin Gene in Human Skeletal Muscle," Biochemical and Biophysical Research Communications, 1997, vol. 239 (3), pp. 895-899.

Suter, D., et al., "Double-Target Antisense U7 snRNAs Promote Efficient Skipping of an Aberrant Exon in Three Human β-Thalassemic Mutations," Human Molecular Genetics, 1999, vol. 8 (13), pp. 2415-2423.

Suwanmanee, T., et al., "Restoration of Human β-Globin Gene Expression in Murine and Human IVS2-654 Thalassemic Erythroid Cells by Free Uptake of Antisense Oligonucleotides," Molecular Pharmacology, 2002, vol. 62 (3), pp. 545-553.

Takeshima et al., Mutation spectrum of the dystrophin gene in 442 Duchenne/Becker muscular dystrophy cases from one Japanese referral center, 2010, Journal of Human Genetics, vol. 55, pp. 379-388.

Takeshima, Y., et al., "Basic Research for Treatment of Duchene Muscular Dystrophy Using Induction of Exon Skipping by Means of Antisense Oligo DNA: Effect of in Vivo Administration in

(56) References Cited

OTHER PUBLICATIONS

Mice,",, Journal of Japanese Society for Inherited Metabolic Diseases, 1999, vol. 15 (2), 6 pages (with English Translation).
Takeshima, Y., et al., "Expression of Dystrophin Protein in Cultured Duchenne Muscular Dystrophy Cells by Exon Skipping Induced by Antisense Oligonucleotide", The 44th Annual Meeting of the Japan Society of Human Genetics, 8 pages, Nov. 17-19, 1999 (English Translation).
Takeshima, Y., et al., "Intravenous Infusion of an Antisense Oligonucleotide Results in Exon Skipping in Muscle Dystrophin mRNA of Duchenne Muscular Dystrophy," Pediatric Research, 2006, vol. 59 (5), pp. 690-694.
Takeshima, Y., et al., "Modulation of In Vitro Splicing of the Upstream Intron by Modifying an Intra-Exon Sequence Which is Deleted from the Dystrophin Gene in Dystrophin Kobe," The Journal of Clinical Investigation, Feb. 1995, vol. 95 (2), pp. 515-520.
Takeshima, Y., et al., "Oligonucleotides Against a Splicing Enhancer Sequence Led to Dystrophin Production In Muscle Cells from a Duchenne Muscular Dystrophy Patient," Brain& Development, 2001, vol. 23 (8), pp. 788-790.
Tanaka, K., et al., "Polypurine Sequences within a Downstream Exon Function as a Splicing Enhancer," Molecular and Cellular Biology, 1994, vol. 14 (2), pp. 1347-1354.
Taneja, K.L., "Localization of Trinucleotide Repeat Sequences in Myotonic Dytrophy Cells Using a Single Fluorochrome-Labeled PNA Probe," BioTechniques, vol. 24, No. 3, pp. 472-476, Mar. 1998.
Tennyson, C.N., et al., "The Human Dystrophin Gene Requires 16 Hours to be Transcribed and is Cotranscriptionally Spliced," Nature Genetics, vol. 9 (2), pp. 184-190, 1995.
Thanh, L.T., et al., "Characterization of Revertant Muscle Fibers in Duchenne Muscular Dystrophy, Using Exon-Specific Monoclonal Antibodies against Dystrophin," American Journal of Human Genetics, 1995, vol. 56 (3), pp. 725-731.
Thomsen, R., et al., "Dramatically improved RNA in situ hybridization signals using LNA- modified probes," RNA, vol. 11, pp. 1745-1748, 2005.
Thomson Reuters Integrity, "Dystrophin gene (DMD) expression inhibitor PR0-051," Prous Integrity, XP002677703, Mar. 8, 2012.
Tian, H., et al., "Selection of Novel Exon Recognition Elements from a Pool of Random Sequences," Molecular and Cellular Biology, Nov. 1995, vol. 15 (11), pp. 6291-6298.
TREAT-NMD, Neuromuscular Network, Newsletter No. 24, 6 pages, Jan. 11, 2008.
Tsuchida, K., "The Role of Myostatin and Bone Morphogenetic Proteins in Muscular Disorders," Expert Opinion of Biological Therapy, 2006, vol. 6 (2), pp. 147-154.
U.S. Food and Drug Administration (FDA) Briefing Document to the Peripheral and Central Nervous System Drugs Advisory Committee Meeting, Nov. 24, 2015,NDA 206031, Drisapersen.
United States Court of Appeals for the Federal Circuit, Brief of Appellant University of Western Australia, 223 pages, dated Jan. 23, 2017 [Interference No. 106,013).
United States Court of Appeals for the Federal Circuit, Notice Forwarding Certified List, Appeal No. 2016-2262, Aug. 5, 2016, 18 pages [Patent Interference No. 106,007 (RES)].
United States Court of Appeals for the Federal Circuit, Principal Brief of Appellant Academisch Ziekenhuis Leiden, 135 pages, filed Jan. 23, 2017 [Interference Patent No. 106,007].
United States Court of Appeals for the Federal Circuit, Principal Brief of Appellant Academisch Ziekenhuis Leiden, 80 pages, filed Jan. 23, 2017 [Patent Interference No. 106,008].
United States Patent and Trademark Office, Office Action for U.S. Appl. No. 11/233,495, filed Jun. 25, 2009, 11 pages.
United States Patent and Trademark Office, Office Action for U.S. Appl. No. 10/395,031, 11 pages, dated Apr. 2, 2009.
United States Patent and Trademark Office, Office Action for U.S. Appl. No. 10/395,031, 15 pages, dated Nov. 30, 2006.
United States Patent and Trademark Office, Office Action for U.S. Appl. No. 10/395,031, 16 pages, dated Feb. 6, 2006.
United States Patent and Trademark Office, Office Action for U.S. Appl. No. 10/395,031, 20 pages, dated Aug. 23, 2007.
United States Patent and Trademark Office, Office Action for U.S. Appl. No. 10/395,031, 20 pages, dated Jul. 8, 2005.
United States Patent and Trademark Office, Office Action for U.S. Appl. No. 10/395,031, 29 pages, dated May 30, 2008.
United States Patent and Trademark Office, Office Action for U.S. Appl. No. 10/395,031, 7 pages, dated Oct. 16, 2009.
United States Patent and Trademark Office, Office Action for U.S. Appl. No. 11/233,495, 14 pages, dated Dec. 1, 2008.
United States Patent and Trademark Office, Office Action for U.S. Appl. No. 11/233,507, 12 pages, dated Mar. 19, 2008.
United States Patent and Trademark Office, Office Action for U.S. Appl. No. 11/233,507, 16 pages, dated Jun. 15, 2007.
United States Patent and Trademark Office, Office Action for U.S. Appl. No. 11/233,507, 17 pages, dated May 29, 2009.
United States Patent and Trademark Office, Office Action for U.S. Appl. No. 11/233,507, 17 pages, dated Nov. 12, 2008.
United States Patent and Trademark Office, Office Action for U.S. Appl. No. 11/982,285, 16 pages, dated May 4, 2009.
United States Patent and Trademark Office, Office Action for U.S. Appl. No. 11/982,285, 22 pages, dated Sep. 18, 2009.
University of Western Australia, *Academisch Ziekenhuis Leiden* v. *University of Western Australia*, "Brief of Appellee University of Western Australia," 76 pages, Mar. 6, 2017 [Interference No. 106,007].
University of Western Australia, *Academisch Ziekenhuis Leiden* v. *University of Western Australia*, "Response Brief of Appellee University of Western Australia," 51 pages, Mar. 6, 2017 [Interference No. 106,008].
University of Western Australia, *Academisch Ziekenhuis Leiden* v. *University of Western Australia, University of Western Ausualia* v. *Academisch Ziekenhuis Leiden*, "Reply of University of Western Australia in Support of It's Motion to Designate as Companion Cases To Extend the Briefing Schedules," 8 pages, Nov. 21, 2016 [Interference Nos. 106,007, 106,008, 106,013].
University of Western Australia, Motion of Appellant University of Western Australia to Stay Appeal Pending Appeals in Two Related Interferences, Document 4-1, 7 pages, entered May 6, 2016 [Patent Interference No. 106,013] [Case: 16-1937].
University of Western Australia, Reply Brief of Appellant University of Western Australia, US Court of Appeals for the Federal Circuit, Case: 16-1937, 16-2086, 40 pages, Apr. 25, 2017.
University of Western Australia, *University of Western Australia* (U.S. Pat. No. 8,455,636) v. *Academisch Ziekenhuis Leiden* (U.S. Appl. No. 11/233,495), University of Western Australia Exhibit List, 10 pages, filed Apr. 10, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Exhibit List, 10 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Exhibit List as of Feb. 17, 2015, 8 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Miscellaneous Motion 4 (to exclude evidence), 21 pages, filed Apr. 10, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 1 (For Judgment Under 35 U.S.C. § 112(a)), 40 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 2

(56) References Cited

OTHER PUBLICATIONS (For Judgment Under 35 U.S.C. § 112(b)), 34 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Motion 3 (Requesting an Additional Interference Between UWA U.S. Pat. No. 8,455,636 and Academisch Ziekenhuis Leiden's U.S. Appl. No. 14/248,279), 36 pages, filed Nov. 18, 2014 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 1 (to AZL Opposition 1), 28 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 2 (to AZL Opposition 2), 22 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Reply 3 (to Institute an Interference), 17 pages, filed Apr. 3, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Request for Oral Argument, 4 pages, filed Apr. 10, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233.495), University of Western Australia List of Proposed Motions, 7 pages, filed Sep. 10, 2014 [Patent Interference No. 106,007 (RES)].
University of Western Australia, *University of Western Australia* (U.S. Pat. No. 8,486,907) v. *Academisch Ziekenhuis Leiden* (U.S. Appl. No. 14/198,992), University of Western Australia Motion 1 (To Maintain Interference Between UWA U.S. Pat. No. 8,486,907 and Academisch Ziekenhuis Leiden's U.S. Appl. No. 14/198,992), 45 pages, filed Nov. 18, 2014 [Patent Interference No. 106,013 (RES)].
University of Western Australia, *University of Western Australia* (U.S. Pat. No. 8,486,907) v. *Academisch Ziekenhuis Leiden* (U.S. Appl. No. 14/198,992), University of Western Australia Response to Order to Show Cause, 28 pages, filed Jul. 20, 2015 [Patent Interference No. 106,013 (RES)].
University of Western Australia, *University of Western Australia* (U.S. Pat. No. 8,455,636) v. *Academisch Ziekenhuis Leiden* (U.S. Appl. No. 11/233,495), University of Western Ausualia Objections (to Opposition Evidence), 15 pages, filed Feb. 24, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 1 (Regarding Patentability Under 35 U.S.C. § 102/103), 38 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 2 (to Retain UWA's Benefit of AU 2004903474), 37 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 3 (Regarding Patentability Under 35 U.S. C.§ 101), 22 pages, filed Feb. 17, 2015 [Patent Interference No. 106,007 (RES)].
University of Western Australia, *University of Western Australia* (U.S. Pat. No. 8,455,636) v. *Academisch Ziekenhuis Leiden* (U.S. Appl. No. 11/233,495), University of Western Australia Opposition 4 (to deny entry of AZL's Proposed New Claims 104 and 105), 36 pages, filed Feb. 17, 2015 [Patent Interference No. 106,007 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List as of Apr. 10, 2015, 10 pages, filed Apr. 10, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List as of Apr. 3, 2015, 10 pages, filed Apr. 3, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Exhibit List as of Feb. 17, 2015, 8 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Ausualia Miscellaneous Motion 4 (to exclude evidence), 21 pages, filed Apr. 10, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Ausualia Opposition 1 (Regarding Patentability Under 35 U.S.C. § 102/103), 39 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Ausualia Opposition 2 (To Retain UWA's Benefit of AU 2004903474), 31 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Ausualia Opposition 3 (Regarding Patentability Under 35 U.S.C. § 101), 22 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Ausualia Opposition 4 (To deny entry of AZL's Proposed New Claims 30 and 31), 36 pages, filed Feb. 17, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 1 (to AZL Opposition 1), 28 pages, filed Apr. 3, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 2 (to AZL Opposition 2), 22 pages, filed Apr. 3, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Reply 3. (for judgment under 35 U.S.C. § 135(b)), 19 pages, filed Apr. 3, 2015 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Ausualia Request for Oral Argument, 4 pages, filed Apr. 10, 2015 [Patent Interference No. 106,008 (RES)].
University of Western Australia, *University of Western Australia* (U.S. Pat. Nos. 7,960,541, 7,807,816) v. *Academisch Ziekenhuis Leiden* (U.S. Appl. No. 13/550,210), University of Western Australia List of Proposed Motions, 6 pages, filed Sep. 10, 2014 [Patent Interference No. 106,008 (RES)].
University of Western Australia, *University of Western Australia* (U.S. Pat. No.s 7,960,541 and 7,807,816) v. *Academisch Ziekenhuis Leiden* (U.S. Appl. No. 13/550,210), University of Western Austra-

(56) References Cited

OTHER PUBLICATIONS lia Motion 1 (for Judgment Under 3 5 U.S.C. § 112(a)), 38 pages, filed Nov. 18, 2014 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 2 (for Judgment Under 35 U.S.C. § 112(b)), 32 pages, filed Nov. 18, 2014 [Patent Interference No. 106,008 (RES)].
University of Western Australia, *University of Western Australia* (U.S. Pat. Nos. 7,960,541 and 7,807,816) v. *Academisch Ziekenhuis Leiden* (U.S. Appl. No. 13/550,210), University of Western Australia Motion 3 (for judgment that Claims 11-12, 14-15, and 17-29 of U.S. Appl. No. 13/550,210 are barred under 35 U.S.C. §135(b)); 25 pages, filed Nov. 18, 2014 [Patent Interference No. 106,008].
University of Western Australia, *University of Western Australia* v. *Academisch Ziekenhuis Leiden*, Corrected Brief of Appellant University of Western Australia, 223 pages, filed Feb. 16, 2017 [Interference No. 106,013].
University of Western Australia, *University of Western Australia*, (U.S. Pat. Nos. 7,960,541 and 7,807,816) v. *Academisch Ziekenhuis Leiden* (U.S. Appl. No. 13/550,210), University of Western Ausualia Objections (to Opposition Evidence), 15 pages, filed Feb. 24, 2015 [Patent Interference No. 106,008 (RES)].
USAN Council Statement for Drisapersen.
Vandeutekom, J.C., "Declaration of Dr. JCT vanDeutekom," EP1619249, 2 pages, Aug. 1, 2013.
Van Deutekom, J.C., "Declaration of JCT van Deutekom," EP1619249, 6 pages, Jan. 7, 2014.
Van Deutekom, J.C., Declaration of Dr. Judith van Deutekom, 8 pages, EP 1 619 249, Jun. 10, 2014.
Van Deutekom, J.C., Declaration of Judith Van Deutekom, 45 pages, Feb. 17, 2015 [Patent Interference Nos. 106,007 and 106,008 (RES)].
Van Deutekom, J.C., et al., "Advances in Duchenne Muscular Dystrophy Gene Therapy," Nature Reviews Genetics, Oct. 2003, vol. 4 (10), pp. 774-783.
Van Deutekom, J.C., et al., "Antisense-induced exon skipping restores dystrophin expression in DMD patient derived muscle cells," Human Molecular Genetics, vol. 10, No. 15, pp. 1547-1554, 2001.
Vandeutekom, J.C., et al., "Local Dystrophin Restoration with Antisense Oligonucleotide PRO051," The New England Journal of Medicine, 2007, vol. 357 (26), pp. 2677-2686.
Vandeutekom, J.C., Transcript of deposition testimony of Dr. Judith van Deutekom taken on Mar. 11, 2015, pertaining to Patent Interference No. 106,007 (RES); relating to U.S. Pat. No. 8,455,636, 169 pages.
Van Ommen, G. J., et al., "The Therapeutic Potential of Antisense-Mediated Exon Skipping," Current Opinion in Molecular Therapeutics, 2008, vol. 10 (2), pp. 140-149.
Van Vliet, L., et al., "Assessment of the Feasibility of Exon 45-55 Multiexon Skipping for Duchenne Muscular Dystrophy," BMC Medical Genetics, 2008, vol. 9 (105), 7 pages.
Varani, G., et al., "The G-U Wobble Base Pair. A Fundamental Building Block of RNA Structure Crucial to RNA Function in Diverse Biological Systems," EMBO Reports, 2000, vol. 1 (1), pp. 18-23.
Verhaart, I.E., et al., "Prednisolone Treatment Does Not Interfere with 2'-O-Methyl Phosphorothioate Antisense-Mediated Exon Skipping in Duchenne Muscular Dystrophy," Human Gene Therapy, Mar. 2012, vol. 23 (3), pp. 262-273.
Verreaul T, M., et al., "Gene Silencing in the Development of Personalized Cancer Treatment: The Targets, the Agents and the Delivery Systems," Current Gene Therapy, 2006, vol. 6 (4), pp. 505-533.
Vickers, T. A., et al., "Efficient Reduction of Target RNAs by Small Interfering RNA and RNase H-dependent Antisense Agents. A Comparative Analysis," The Journal of Biological Chemistry, Feb. 2003, vol. 278 (9), pp. 7108-7118.

Wang, B., et al., "Adeno-Associated Virus Vector Carrying Human Minidystrophin Genes Effectively Ameliorates Muscular Dystrophy in mdx Mouse Model," Proceedings of the National Academy of Sciences of the United States of America, 2000, vol. 97 (25), pp. 13714-13719.
Wang, Z., et al., "Sustained AAV-Mediated Dystrophin Expression in a Canine Model of Duchenne Muscular Dystrophy with a Brief Course of Immunosuppression," Molecular Therapy, vol. 15 (6), pp. 1160-1166, Jun. 2007.
Watakabe, A., et al., "The Role of Exon Sequences in Splice Site Selection," Genes & Development, 1993, vol. 7 (3), pp. 407-418.
Watkins, N.E., et al., "Nearest-Neighbor Thermodynamics of Deoxyinosine Pairs in DNA Duplexes," Nucleic Acids Research, vol. 33 (19), pp. 6258-6267, 2005.
Wehling-Henricks et al., "Prednisolone decreases cellular adhesion molecules required for inflammatory cell infiltration in dystrophin-deficient skeletal muscle," Neuromuscul. Disord. 14(8-9):483-490 (2004).
Weiler, T., et al., "Identical Mutation in Patients with Limb Girdle Muscular Dystrophy Type 28 or Miyoshi Myopathy Suggests a Role for Modifier Gene(s)," Human Molecular Genetics, 1999, vol. 8 (5), pp. 871-877.
Weisbart, R.H., et al., "Cell Type Specific Targeted Intracellular Delivery Into Muscle of a Monoclonal Antibody that Binds Myosin 11b," Molecular Immunology, 2003, vol. 39 (13), pp. 783-789 (Abstract).
Wells, K.E., et al., "Enhanced in Vivo Delivery of Antisense Oligonucleotides to Restore Dystrophin Expression in Adult mdx Mouse Muscle," FEBS Letters, 2003, vol. 552 (2-3), pp. 145-149.
Wenk, J., et al., "Quantitation of Mr 46000 and Mr 300000 Mannose 6-Phosphate Receptors in Human Cells and Tissues," Biochemistry International, 1991, vol. 23 (4), pp. 723-731 (Abstract).
Wheeler, T.M., et al., "Reversal of RNA Dominance by Displacement of Protein Sequestered on Triplet Repeat RNA," Science, vol. 325, pp. 336-339, Jul. 2009.
Wheway, J.M., et al., "The Dystrophin Lymphocyte Promoter Revisited: 4.5-Megabase Intron, or Artefact?," Neuromuscular Disorders, 2003, vol. 13 (1), pp. 17-20.
Wilton, S., Declaration of Dr. Steve Wilton In Support of Appeal of Opposition Decision to Maintain EP 1619249, dated Aug. 21, 2013, 25 pages.
Wilton, S., et al., Excerpts from Prosecution History of Wilton et al., (U.S. Appl. No. 13/902,376), including an Express Abandonment, 67 pages, filing date of May 24, 2013.
Wilton, S., et al., Excerpts from Prosecution History of Wilton et al. (U.S. Appl. No. 14/178,059), including Preliminary Amendment and Request to Provoke an Interference, 97 pages, 2014.
Wilton, S.D., et al., "Antisense Oligonucleotide-induced Exon Skipping Across the Human Dystrophin Gene Transcript," Molecular Therapy: The Journal of the American Society of Gene Therapy, Jul. 2007, vol. 15 (7), pp. 1288-1296.
Wilton, S.D., et al., "Antisense Oligonucleotides, Exon Skipping and the Dystrophin Gene Transcript.," Acta Myologica, 2005, vol. 24, pp. 222-229.
Wilton, S.D., et al., "Specific Removal of the Nonsense Mutation from the mdx Dystrophin mRNA Using Antisense Oligonucleotides," Neuromuscular Disorders, 1999, vol. 9 (5), pp. 330-338.
Wood, Matthew J. A.,*University of Western Australia* (U.S. Pat. No. 8,455,636) v. *Academisch Ziekenhuis Leiden* (U.S. Appl. No. 14/198,992) [Patent Interference No. 106,007 (RES)] and University of Western Australia (Patent Nos. 7,960,541 and 7,807,816) v. Academisch Ziekenhuis Leiden (U.S. Appl. No. 14/198,992) [Patent Interference No. 106,008 (RES)], *University of Western Australia* (U.S. Pat. No. 8,486,907) v. *Academisch Ziekenhuis Leiden* (U.S. Appl. No. 14/198,992) [Patent Interference No. 106,013 (RES)], Second Declaration of Matthew J. A. Wood, M.D., D. Phil., 78 pages, filed Feb. 17, 2015.
Wood, Matthew J.A., *University of Western Australia* (U.S. Pat. Nos. 8,455,636, 7,960,541, 7,807,816, 8,486,907) v. *Academisch Ziekenhuis Leiden* ( U.S. Appl. No. 14/198,992, U.S. Appl. No. 14/198,992, U.S. Appl. No. 14/198,992), Declaration of Matthew J.

(56) References Cited

OTHER PUBLICATIONS

A. Wood, M.D., D. Phil.—UWA Exhibit 2081, 184 pages, filed Sep. 19, 2014 [Patent Interference Nos. 106,007, 106,008, 106,113 (RES)].

Wright, H., et al., Opposition to EP 2 344 637, Sep. 24, 2015, 28 pages.

Wu, B., et al., "Targeted Skipping of Human Dystrophin Exons in Transgenic Mouse Model Systemically for Antisense Drug Development," PLoS One, vol. 6 (5), 11 pages, 2011.

Wuebbles et al., "Levels of α7 integrin and laminin-α2 are increased following prednisone treatment in the mdx mouse and GRMD dog models of Duchenne muscular dystrophy," Dis. Model. Mech. 6(5):1175-1184 (2013) (Epub Jul. 11, 2013).

Xu, L., et al., "Potential for Pharmacology of Ryanodine Receptor/Calcium Release Channels," Annals of the New York Academy of Sciences, vol. 853, pp. 130-148, Sep. 16, 1998.

Yen, L., et al., "Sequence-specific Cleavage of Huntingtin mRNA by Catalytic DNA," Annals of Neurology, 1999, vol. 46 (3), pp. 366-373.

Yilmaz-Elis, AS., et al., "Inhibition of IL-1 Signaling by Antisense Oligonucleotide-mediated Exon Skipping of IL-1 Receptor Accessory Protein (IL-1 RAcP)," Molecular Therapy-Nucleic Acids, 2013, vol. 2, e66, 8 pages.

Yin, H., et al., "Effective Exon Skipping and Restoration of Dystrophin Expression by Peptide Nucleic Acid Antisense Oligonucleotides in mdx Mice," Molecular Therapy, Jan. 2008, vol. 16 (1), pp. 38-45.

Yokota, T., et al., "Antisense Oligo-Mediated Multiple Exon Skipping in a Dog Model of Duchenne Muscular Dystrophy," Methods in Molecular Biology, vol. 709, pp. 299-312, 2011.

Yokota, T., et al., "Efficacy of Systemic Morpholino Exon-Skipping in Duchenne Dystrophy Dogs," American Neurological Association, 2009, vol. 65 (6), pp. 667-676.

Yu, M., et al., "A Hairpin Ribozyme Inhibits Expression of Diverse Strains of Human Immunodeficiency Virus Type 1," Proceedings of the National Academy of Sciences of the United States of America, 1993, vol. 90 (13), pp. 6340-6344.

Yu, R.Z., et al., "Development of an Ultrasensitive Noncompetitive Hybridization-Ligation Enzyme-Linked Immunosorbent Assay for the Determination of Phosphorothioate Oligodeoxynucleotide in Plasma," Analytical Biochemistry, vol. 304 (1), pp. 19-25, 2002.

Zhang, G., et al., "Efficient Expression of Naked DNA Delivered Intraarterially to Limb Muscles of Nonhuman Primates," Human Gene Therapy, 2001, vol. 12 (4), pp. 427-438 (Abstract).

Zhou, G.Q., et al., "Current Understanding of Dystrophin-Related Muscular Dystrophy and Therapeutic Challenges Ahead," Chinese Medical Journal, 2006, vol. 119 (16), pp. 1381-1391.

Alter et al., "Systemic delivery of morpholino oligonucleotide restores dystrophin expression bodywide and improves dystrophic pathology," Nat. Med. 12(2): 175-177 (2006).

Ito et al. "Identification of Splicing Enhancer Sequences Within Exon Sequences of Dystrophin Gene", 42nd Convention of Japanese Society for Inherited Metabolic Diseases,Kagoshima, Japan, Nov. 11-13, 1999, Journal of Japanese Society for Inherited Metabolic Diseases, 15(2): # 100, Nov. 1999.

Popplewell et al., "Design of Antisense Oligonucleotides for Exon Skipping of theHuman Dystrophin Gene", BSGT Annual Conference Abstracts, Human Gene Therapy, 19(4):402-422, #P 35, Apr. 2008.

Matsuo, "Duchenne and Becker Muscular Dystrophy: From Gene Diagnosis to Molecular Therapy", IUBMB Life, 53: 147-152, 2002.

Neue Zurcher Zeitung AG, "New Treatment Approach to Rare Muscle Disease," 4 pages, Jan. 9, 2008 (with English Translation).

Sironi et al., "Silencer elements as possible inhibitors of pseudoexon splicing", Nucleic Acids Research, 2004, vol. 32, No. 4, pp. 1783-1791.

Soret et al. Selective modification of alternative splicing by indole derivatives that target serine-arginine-rich protein splicing factors. Proc Natl Acad Sci USA 2005; 102(24):8764-9.

Graham et al. Towards a therapeutic inhibition of dystrophin exon 23 splicing in mdx mouse muscle induced by antisense oligoribonucleotides ( splicomers ): target sequence optimisation using oligonucleotide arrays. J Gene Med 2004; 6(10):1149-58.

Cartegni et al. ESEfinder: A web resource to identify exonic splicing enhancers. Nucleic Acids Res 2003; 31(13):3568-71.

Braasch et al. Locked nucleic acid (LNA): 35 fine-tuning the recognition of DNA and RNA. Chem Biol 2001; 8(1):1-7.

Braasch et al. Novel antisense and peptide nucleic acid strategies for controlling gene expression, Biochemistry 2002; 41(14):4503-10.

Elayadi et al. Application of PNA and LNA oligomers to chemotherapy. Curr Opin Investig Drugs 2001; 2(4):558-61.

Larsen et al. Antisense properties of peptide nucleic acid. Biochim Biophys Acta 1999; 1489 (1):159-66.

Wahlestedt et al. Potent and nontoxic antisense oligonucleotides containing locked nucleic acids. Proc Natl Acad Sci USA 2000; 97(10):5633-8.

Ehmsen et al., "The dystrophin-associated protein complex," J. Cell Sci. 1 15(Pt 14):2801-2803 (2002).

Yokota et al., "Optimizing exon skipping therapies for DMD," Acta Myol. 26(3): 179-184 (2007).

Karras et al. "Peptide Nucleic Acids Are Potent Modulators of Endogenous Pre-mRNA Splicing of the Murine Interleukin-5 Receptor-Alpha Chain", Biochemistry, 40(26): 7853-7859, Jul. 3, 2001.

Morita et al. "2'-O,4'-C-Ethylene-Bridged Nucleic Acids (ENA) With Nuclease-Resistance and High Affinity for RNA", Nucleic Acids Research, Suppl 1:241-242, 2001.

Yagi et al. "Chimeric RNA and 2'-O, 4'-C-Ethylene-Bridged Nucleic Acids Have Stronger Activity than Phosphorothioate Oligodeoxynucleotides in Induction of Exon 19 Skipping in Dystrophin mRNA," Oligonucleotides 14 (1):33-40, 2004.

\* cited by examiner

Screening of Exon 45 specific PS220 at Increasing
Concentrations in Human Control Myotubes Comparison of 17-mer AON45-5 vs. 25-
mer PS220 in Human Control Myotubes

SEQUENCE LISTING

<160> NUMBER OF SEQ ID NOS: 236

<210> SEQ ID NO 1
<211> LENGTH: 3685
<212> TYPE: PRT
<213> ORGANISM: homo sapiens

<400> SEQUENCE: 1

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
```

-continued

```
            180                 185                 190
Thr Gln Arg Leu Glu His Ala Phe Asn Ile Ala Arg Tyr Gln Leu Gly
            195                 200                 205
Ile Glu Lys Leu Leu Asp Pro Glu Asp Val Asp Thr Thr Tyr Pro Asp
            210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Glu Met Leu Pro Arg
            245                 250                 255
Pro Pro Lys Val Thr Lys Glu Glu His Phe Gln Leu His His Gln Met
            260                 265                 270
His Tyr Ser Gln Gln Ile Thr Val Ser Leu Ala Gln Gly Tyr Glu Arg
            275                 280                 285
Thr Ser Ser Pro Lys Pro Arg Phe Lys Ser Tyr Ala Tyr Thr Gln Ala
            290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
            325                 330                 335
Ser Glu Val Asn Leu Asp Arg Tyr Gln Thr Ala Leu Glu Glu Val Leu
            340                 345                 350
Ser Trp Leu Leu Ser Ala Glu Asp Thr Leu Gln Ala Gln Gly Glu Ile
            355                 360                 365
Ser Asn Asp Val Glu Val Val Lys Asp Gln Phe His Thr His Glu Gly
            370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
            405                 410                 415
Glu Thr Glu Val Gln Glu Gln Met Asn Leu Leu Asn Ser Arg Trp Glu
            420                 425                 430
Cys Leu Arg Val Ala Ser Met Glu Lys Gln Ser Asn Leu His Arg Val
            435                 440                 445
Leu Met Asp Leu Gln Asn Gln Lys Leu Lys Glu Leu Asn Asp Trp Leu
450                 455                 460
Thr Lys Thr Glu Glu Arg Thr Arg Lys Met Glu Glu Pro Leu Gly
465                 470                 475                 480
Pro Asp Leu Glu Asp Leu Lys Arg Gln Val Gln Gln His Lys Val Leu
            485                 490                 495
Gln Glu Asp Leu Glu Gln Glu Gln Val Arg Val Asn Ser Leu Thr His
            500                 505                 510
Met Val Val Val Asp Glu Ser Ser Gly Asp His Ala Thr Ala Ala
            515                 520                 525
Leu Glu Glu Gln Leu Lys Val Leu Gly Asp Arg Trp Ala Asn Ile Cys
            530                 535                 540
Arg Trp Thr Glu Asp Arg Trp Val Leu Leu Gln Asp Ile Leu Leu Lys
545                 550                 555                 560
Trp Gln Arg Leu Thr Glu Glu Gln Cys Leu Phe Ser Ala Trp Leu Ser
            565                 570                 575
Glu Lys Glu Asp Ala Val Asn Lys Ile His Thr Thr Gly Phe Lys Asp
            580                 585                 590
Gln Asn Glu Met Leu Ser Ser Leu Gln Lys Leu Ala Val Leu Lys Ala
            595                 600                 605
```

```
Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
                660                 665                 670

Gln Pro Ser Leu Thr Gln Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
                740                 745                 750

Glu Gly Asn Phe Ser Asp Leu Lys Glu Lys Val Asn Ala Ile Glu Arg
            755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
                820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
                900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser Thr Thr Val Lys Glu Met Ser Lys
        995                 1000                1005

Lys Ala Pro Ser Glu Ile Ser Arg Lys Tyr Gln Ser Glu Phe Glu
    1010                1015                1020
```

```
Glu Ile Glu Gly Arg Trp Lys Lys Leu Ser Ser Gln Leu Val Glu
1025                1030                1035

His Cys Gln Lys Leu Glu Glu Gln Met Asn Lys Leu Arg Lys Ile
1040                1045                1050

Gln Asn His Ile Gln Thr Leu Lys Lys Trp Met Ala Glu Val Asp
1055                1060                1065

Val Phe Leu Lys Glu Glu Trp Pro Ala Leu Gly Asp Ser Glu Ile
1070                1075                1080

Leu Lys Lys Gln Leu Lys Gln Cys Arg Leu Leu Val Ser Asp Ile
1085                1090                1095

Gln Thr Ile Gln Pro Ser Leu Asn Ser Val Asn Glu Gly Gly Gln
1100                1105                1110

Lys Ile Lys Asn Glu Ala Glu Pro Glu Phe Ala Ser Arg Leu Glu
1115                1120                1125

Thr Glu Leu Lys Glu Leu Asn Thr Gln Trp Asp His Met Cys Gln
1130                1135                1140

Gln Val Tyr Ala Arg Lys Glu Ala Leu Lys Gly Gly Leu Glu Lys
1145                1150                1155

Thr Val Ser Leu Gln Lys Asp Leu Ser Glu Met His Glu Trp Met
1160                1165                1170

Thr Gln Ala Glu Glu Glu Tyr Leu Glu Arg Asp Phe Glu Tyr Lys
1175                1180                1185

Thr Pro Asp Glu Leu Gln Lys Ala Val Glu Glu Met Lys Arg Ala
1190                1195                1200

Lys Glu Glu Ala Gln Gln Lys Glu Ala Lys Val Lys Leu Leu Thr
1205                1210                1215

Glu Ser Val Asn Ser Val Ile Ala Gln Ala Pro Pro Val Ala Gln
1220                1225                1230

Glu Ala Leu Lys Lys Glu Leu Glu Thr Leu Thr Thr Asn Tyr Gln
1235                1240                1245

Trp Leu Cys Thr Arg Leu Asn Gly Lys Cys Lys Thr Leu Glu Glu
1250                1255                1260

Val Trp Ala Cys Trp His Glu Leu Leu Ser Tyr Leu Glu Lys Ala
1265                1270                1275

Asn Lys Trp Leu Asn Glu Val Glu Phe Lys Leu Lys Thr Thr Glu
1280                1285                1290

Asn Ile Pro Gly Gly Ala Glu Glu Ile Ser Glu Val Leu Asp Ser
1295                1300                1305

Leu Glu Asn Leu Met Arg His Ser Glu Asp Asn Pro Asn Gln Ile
1310                1315                1320

Arg Ile Leu Ala Gln Thr Leu Thr Asp Gly Gly Val Met Asp Glu
1325                1330                1335

Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
```

-continued

```
            1415                1420                1425
Lys His Asn Gln Gly Lys Glu Ala Ala Gln Arg Val Leu Ser Gln
    1430                1435                1440

Ile Asp Val Ala Gln Lys Lys Leu Gln Asp Val Ser Met Lys Phe
    1445                1450                1455

Arg Leu Phe Gln Lys Pro Ala Asn Phe Glu Gln Arg Leu Gln Glu
    1460                1465                1470

Ser Lys Met Ile Leu Asp Glu Val Lys Met His Leu Pro Ala Leu
    1475                1480                1485

Glu Thr Lys Ser Val Glu Gln Glu Val Val Gln Ser Gln Leu Asn
    1490                1495                1500

His Cys Val Asn Leu Tyr Lys Ser Leu Ser Glu Val Lys Ser Glu
    1505                1510                1515

Val Glu Met Val Ile Lys Thr Gly Arg Gln Ile Val Gln Lys Lys
    1520                1525                1530

Gln Thr Glu Asn Pro Lys Glu Leu Asp Glu Arg Val Thr Ala Leu
    1535                1540                1545

Lys Leu His Tyr Asn Glu Leu Gly Ala Lys Val Thr Glu Arg Lys
    1550                1555                1560

Gln Gln Leu Glu Lys Cys Leu Lys Leu Ser Arg Lys Met Arg Lys
    1565                1570                1575

Glu Met Asn Val Leu Thr Glu Trp Leu Ala Ala Thr Asp Met Glu
    1580                1585                1590

Leu Thr Lys Arg Ser Ala Val Glu Gly Met Pro Ser Asn Leu Asp
    1595                1600                1605

Ser Glu Val Ala Trp Gly Lys Ala Thr Gln Lys Glu Ile Glu Lys
    1610                1615                1620

Gln Lys Val His Leu Lys Ser Ile Thr Glu Val Gly Glu Ala Leu
    1625                1630                1635

Lys Thr Val Leu Gly Lys Lys Glu Thr Leu Val Glu Asp Lys Leu
    1640                1645                1650

Ser Leu Leu Asn Ser Asn Trp Ile Ala Val Thr Ser Arg Ala Glu
    1655                1660                1665

Glu Trp Leu Asn Leu Leu Leu Glu Tyr Gln Lys His Met Glu Thr
    1670                1675                1680

Phe Asp Gln Asn Val Asp His Ile Thr Lys Trp Ile Ile Gln Ala
    1685                1690                1695

Asp Thr Leu Leu Asp Glu Ser Glu Lys Lys Lys Pro Gln Gln Lys
    1700                1705                1710

Glu Asp Val Leu Lys Arg Leu Lys Ala Glu Leu Asn Asp Ile Arg
    1715                1720                1725

Pro Lys Val Asp Ser Thr Arg Asp Gln Ala Ala Asn Leu Met Ala
    1730                1735                1740

Asn Arg Gly Asp His Cys Arg Lys Leu Val Glu Pro Gln Ile Ser
    1745                1750                1755

Glu Leu Asn His Arg Phe Ala Ala Ile Ser His Arg Ile Lys Thr
    1760                1765                1770

Gly Lys Ala Ser Ile Pro Leu Lys Glu Leu Glu Gln Phe Asn Ser
    1775                1780                1785

Asp Ile Gln Lys Leu Leu Glu Pro Leu Glu Ala Glu Ile Gln Gln
    1790                1795                1800

Gly Val Asn Leu Lys Glu Glu Asp Phe Asn Lys Asp Met Asn Glu
    1805                1810                1815
```

Asp Asn Glu Gly Thr Val Lys Glu Leu Leu Gln Arg Gly Asp Asn
1820                1825                1830

Leu Gln Gln Arg Ile Thr Asp Glu Arg Lys Arg Glu Ile Lys
1835                1840                1845

Ile Lys Gln Gln Leu Leu Gln Thr Lys His Asn Ala Leu Lys Asp
1850                1855                1860

Leu Arg Ser Gln Arg Arg Lys Lys Ala Leu Glu Ile Ser His Gln
1865                1870                1875

Trp Tyr Gln Tyr Lys Arg Gln Ala Asp Asp Leu Leu Lys Cys Leu
1880                1885                1890

Asp Asp Ile Glu Lys Lys Leu Ala Ser Leu Pro Glu Pro Arg Asp
1895                1900                1905

Glu Arg Lys Ile Lys Glu Ile Asp Arg Glu Leu Gln Lys Lys Lys
1910                1915                1920

Glu Glu Leu Asn Ala Val Arg Arg Gln Ala Glu Gly Leu Ser Glu
1925                1930                1935

Asp Gly Ala Ala Met Ala Val Glu Pro Thr Gln Ile Gln Leu Ser
1940                1945                1950

Lys Arg Trp Arg Glu Ile Glu Ser Lys Phe Ala Gln Phe Arg Arg
1955                1960                1965

Leu Asn Phe Ala Gln Ile His Thr Val Arg Glu Glu Thr Met Met
1970                1975                1980

Val Met Thr Glu Asp Met Pro Leu Glu Ile Ser Tyr Val Pro Ser
1985                1990                1995

Thr Tyr Leu Thr Glu Ile Thr His Val Ser Gln Ala Leu Leu Glu
2000                2005                2010

Val Glu Gln Leu Leu Asn Ala Pro Asp Leu Cys Ala Lys Asp Phe
2015                2020                2025

Glu Asp Leu Phe Lys Gln Glu Glu Ser Leu Lys Asn Ile Lys Asp
2030                2035                2040

Ser Leu Gln Gln Ser Ser Gly Arg Ile Asp Ile Ile His Ser Lys
2045                2050                2055

Lys Thr Ala Ala Leu Gln Ser Ala Thr Pro Val Glu Arg Val Lys
2060                2065                2070

Leu Gln Glu Ala Leu Ser Gln Leu Asp Phe Gln Trp Glu Lys Val
2075                2080                2085

Asn Lys Met Tyr Lys Asp Arg Gln Gly Arg Phe Asp Arg Ser Val
2090                2095                2100

Glu Lys Trp Arg Arg Phe His Tyr Asp Ile Lys Ile Phe Asn Gln
2105                2110                2115

Trp Leu Thr Glu Ala Glu Gln Phe Leu Arg Lys Thr Gln Ile Pro
2120                2125                2130

Glu Asn Trp Glu His Ala Lys Tyr Lys Trp Tyr Leu Lys Glu Leu
2135                2140                2145

Gln Asp Gly Ile Gly Gln Arg Gln Thr Val Val Arg Thr Leu Asn
2150                2155                2160

Ala Thr Gly Glu Glu Ile Ile Gln Gln Ser Ser Lys Thr Asp Ala
2165                2170                2175

Ser Ile Leu Gln Glu Lys Leu Gly Ser Leu Asn Leu Arg Trp Gln
2180                2185                2190

Glu Val Cys Lys Gln Leu Ser Asp Arg Lys Lys Arg Leu Glu Glu
2195                2200                2205

```
Gln Lys Asn Ile Leu Ser Glu Phe Gln Arg Asp Leu Asn Glu Phe
2210                     2215                2220

Val Leu Trp Leu Glu Glu Ala Asp Asn Ile Ala Ser Ile Pro Leu
2225                     2230                2235

Glu Pro Gly Lys Glu Gln Gln Leu Lys Glu Lys Leu Glu Gln Val
2240                     2245                2250

Lys Leu Leu Val Glu Glu Leu Pro Leu Arg Gln Gly Ile Leu Lys
2255                     2260                2265

Gln Leu Asn Glu Thr Gly Gly Pro Val Leu Val Ser Ala Pro Ile
2270                     2275                2280

Ser Pro Glu Glu Gln Asp Lys Leu Glu Asn Lys Leu Lys Gln Thr
2285                     2290                2295

Asn Leu Gln Trp Ile Lys Val Ser Arg Ala Leu Pro Glu Lys Gln
2300                     2305                2310

Gly Glu Ile Glu Ala Gln Ile Lys Asp Leu Gly Gln Leu Glu Lys
2315                     2320                2325

Lys Leu Glu Asp Leu Glu Glu Gln Leu Asn His Leu Leu Leu Trp
2330                     2335                2340

Leu Ser Pro Ile Arg Asn Gln Leu Glu Ile Tyr Asn Gln Pro Asn
2345                     2350                2355

Gln Glu Gly Pro Phe Asp Val Gln Glu Thr Glu Ile Ala Val Gln
2360                     2365                2370

Ala Lys Gln Pro Asp Val Glu Glu Ile Leu Ser Lys Gly Gln His
2375                     2380                2385

Leu Tyr Lys Glu Lys Pro Ala Thr Gln Pro Val Lys Arg Lys Leu
2390                     2395                2400

Glu Asp Leu Ser Ser Glu Trp Lys Ala Val Asn Arg Leu Leu Gln
2405                     2410                2415

Glu Leu Arg Ala Lys Gln Pro Asp Leu Ala Pro Gly Leu Thr Thr
2420                     2425                2430

Ile Gly Ala Ser Pro Thr Gln Thr Val Thr Leu Val Thr Gln Pro
2435                     2440                2445

Val Val Thr Lys Glu Thr Ala Ile Ser Lys Leu Glu Met Pro Ser
2450                     2455                2460

Ser Leu Met Leu Glu Val Pro Ala Leu Ala Asp Phe Asn Arg Ala
2465                     2470                2475

Trp Thr Glu Leu Thr Asp Trp Leu Ser Leu Leu Asp Gln Val Ile
2480                     2485                2490

Lys Ser Gln Arg Val Met Val Gly Asp Leu Glu Asp Ile Asn Glu
2495                     2500                2505

Met Ile Ile Lys Gln Lys Ala Thr Met Gln Asp Leu Glu Gln Arg
2510                     2515                2520

Arg Pro Gln Leu Glu Glu Leu Ile Thr Ala Ala Gln Asn Leu Lys
2525                     2530                2535

Asn Lys Thr Ser Asn Gln Glu Ala Arg Thr Ile Ile Thr Asp Arg
2540                     2545                2550

Ile Glu Arg Ile Gln Asn Gln Trp Asp Glu Val Gln Glu His Leu
2555                     2560                2565

Gln Asn Arg Arg Gln Gln Leu Asn Glu Met Leu Lys Asp Ser Thr
2570                     2575                2580

Gln Trp Leu Glu Ala Lys Glu Ala Glu Gln Val Leu Gly Gln
2585                     2590                2595

Ala Arg Ala Lys Leu Glu Ser Trp Lys Glu Gly Pro Tyr Thr Val
```

-continued

```
              2600               2605                2610

Asp Ala Ile Gln Lys Lys Ile Thr Glu Thr Lys Gln Leu Ala Lys
    2615                2620                2625

Asp Leu Arg Gln Trp Gln Thr Asn Val Asp Val Ala Asn Asp Leu
    2630                2635                2640

Ala Leu Lys Leu Leu Arg Asp Tyr Ser Ala Asp Asp Thr Arg Lys
    2645                2650                2655

Val His Met Ile Thr Glu Asn Ile Asn Ala Ser Trp Arg Ser Ile
    2660                2665                2670

His Lys Arg Val Ser Glu Arg Glu Ala Ala Leu Glu Glu Thr His
    2675                2680                2685

Arg Leu Leu Gln Gln Phe Pro Leu Asp Leu Glu Lys Phe Leu Ala
    2690                2695                2700

Trp Leu Thr Glu Ala Glu Thr Thr Ala Asn Val Leu Gln Asp Ala
    2705                2710                2715

Thr Arg Lys Glu Arg Leu Leu Glu Asp Ser Lys Gly Val Lys Glu
    2720                2725                2730

Leu Met Lys Gln Trp Gln Asp Leu Gln Gly Glu Ile Glu Ala His
    2735                2740                2745

Thr Asp Val Tyr His Asn Leu Asp Glu Asn Ser Gln Lys Ile Leu
    2750                2755                2760

Arg Ser Leu Glu Gly Ser Asp Asp Ala Val Leu Leu Gln Arg Arg
    2765                2770                2775

Leu Asp Asn Met Asn Phe Lys Trp Ser Glu Leu Arg Lys Lys Ser
    2780                2785                2790

Leu Asn Ile Arg Ser His Leu Glu Ala Ser Ser Asp Gln Trp Lys
    2795                2800                2805

Arg Leu His Leu Ser Leu Gln Glu Leu Leu Val Trp Leu Gln Leu
    2810                2815                2820

Lys Asp Asp Glu Leu Ser Arg Gln Ala Pro Ile Gly Gly Asp Phe
    2825                2830                2835

Pro Ala Val Gln Lys Gln Asn Asp Val His Arg Ala Phe Lys Arg
    2840                2845                2850

Glu Leu Lys Thr Lys Glu Pro Val Ile Met Ser Thr Leu Glu Thr
    2855                2860                2865

Val Arg Ile Phe Leu Thr Glu Gln Pro Leu Glu Gly Leu Glu Lys
    2870                2875                2880

Leu Tyr Gln Glu Pro Arg Glu Leu Pro Pro Glu Glu Arg Ala Gln
    2885                2890                2895

Asn Val Thr Arg Leu Leu Arg Lys Gln Ala Glu Glu Val Asn Thr
    2900                2905                2910

Glu Trp Glu Lys Leu Asn Leu His Ser Ala Asp Trp Gln Arg Lys
    2915                2920                2925

Ile Asp Glu Thr Leu Glu Arg Leu Gln Glu Leu Gln Glu Ala Thr
    2930                2935                2940

Asp Glu Leu Asp Leu Lys Leu Arg Gln Ala Glu Val Ile Lys Gly
    2945                2950                2955

Ser Trp Gln Pro Val Gly Asp Leu Leu Ile Asp Ser Leu Gln Asp
    2960                2965                2970

His Leu Glu Lys Val Lys Ala Leu Arg Gly Glu Ile Ala Pro Leu
    2975                2980                2985

Lys Glu Asn Val Ser His Val Asn Asp Leu Ala Arg Gln Leu Thr
    2990                2995                3000
```

-continued

Thr Leu Gly Ile Gln Leu Ser Pro Tyr Asn Leu Ser Thr Leu Glu
3005                3010                3015

Asp Leu Asn Thr Arg Trp Lys Leu Leu Gln Val Ala Val Glu Asp
3020                3025                3030

Arg Val Arg Gln Leu His Glu Ala His Arg Asp Phe Gly Pro Ala
3035                3040                3045

Ser Gln His Phe Leu Ser Thr Ser Val Gln Gly Pro Trp Glu Arg
3050                3055                3060

Ala Ile Ser Pro Asn Lys Val Pro Tyr Tyr Ile Asn His Glu Thr
3065                3070                3075

Gln Thr Thr Cys Trp Asp His Pro Lys Met Thr Glu Leu Tyr Gln
3080                3085                3090

Ser Leu Ala Asp Leu Asn Asn Val Arg Phe Ser Ala Tyr Arg Thr
3095                3100                3105

Ala Met Lys Leu Arg Arg Leu Gln Lys Ala Leu Cys Leu Asp Leu
3110                3115                3120

Leu Ser Leu Ser Ala Ala Cys Asp Ala Leu Asp Gln His Asn Leu
3125                3130                3135

Lys Gln Asn Asp Gln Pro Met Asp Ile Leu Gln Ile Ile Asn Cys
3140                3145                3150

Leu Thr Thr Ile Tyr Asp Arg Leu Glu Gln Glu His Asn Asn Leu
3155                3160                3165

Val Asn Val Pro Leu Cys Val Asp Met Cys Leu Asn Trp Leu Leu
3170                3175                3180

Asn Val Tyr Asp Thr Gly Arg Thr Gly Arg Ile Arg Val Leu Ser
3185                3190                3195

Phe Lys Thr Gly Ile Ile Ser Leu Cys Lys Ala His Leu Glu Asp
3200                3205                3210

Lys Tyr Arg Tyr Leu Phe Lys Gln Val Ala Ser Ser Thr Gly Phe
3215                3220                3225

Cys Asp Gln Arg Arg Leu Gly Leu Leu Leu His Asp Ser Ile Gln
3230                3235                3240

Ile Pro Arg Gln Leu Gly Glu Val Ala Ser Phe Gly Gly Ser Asn
3245                3250                3255

Ile Glu Pro Ser Val Arg Ser Cys Phe Gln Phe Ala Asn Asn Lys
3260                3265                3270

Pro Glu Ile Glu Ala Ala Leu Phe Leu Asp Trp Met Arg Leu Glu
3275                3280                3285

Pro Gln Ser Met Val Trp Leu Pro Val Leu His Arg Val Ala Ala
3290                3295                3300

Ala Glu Thr Ala Lys His Gln Ala Lys Cys Asn Ile Cys Lys Glu
3305                3310                3315

Cys Pro Ile Ile Gly Phe Arg Tyr Arg Ser Leu Lys His Phe Asn
3320                3325                3330

Tyr Asp Ile Cys Gln Ser Cys Phe Phe Ser Gly Arg Val Ala Lys
3335                3340                3345

Gly His Lys Met His Tyr Pro Met Val Glu Tyr Cys Thr Pro Thr
3350                3355                3360

Thr Ser Gly Glu Asp Val Arg Asp Phe Ala Lys Val Leu Lys Asn
3365                3370                3375

Lys Phe Arg Thr Lys Arg Tyr Phe Ala Lys His Pro Arg Met Gly
3380                3385                3390

| | | | | | | | | | | |
|---|---|---|---|---|---|---|---|---|---|---|
| Tyr | Leu | Pro | Val | Gln | Thr | Val | Leu | Glu | Gly | Asp | Asn | Met | Glu | Thr |
| | | 3395 | | | | 3400 | | | | 3405 | | | | |

Tyr Leu Pro Val Gln Thr Val Leu Glu Gly Asp Asn Met Glu Thr
   3395                3400                3405

Pro Val Thr Leu Ile Asn Phe Trp Pro Val Asp Ser Ala Pro Ala
   3410                3415                3420

Ser Ser Pro Gln Leu Ser His Asp Asp Thr His Ser Arg Ile Glu
   3425                3430                3435

His Tyr Ala Ser Arg Leu Ala Glu Met Glu Asn Ser Asn Gly Ser
   3440                3445                3450

Tyr Leu Asn Asp Ser Ile Ser Pro Asn Glu Ser Ile Asp Asp Glu
   3455                3460                3465

His Leu Leu Ile Gln His Tyr Cys Gln Ser Leu Asn Gln Asp Ser
   3470                3475                3480

Pro Leu Ser Gln Pro Arg Ser Pro Ala Gln Ile Leu Ile Ser Leu
   3485                3490                3495

Glu Ser Glu Glu Arg Gly Glu Leu Glu Arg Ile Leu Ala Asp Leu
   3500                3505                3510

Glu Glu Glu Asn Arg Asn Leu Gln Ala Glu Tyr Asp Arg Leu Lys
   3515                3520                3525

Gln Gln His Glu His Lys Gly Leu Ser Pro Leu Pro Ser Pro Pro
   3530                3535                3540

Glu Met Met Pro Thr Ser Pro Gln Ser Pro Arg Asp Ala Glu Leu
   3545                3550                3555

Ile Ala Glu Ala Lys Leu Leu Arg Gln His Lys Gly Arg Leu Glu
   3560                3565                3570

Ala Arg Met Gln Ile Leu Glu Asp His Asn Lys Gln Leu Glu Ser
   3575                3580                3585

Gln Leu His Arg Leu Arg Gln Leu Leu Glu Gln Pro Gln Ala Glu
   3590                3595                3600

Ala Lys Val Asn Gly Thr Thr Val Ser Ser Pro Ser Thr Ser Leu
   3605                3610                3615

Gln Arg Ser Asp Ser Ser Gln Pro Met Leu Leu Arg Val Val Gly
   3620                3625                3630

Ser Gln Thr Ser Asp Ser Met Gly Glu Glu Asp Leu Leu Ser Pro
   3635                3640                3645

Pro Gln Asp Thr Ser Thr Gly Leu Glu Glu Val Met Glu Gln Leu
   3650                3655                3660

Asn Asn Ser Phe Pro Ser Ser Arg Gly Arg Asn Thr Pro Gly Lys
   3665                3670                3675

Pro Met Arg Glu Asp Thr Met
   3680                3685

<210> SEQ ID NO 2
<211> LENGTH: 75
<212> TYPE: RNA
<213> ORGANISM: Artificial Sequence
<220> FEATURE:
<223> OTHER INFORMATION: exon

<400> SEQUENCE: 2
ccaggauggc auugggcagc ggcaaacugu gucagaaca uugaaugcaa cuggggaaga    60
aauaauucag caauc                                                   75

<210> SEQ ID NO 3
<211> LENGTH: 25
<212> TYPE: RNA
<213> ORGANISM: Artificial Sequence

```
<220> FEATURE:
<223> OTHER INFORMATION: oligonucleotide

<400> SEQUENCE: 3
uuugccgcug cccaaugcca uccug                                                25

<210> SEQ ID NO 4
<211> LENGTH: 25
<212> TYPE: RNA
<213> ORGANISM: Artificial Sequence
<220> FEATURE:
<223> OTHER INFORMATION: oligonucleotide

<400> SEQUENCE: 4
auucaauguu cugacaacag uuugc                                                25

<210> SEQ ID NO 5
<211> LENGTH: 25
<212> TYPE: RNA
<213> ORGANISM: Artificial Sequence
<220> FEATURE:
<223> OTHER INFORMATION: oligonucleotide

<400> SEQUENCE: 5
ccaguugcau ucaauguucu gacaa                                                25

<210> SEQ ID NO 6
<211> LENGTH: 22
<212> TYPE: RNA
<213> ORGANISM: Artificial Sequence
<220> FEATURE:
<223> OTHER INFORMATION: oligonucleotide

<400> SEQUENCE: 6
caguugcauu caauguucug ac                                                   22

<210> SEQ ID NO 7
<211> LENGTH: 20
<212> TYPE: RNA
<213> ORGANISM: Artificial Sequence
<220> FEATURE:
<223> OTHER INFORMATION: oligonucleotide

<400> SEQUENCE: 7
aguugcauuc aauguucuga                                                      20

<210> SEQ ID NO 8
<211> LENGTH: 21
<212> TYPE: RNA
<213> ORGANISM: Artificial Sequence
<220> FEATURE:
<223> OTHER INFORMATION: oligonucleotide

<400> SEQUENCE: 8
gauugcugaa uuauuucuuc c                                                    21

<210> SEQ ID NO 9
<211> LENGTH: 25
<212> TYPE: RNA
<213> ORGANISM: Artificial Sequence
<220> FEATURE:
<223> OTHER INFORMATION: oligonucleotide

<400> SEQUENCE: 9
gauugcugaa uuauuucuuc cccag                                                25
```

<210> SEQ ID NO 10
<211> LENGTH: 25
<212> TYPE: RNA
<213> ORGANISM: Artificial Sequence
<220> FEATURE:
<223> OTHER INFORMATION: oligonucleotide

<400> SEQUENCE: 10
auugcugaau uauuucuucc ccagu                                          25

<210> SEQ ID NO 11
<211> LENGTH: 25
<212> TYPE: RNA
<213> ORGANISM: Artificial Sequence
<220> FEATURE:
<223> OTHER INFORMATION: oligonucleotide

<400> SEQUENCE: 11
uugcugaauu auuucuuccc caguu                                          25

<210> SEQ ID NO 12
<211> LENGTH: 25
<212> TYPE: RNA
<213> ORGANISM: Artificial Sequence
<220> FEATURE:
<223> OTHER INFORMATION: oligonucleotide

<400> SEQUENCE: 12
ugcugaauua uuucuucccc aguug                                          25

<210> SEQ ID NO 13
<211> LENGTH: 25
<212> TYPE: RNA
<213> ORGANISM: Artificial Sequence
<220> FEATURE:
<223> OTHER INFORMATION: oligonucleotide

<400> SEQUENCE: 13
gcugaauuau uucuucccca guugc                                          25

<210> SEQ ID NO 14
<211> LENGTH: 25
<212> TYPE: RNA
<213> ORGANISM: Artificial Sequence
<220> FEATURE:
<223> OTHER INFORMATION: oligonucleotide

<400> SEQUENCE: 14
cugaauuauu ucuuccccag uugca                                          25

<210> SEQ ID NO 15
<211> LENGTH: 25
<212> TYPE: RNA
<213> ORGANISM: Artificial Sequence
<220> FEATURE:
<223> OTHER INFORMATION: oligonucleotide

<400> SEQUENCE: 15
ugaauuauuu cuuccccagu ugcau                                          25

<210> SEQ ID NO 16
<211> LENGTH: 25
<212> TYPE: RNA
<213> ORGANISM: Artificial Sequence
<220> FEATURE:
<223> OTHER INFORMATION: oligonucleotide

```
<400> SEQUENCE: 16
gaauuauuuc uuccccaguu gcauu                                              25

<210> SEQ ID NO 17
<211> LENGTH: 25
<212> TYPE: RNA
<213> ORGANISM: Artificial Sequence
<220> FEATURE:
<223> OTHER INFORMATION: oligonucleotide

<400> SEQUENCE: 17
aauuauuucu uccccaguug cauuc                                              25

<210> SEQ ID NO 18
<211> LENGTH: 25
<212> TYPE: RNA
<213> ORGANISM: Artificial Sequence
<220> FEATURE:
<223> OTHER INFORMATION: oligonucleotide

<400> SEQUENCE: 18
auuauuucuu ccccaguugc auuca                                              25

<210> SEQ ID NO 19
<211> LENGTH: 25
<212> TYPE: RNA
<213> ORGANISM: Artificial Sequence
<220> FEATURE:
<223> OTHER INFORMATION: oligonucleotide

<400> SEQUENCE: 19
uuauuucuuc cccaguugca uucaa                                              25

<210> SEQ ID NO 20
<211> LENGTH: 25
<212> TYPE: RNA
<213> ORGANISM: Artificial Sequence
<220> FEATURE:
<223> OTHER INFORMATION: oligonucleotide

<400> SEQUENCE: 20
uauuucuucc ccaguugcau ucaau                                              25

<210> SEQ ID NO 21
<211> LENGTH: 25
<212> TYPE: RNA
<213> ORGANISM: Artificial Sequence
<220> FEATURE:
<223> OTHER INFORMATION: oligonucleotide

<400> SEQUENCE: 21
auuucuuccc caguugcauu caaug                                              25

<210> SEQ ID NO 22
<211> LENGTH: 25
<212> TYPE: RNA
<213> ORGANISM: Artificial Sequence
<220> FEATURE:
<223> OTHER INFORMATION: oligonucleotide

<400> SEQUENCE: 22
uuucuucccc aguugcauuc aaugu                                              25

<210> SEQ ID NO 23
```

```
<211> LENGTH: 25
<212> TYPE: RNA
<213> ORGANISM: Artificial Sequence
<220> FEATURE:
<223> OTHER INFORMATION: oligonucleotide

<400> SEQUENCE: 23 uucuuccca guugcauuca auguu                                          25

<210> SEQ ID NO 24
<211> LENGTH: 25
<212> TYPE: RNA
<213> ORGANISM: Artificial Sequence
<220> FEATURE:
<223> OTHER INFORMATION: oligonucleotide

<400> SEQUENCE: 24 ucuucccag uugcauucaa uguuc                                          25

<210> SEQ ID NO 25
<211> LENGTH: 25
<212> TYPE: RNA
<213> ORGANISM: Artificial Sequence
<220> FEATURE:
<223> OTHER INFORMATION: oligonucleotide

<400> SEQUENCE: 25 cuucccagu ugcauucaau guucu                                          25

<210> SEQ ID NO 26
<211> LENGTH: 25
<212> TYPE: RNA
<213> ORGANISM: Artificial Sequence
<220> FEATURE:
<223> OTHER INFORMATION: oligonucleotide

<400> SEQUENCE: 26 uucccaguu gcauucaaug uucug                                          25

<210> SEQ ID NO 27
<211> LENGTH: 25
<212> TYPE: RNA
<213> ORGANISM: Artificial Sequence
<220> FEATURE:
<223> OTHER INFORMATION: oligonucleotide

<400> SEQUENCE: 27 ucccaguug cauucaaugu ucuga                                          25

<210> SEQ ID NO 28
<211> LENGTH: 25
<212> TYPE: RNA
<213> ORGANISM: Artificial Sequence
<220> FEATURE:
<223> OTHER INFORMATION: oligonucleotide

<400> SEQUENCE: 28 cccaguugc auucaauguu cugac                                          25

<210> SEQ ID NO 29
<211> LENGTH: 25
<212> TYPE: RNA
<213> ORGANISM: Artificial Sequence
<220> FEATURE:
<223> OTHER INFORMATION: oligonucleotide

<400> SEQUENCE: 29
```
cccaguugca uucaauguuc ugaca                                    25

<210> SEQ ID NO 30
<211> LENGTH: 25
<212> TYPE: RNA
<213> ORGANISM: Artificial Sequence
<220> FEATURE:
<223> OTHER INFORMATION: oligonucleotide

<400> SEQUENCE: 30
ccaguugcau ucaauguucu gacaa                                    25

<210> SEQ ID NO 31
<211> LENGTH: 25
<212> TYPE: RNA
<213> ORGANISM: Artificial Sequence
<220> FEATURE:
<223> OTHER INFORMATION: oligonucleotide

<400> SEQUENCE: 31
caguugcauu caauguucug acaac                                    25

<210> SEQ ID NO 32
<211> LENGTH: 25
<212> TYPE: RNA
<213> ORGANISM: Artificial Sequence
<220> FEATURE:
<223> OTHER INFORMATION: oligonucleotide

<400> SEQUENCE: 32
aguugcauuc aauguucuga caaca                                    25

<210> SEQ ID NO 33
<211> LENGTH: 20
<212> TYPE: RNA
<213> ORGANISM: Artificial Sequence
<220> FEATURE:
<223> OTHER INFORMATION: oligonucleotide

<400> SEQUENCE: 33
uccuguagaa uacuggcauc                                          20

<210> SEQ ID NO 34
<211> LENGTH: 27
<212> TYPE: RNA
<213> ORGANISM: Artificial Sequence
<220> FEATURE:
<223> OTHER INFORMATION: oligonucleotide

<400> SEQUENCE: 34
ugcagaccuc cugccaccgc agauuca                                  27

<210> SEQ ID NO 35
<211> LENGTH: 34
<212> TYPE: RNA
<213> ORGANISM: Artificial Sequence
<220> FEATURE:
<223> OTHER INFORMATION: oligonucleotide

<400> SEQUENCE: 35
uugcagaccu ccugccaccg cagauucagg cuuc                          34

<210> SEQ ID NO 36
<211> LENGTH: 25
<212> TYPE: RNA

```
<213> ORGANISM: Artificial Sequence
<220> FEATURE:
<223> OTHER INFORMATION: oligonucleotide

<400> SEQUENCE: 36
guugcauuca auguucugac aacag                                              25

<210> SEQ ID NO 37
<211> LENGTH: 25
<212> TYPE: RNA
<213> ORGANISM: Artificial Sequence
<220> FEATURE:
<223> OTHER INFORMATION: oligonucleotide

<400> SEQUENCE: 37
uugcauucaa uguucugaca acagu                                              25

<210> SEQ ID NO 38
<211> LENGTH: 25
<212> TYPE: RNA
<213> ORGANISM: Artificial Sequence
<220> FEATURE:
<223> OTHER INFORMATION: oligonucleotide

<400> SEQUENCE: 38
ugcauucaau guucugacaa caguu                                              25

<210> SEQ ID NO 39
<211> LENGTH: 25
<212> TYPE: RNA
<213> ORGANISM: Artificial Sequence
<220> FEATURE:
<223> OTHER INFORMATION: oligonucleotide

<400> SEQUENCE: 39
gcauucaaug uucugacaac aguuu                                              25

<210> SEQ ID NO 40
<211> LENGTH: 25
<212> TYPE: RNA
<213> ORGANISM: Artificial Sequence
<220> FEATURE:
<223> OTHER INFORMATION: oligonucleotide

<400> SEQUENCE: 40
cauucaaugu ucugacaaca guuug                                              25

<210> SEQ ID NO 41
<211> LENGTH: 25
<212> TYPE: RNA
<213> ORGANISM: Artificial Sequence
<220> FEATURE:
<223> OTHER INFORMATION: oligonucleotide

<400> SEQUENCE: 41
auucaauguu cugacaacag uuugc                                              25

<210> SEQ ID NO 42
<211> LENGTH: 25
<212> TYPE: RNA
<213> ORGANISM: Artificial Sequence
<220> FEATURE:
<223> OTHER INFORMATION: oligonucleotide

<400> SEQUENCE: 42
ucaauguucu gacaacaguu ugccg                                              25
```

<210> SEQ ID NO 43
<211> LENGTH: 25
<212> TYPE: RNA
<213> ORGANISM: Artificial Sequence
<220> FEATURE:
<223> OTHER INFORMATION: oligonucleotide

<400> SEQUENCE: 43
caauguucug acaacaguuu gccgc                                            25

<210> SEQ ID NO 44
<211> LENGTH: 25
<212> TYPE: RNA
<213> ORGANISM: Artificial Sequence
<220> FEATURE:
<223> OTHER INFORMATION: oligonucleotide

<400> SEQUENCE: 44
aauguucuga caacaguuug ccgcu                                            25

<210> SEQ ID NO 45
<211> LENGTH: 25
<212> TYPE: RNA
<213> ORGANISM: Artificial Sequence
<220> FEATURE:
<223> OTHER INFORMATION: oligonucleotide

<400> SEQUENCE: 45
auguucugac aacaguuugc cgcug                                            25

<210> SEQ ID NO 46
<211> LENGTH: 25
<212> TYPE: RNA
<213> ORGANISM: Artificial Sequence
<220> FEATURE:
<223> OTHER INFORMATION: oligonucleotide

<400> SEQUENCE: 46
uguucugaca acaguuugcc gcugc                                            25

<210> SEQ ID NO 47
<211> LENGTH: 25
<212> TYPE: RNA
<213> ORGANISM: Artificial Sequence
<220> FEATURE:
<223> OTHER INFORMATION: oligonucleotide

<400> SEQUENCE: 47
guucugacaa caguuugccg cugcc                                            25

<210> SEQ ID NO 48
<211> LENGTH: 25
<212> TYPE: RNA
<213> ORGANISM: Artificial Sequence
<220> FEATURE:
<223> OTHER INFORMATION: oligonucleotide

<400> SEQUENCE: 48
uucugacaac aguuugccgc ugccc                                            25

<210> SEQ ID NO 49
<211> LENGTH: 25
<212> TYPE: RNA
<213> ORGANISM: Artificial Sequence
<220> FEATURE:

<223> OTHER INFORMATION: oligonucleotide

<400> SEQUENCE: 49
ucugacaaca guuugccgcu gccca    25

<210> SEQ ID NO 50
<211> LENGTH: 25
<212> TYPE: RNA
<213> ORGANISM: Artificial Sequence
<220> FEATURE:
<223> OTHER INFORMATION: oligonucleotide

<400> SEQUENCE: 50
cugacaacag uuugccgcug cccaa    25

<210> SEQ ID NO 51
<211> LENGTH: 25
<212> TYPE: RNA
<213> ORGANISM: Artificial Sequence
<220> FEATURE:
<223> OTHER INFORMATION: oligonucleotide

<400> SEQUENCE: 51
ugacaacagu ugccgcugc ccaau    25

<210> SEQ ID NO 52
<211> LENGTH: 25
<212> TYPE: RNA
<213> ORGANISM: Artificial Sequence
<220> FEATURE:
<223> OTHER INFORMATION: oligonucleotide

<400> SEQUENCE: 52
gacaacaguu ugccgcugcc caaug    25

<210> SEQ ID NO 53
<211> LENGTH: 25
<212> TYPE: RNA
<213> ORGANISM: Artificial Sequence
<220> FEATURE:
<223> OTHER INFORMATION: oligonucleotide

<400> SEQUENCE: 53
acaacaguuu gccgcugccc aaugc    25

<210> SEQ ID NO 54
<211> LENGTH: 25
<212> TYPE: RNA
<213> ORGANISM: Artificial Sequence
<220> FEATURE:
<223> OTHER INFORMATION: oligonucleotide

<400> SEQUENCE: 54
caacaguuug ccgcugccca augcc    25

<210> SEQ ID NO 55
<211> LENGTH: 25
<212> TYPE: RNA
<213> ORGANISM: Artificial Sequence
<220> FEATURE:
<223> OTHER INFORMATION: oligonucleotide

<400> SEQUENCE: 55
aacaguuugc cgcugcccaa ugcca    25

```
<210> SEQ ID NO 56
<211> LENGTH: 25
<212> TYPE: RNA
<213> ORGANISM: Artificial Sequence
<220> FEATURE:
<223> OTHER INFORMATION: oligonucleotide

<400> SEQUENCE: 56
acaguuugcc gcugcccaau gccau                                          25

<210> SEQ ID NO 57
<211> LENGTH: 25
<212> TYPE: RNA
<213> ORGANISM: Artificial Sequence
<220> FEATURE:
<223> OTHER INFORMATION: oligonucleotide

<400> SEQUENCE: 57
caguuugccg cugcccaaug ccauc                                          25

<210> SEQ ID NO 58
<211> LENGTH: 25
<212> TYPE: RNA
<213> ORGANISM: Artificial Sequence
<220> FEATURE:
<223> OTHER INFORMATION: oligonucleotide

<400> SEQUENCE: 58
aguuugccgc ugcccaaugc caucc                                          25

<210> SEQ ID NO 59
<211> LENGTH: 25
<212> TYPE: RNA
<213> ORGANISM: Artificial Sequence
<220> FEATURE:
<223> OTHER INFORMATION: oligonucleotide

<400> SEQUENCE: 59
guuugccgcu gcccaaugcc auccu                                          25

<210> SEQ ID NO 60
<211> LENGTH: 25
<212> TYPE: RNA
<213> ORGANISM: Artificial Sequence
<220> FEATURE:
<223> OTHER INFORMATION: oligonucleotide

<400> SEQUENCE: 60
uuugccgcug cccaaugcca uccug                                          25

<210> SEQ ID NO 61
<211> LENGTH: 25
<212> TYPE: RNA
<213> ORGANISM: Artificial Sequence
<220> FEATURE:
<223> OTHER INFORMATION: oligonucleotide

<400> SEQUENCE: 61
uugccgcugc ccaaugccau ccugg                                          25

<210> SEQ ID NO 62
<211> LENGTH: 25
<212> TYPE: RNA
<213> ORGANISM: Artificial Sequence
<220> FEATURE:
<223> OTHER INFORMATION: oligonucleotide
```

<400> SEQUENCE: 62
ugccgcugcc caaugccauc cugga                                                25

<210> SEQ ID NO 63
<211> LENGTH: 25
<212> TYPE: RNA
<213> ORGANISM: Artificial Sequence
<220> FEATURE:
<223> OTHER INFORMATION: oligonucleotide

<400> SEQUENCE: 63
gccgcugccc aaugccaucc uggag                                                25

<210> SEQ ID NO 64
<211> LENGTH: 25
<212> TYPE: RNA
<213> ORGANISM: Artificial Sequence
<220> FEATURE:
<223> OTHER INFORMATION: oligonucleotide

<400> SEQUENCE: 64
ccgcugccca augccauccu ggagu                                                25

<210> SEQ ID NO 65
<211> LENGTH: 25
<212> TYPE: RNA
<213> ORGANISM: Artificial Sequence
<220> FEATURE:
<223> OTHER INFORMATION: oligonucleotide

<400> SEQUENCE: 65
cgcugcccaa ugccauccug gaguu                                                25

<210> SEQ ID NO 66
<211> LENGTH: 20
<212> TYPE: RNA
<213> ORGANISM: Artificial Sequence
<220> FEATURE:
<223> OTHER INFORMATION: oligoncleotide

<400> SEQUENCE: 66 uguuuugag gauugcugaa                                                       20

<210> SEQ ID NO 67
<211> LENGTH: 40
<212> TYPE: RNA
<213> ORGANISM: Artificial Sequence
<220> FEATURE:
<223> OTHER INFORMATION: oligonucleotide

<400> SEQUENCE: 67
uguucugaca acaguuugcc gcugcccaau gccauccugg                                40

<210> SEQ ID NO 68
<211> LENGTH: 17
<212> TYPE: RNA
<213> ORGANISM: Artificial Sequence
<220> FEATURE:
<223> OTHER INFORMATION: oligonucleotide

<400> SEQUENCE: 68
gcccaaugcc auccugg                                                         17

<210> SEQ ID NO 69
<211> LENGTH: 25

```
<212> TYPE: RNA
<213> ORGANISM: Artificial Sequence
<220> FEATURE:
<223> OTHER INFORMATION: oligonucleotide

<400> SEQUENCE: 69
agagcaggua ccuccaacau caagg                                    25

<210> SEQ ID NO 70
<211> LENGTH: 25
<212> TYPE: RNA
<213> ORGANISM: Artificial Sequence
<220> FEATURE:
<223> OTHER INFORMATION: oligonucleotide

<400> SEQUENCE: 70
gagcagguac cuccaacauc aagga                                    25

<210> SEQ ID NO 71
<211> LENGTH: 25
<212> TYPE: RNA
<213> ORGANISM: Artificial Sequence
<220> FEATURE:
<223> OTHER INFORMATION: oligonucleotide

<400> SEQUENCE: 71
agcagguacc uccaacauca aggaa                                    25

<210> SEQ ID NO 72
<211> LENGTH: 25
<212> TYPE: RNA
<213> ORGANISM: Artificial Sequence
<220> FEATURE:
<223> OTHER INFORMATION: oligonucleotide

<400> SEQUENCE: 72
gcagguaccu ccaacaucaa ggaag                                    25

<210> SEQ ID NO 73
<211> LENGTH: 25
<212> TYPE: RNA
<213> ORGANISM: Artificial Sequence
<220> FEATURE:
<223> OTHER INFORMATION: oligonucleotide

<400> SEQUENCE: 73
cagguaccuc caacaucaag gaaga                                    25

<210> SEQ ID NO 74
<211> LENGTH: 25
<212> TYPE: RNA
<213> ORGANISM: Artificial Sequence
<220> FEATURE:
<223> OTHER INFORMATION: oligonucleotide

<400> SEQUENCE: 74
agguaccucc aacaucaagg aagau                                    25

<210> SEQ ID NO 75
<211> LENGTH: 25
<212> TYPE: RNA
<213> ORGANISM: Artificial Sequence
<220> FEATURE:
<223> OTHER INFORMATION: oligonucleotide

<400> SEQUENCE: 75
```
gguaccucca acaucaagga agaug                                          25

<210> SEQ ID NO 76
<211> LENGTH: 25
<212> TYPE: RNA
<213> ORGANISM: Artificial Sequence
<220> FEATURE:
<223> OTHER INFORMATION: oligonucleotide

<400> SEQUENCE: 76
guaccuccaa caucaaggaa gaugg                                          25

<210> SEQ ID NO 77
<211> LENGTH: 25
<212> TYPE: RNA
<213> ORGANISM: Artificial Sequence
<220> FEATURE:
<223> OTHER INFORMATION: oligonucleotide

<400> SEQUENCE: 77
uaccuccaac aucaaggaag auggc                                          25

<210> SEQ ID NO 78
<211> LENGTH: 25
<212> TYPE: RNA
<213> ORGANISM: Artificial Sequence
<220> FEATURE:
<223> OTHER INFORMATION: oligonucleotide

<400> SEQUENCE: 78
accuccaaca ucaaggaaga uggca                                          25

<210> SEQ ID NO 79
<211> LENGTH: 25
<212> TYPE: RNA
<213> ORGANISM: Artificial Sequence
<220> FEATURE:
<223> OTHER INFORMATION: oligonucleotide

<400> SEQUENCE: 79
ccuccaacau caaggaagau ggcau                                          25

<210> SEQ ID NO 80
<211> LENGTH: 25
<212> TYPE: RNA
<213> ORGANISM: Artificial Sequence
<220> FEATURE:
<223> OTHER INFORMATION: oligonucleotide

<400> SEQUENCE: 80
cuccaacauc aaggaagaug gcauu                                          25

<210> SEQ ID NO 81
<211> LENGTH: 30
<212> TYPE: RNA
<213> ORGANISM: Artificial Sequence
<220> FEATURE:
<223> OTHER INFORMATION: oligonucleotide

<400> SEQUENCE: 81
cuccaacauc aaggaagaug gcauuucuag                                     30

<210> SEQ ID NO 82
<211> LENGTH: 25
<212> TYPE: RNA
<213> ORGANISM: Artificial Sequence

```
<220> FEATURE:
<223> OTHER INFORMATION: oligonucleotide

<400> SEQUENCE: 82
uccaacauca aggaagaugg cauuu                                    25

<210> SEQ ID NO 83
<211> LENGTH: 25
<212> TYPE: RNA
<213> ORGANISM: Artificial Sequence
<220> FEATURE:
<223> OTHER INFORMATION: oligonucleotide

<400> SEQUENCE: 83
ccaacaucaa ggaagauggc auuuc                                    25

<210> SEQ ID NO 84
<211> LENGTH: 25
<212> TYPE: RNA
<213> ORGANISM: Artificial Sequence
<220> FEATURE:
<223> OTHER INFORMATION: oligonucleotide

<400> SEQUENCE: 84
caacaucaag gaagauggca uuucu                                    25

<210> SEQ ID NO 85
<211> LENGTH: 25
<212> TYPE: RNA
<213> ORGANISM: Artificial Sequence
<220> FEATURE:
<223> OTHER INFORMATION: oligonucleotide

<400> SEQUENCE: 85
aacaucaagg aagauggcau uucua                                    25

<210> SEQ ID NO 86
<211> LENGTH: 25
<212> TYPE: RNA
<213> ORGANISM: Artificial Sequence
<220> FEATURE:
<223> OTHER INFORMATION: oligonucleotide

<400> SEQUENCE: 86
acaucaagga agauggcauu ucuag                                    25

<210> SEQ ID NO 87
<211> LENGTH: 30
<212> TYPE: RNA
<213> ORGANISM: Artificial Sequence
<220> FEATURE:
<223> OTHER INFORMATION: oligonucleotide

<400> SEQUENCE: 87
acaucaagga agauggcauu ucuaguuugg                               30

<210> SEQ ID NO 88
<211> LENGTH: 25
<212> TYPE: RNA
<213> ORGANISM: Artificial Sequence
<220> FEATURE:
<223> OTHER INFORMATION: oligonucleotide

<400> SEQUENCE: 88
acaucaagga agauggcauu ucuag                                    25
```

<210> SEQ ID NO 89
<211> LENGTH: 25
<212> TYPE: RNA
<213> ORGANISM: Artificial Sequence
<220> FEATURE:
<223> OTHER INFORMATION: oligonucleotide

<400> SEQUENCE: 89
caucaaggaa gauggcauuu cuagu                                            25

<210> SEQ ID NO 90
<211> LENGTH: 25
<212> TYPE: RNA
<213> ORGANISM: Artificial Sequence
<220> FEATURE:
<223> OTHER INFORMATION: oligonucleotide

<400> SEQUENCE: 90
aucaaggaag auggcauuuc uaguu                                            25

<210> SEQ ID NO 91
<211> LENGTH: 25
<212> TYPE: RNA
<213> ORGANISM: Artificial Sequence
<220> FEATURE:
<223> OTHER INFORMATION: oligonucleotide

<400> SEQUENCE: 91
ucaaggaaga uggcauuucu aguuu                                            25

<210> SEQ ID NO 92
<211> LENGTH: 20
<212> TYPE: RNA
<213> ORGANISM: Artificial Sequence
<220> FEATURE:
<223> OTHER INFORMATION: oligonucleotide

<400> SEQUENCE: 92
ucaaggaaga uggcauuucu                                                  20

<210> SEQ ID NO 93
<211> LENGTH: 25
<212> TYPE: RNA
<213> ORGANISM: Artificial Sequence
<220> FEATURE:
<223> OTHER INFORMATION: oligonucleotide

<400> SEQUENCE: 93
caaggaagau ggcauuucua guuug                                            25

<210> SEQ ID NO 94
<211> LENGTH: 25
<212> TYPE: RNA
<213> ORGANISM: Artificial Sequence
<220> FEATURE:
<223> OTHER INFORMATION: oligonucleotide

<400> SEQUENCE: 94
aaggaagaug gcauuucuag uuugg                                            25

<210> SEQ ID NO 95
<211> LENGTH: 25
<212> TYPE: RNA
<213> ORGANISM: Artificial Sequence
<220> FEATURE:
<223> OTHER INFORMATION: oligonucleotide

```
<400> SEQUENCE: 95
aggaagaugg cauuucuagu uugga                                    25

<210> SEQ ID NO 96
<211> LENGTH: 25
<212> TYPE: RNA
<213> ORGANISM: Artificial Sequence
<220> FEATURE:
<223> OTHER INFORMATION: oligonucleotide

<400> SEQUENCE: 96
ggaagauggc auuucuaguu uggag                                    25

<210> SEQ ID NO 97
<211> LENGTH: 25
<212> TYPE: RNA
<213> ORGANISM: Artificial Sequence
<220> FEATURE:
<223> OTHER INFORMATION: oligonucleotide

<400> SEQUENCE: 97
gaagauggca uuucuaguuu ggaga                                    25

<210> SEQ ID NO 98
<211> LENGTH: 25
<212> TYPE: RNA
<213> ORGANISM: Artificial Sequence
<220> FEATURE:
<223> OTHER INFORMATION: oligonucleotide

<400> SEQUENCE: 98
aagauggcau uucuaguuug gagau                                    25

<210> SEQ ID NO 99
<211> LENGTH: 25
<212> TYPE: RNA
<213> ORGANISM: Artificial Sequence
<220> FEATURE:
<223> OTHER INFORMATION: oligonucleotide

<400> SEQUENCE: 99
agauggcauu ucuaguuugg agaug                                    25

<210> SEQ ID NO 100
<211> LENGTH: 25
<212> TYPE: RNA
<213> ORGANISM: Artificial Sequence
<220> FEATURE:
<223> OTHER INFORMATION: oligonucleotide

<400> SEQUENCE: 100
gauggcauuu cuaguuugga gaugg                                    25

<210> SEQ ID NO 101
<211> LENGTH: 25
<212> TYPE: RNA
<213> ORGANISM: Artificial Sequence
<220> FEATURE:
<223> OTHER INFORMATION: oligonucleotide

<400> SEQUENCE: 101
auggcauuuc uaguuuggag auggc                                    25

<210> SEQ ID NO 102
```

```
<211> LENGTH: 25
<212> TYPE: RNA
<213> ORGANISM: Artificial Sequence
<220> FEATURE:
<223> OTHER INFORMATION: oligonucleotide

<400> SEQUENCE: 102
uggcauuucu aguuggaga uggca                                              25

<210> SEQ ID NO 103
<211> LENGTH: 25
<212> TYPE: RNA
<213> ORGANISM: Artificial Sequence
<220> FEATURE:
<223> OTHER INFORMATION: oligonucleotide

<400> SEQUENCE: 103
ggcauuucua guuggagau ggcag                                              25

<210> SEQ ID NO 104
<211> LENGTH: 25
<212> TYPE: RNA
<213> ORGANISM: Artificial Sequence
<220> FEATURE:
<223> OTHER INFORMATION: oligonucleotide

<400> SEQUENCE: 104
gcauuucuag uuggagaug gcagu                                              25

<210> SEQ ID NO 105
<211> LENGTH: 25
<212> TYPE: RNA
<213> ORGANISM: Artificial Sequence
<220> FEATURE:
<223> OTHER INFORMATION: oligonucleotide

<400> SEQUENCE: 105
cauuucuagu uggagaugg caguu                                              25

<210> SEQ ID NO 106
<211> LENGTH: 25
<212> TYPE: RNA
<213> ORGANISM: Artificial Sequence
<220> FEATURE:
<223> OTHER INFORMATION: oligonucleotide

<400> SEQUENCE: 106
auuucuaguu ggagauggc aguuu                                              25

<210> SEQ ID NO 107
<211> LENGTH: 25
<212> TYPE: RNA
<213> ORGANISM: Artificial Sequence
<220> FEATURE:
<223> OTHER INFORMATION: oligonucleotide

<400> SEQUENCE: 107
uuucuaguuu ggagauggca guuuc                                             25

<210> SEQ ID NO 108
<211> LENGTH: 25
<212> TYPE: RNA
<213> ORGANISM: Artificial Sequence
<220> FEATURE:
<223> OTHER INFORMATION: oligonucleotide

<400> SEQUENCE: 108
```

```
uucuaguuug gagauggcag uuucc                                          25

<210> SEQ ID NO 109
<211> LENGTH: 25
<212> TYPE: RNA
<213> ORGANISM: Artificial Sequence
<220> FEATURE:
<223> OTHER INFORMATION: oligonucleotide

<400> SEQUENCE: 109
ccauuguguu gaauccuuua acauu                                          25

<210> SEQ ID NO 110
<211> LENGTH: 22
<212> TYPE: RNA
<213> ORGANISM: Artificial Sequence
<220> FEATURE:
<223> OTHER INFORMATION: oligonucleotide

<400> SEQUENCE: 110
ccauuguguu gaauccuuua ac                                             22

<210> SEQ ID NO 111
<211> LENGTH: 20
<212> TYPE: RNA
<213> ORGANISM: Artificial Sequence
<220> FEATURE:
<223> OTHER INFORMATION: oligonucleotide

<400> SEQUENCE: 111
auuguguuga auccuuuaac                                                20

<210> SEQ ID NO 112
<211> LENGTH: 20
<212> TYPE: RNA
<213> ORGANISM: Artificial Sequence
<220> FEATURE:
<223> OTHER INFORMATION: oligonucleotide

<400> SEQUENCE: 112
ccuguccuaa gaccugcuca                                                20

<210> SEQ ID NO 113
<211> LENGTH: 25
<212> TYPE: RNA
<213> ORGANISM: Artificial Sequence
<220> FEATURE:
<223> OTHER INFORMATION: oligonucleotide

<400> SEQUENCE: 113
cuuuuggauu gcaucuacug uauag                                          25

<210> SEQ ID NO 114
<211> LENGTH: 25
<212> TYPE: RNA
<213> ORGANISM: Artificial Sequence
<220> FEATURE:
<223> OTHER INFORMATION: oligonucleotide

<400> SEQUENCE: 114
cauucaacug uugccuccgg uucug                                          25

<210> SEQ ID NO 115
<211> LENGTH: 24
<212> TYPE: RNA
```

<213> ORGANISM: Artificial Sequence
<220> FEATURE:
<223> OTHER INFORMATION: oligonucleotide

<400> SEQUENCE: 115
cguuugccuc cgguucugaa ggug                                          24

<210> SEQ ID NO 116
<211> LENGTH: 31
<212> TYPE: RNA
<213> ORGANISM: Artificial Sequence
<220> FEATURE:
<223> OTHER INFORMATION: oligonucleotide

<400> SEQUENCE: 116
cauucaacug uugccuccgg uucugaaggu g                                  31

<210> SEQ ID NO 117
<211> LENGTH: 25
<212> TYPE: RNA
<213> ORGANISM: Artificial Sequence
<220> FEATURE:
<223> OTHER INFORMATION: oligonucleotide

<400> SEQUENCE: 117
cugaaggugu ucuuguacuu caucc                                         25

<210> SEQ ID NO 118
<211> LENGTH: 27
<212> TYPE: RNA
<213> ORGANISM: Artificial Sequence
<220> FEATURE:
<223> OTHER INFORMATION: oligonucleotide

<400> SEQUENCE: 118
uguauaggga cccuccuucc augacuc                                       27

<210> SEQ ID NO 119
<211> LENGTH: 20
<212> TYPE: RNA
<213> ORGANISM: Artificial Sequence
<220> FEATURE:
<223> OTHER INFORMATION: oligonucleotide

<400> SEQUENCE: 119
aucccacuga uucugaauuc                                               20

<210> SEQ ID NO 120
<211> LENGTH: 22
<212> TYPE: RNA
<213> ORGANISM: Artificial Sequence
<220> FEATURE:
<223> OTHER INFORMATION: oligonucleotide

<400> SEQUENCE: 120
uuggcucugg ccuguccuaa ga                                            22

<210> SEQ ID NO 121
<211> LENGTH: 35
<212> TYPE: RNA
<213> ORGANISM: Artificial Sequence
<220> FEATURE:
<223> OTHER INFORMATION: oligonucleotide

<400> SEQUENCE: 121
aagaccugcu cagcuucuuc cuuagcuucc agcca                              35

<210> SEQ ID NO 122
<211> LENGTH: 23
<212> TYPE: RNA
<213> ORGANISM: Artificial Sequence
<220> FEATURE:
<223> OTHER INFORMATION: oligonucleotide

<400> SEQUENCE: 122
ugcauguucc agucguugug ugg                                        23

<210> SEQ ID NO 123
<211> LENGTH: 25
<212> TYPE: RNA
<213> ORGANISM: Artificial Sequence
<220> FEATURE:
<223> OTHER INFORMATION: oligonucleotide

<400> SEQUENCE: 123
cacuauucca gucaaauagg ucugg                                      25

<210> SEQ ID NO 124
<211> LENGTH: 25
<212> TYPE: RNA
<213> ORGANISM: Artificial Sequence
<220> FEATURE:
<223> OTHER INFORMATION: oligonucleotide

<400> SEQUENCE: 124
auuuaccaac cuucaggauc gagua                                      25

<210> SEQ ID NO 125
<211> LENGTH: 21
<212> TYPE: RNA
<213> ORGANISM: Artificial Sequence
<220> FEATURE:
<223> OTHER INFORMATION: oligonucleotide

<400> SEQUENCE: 125
ggccuaaaac acauacacau a                                          21

<210> SEQ ID NO 126
<211> LENGTH: 20
<212> TYPE: RNA
<213> ORGANISM: Artificial Sequence
<220> FEATURE:
<223> OTHER INFORMATION: oligonucleotide

<400> SEQUENCE: 126
ucagcuucug uuagccacug                                            20

<210> SEQ ID NO 127
<211> LENGTH: 20
<212> TYPE: RNA
<213> ORGANISM: Artificial Sequence
<220> FEATURE:
<223> OTHER INFORMATION: oligonucleotide

<400> SEQUENCE: 127
uucagcuucu guuagccacu                                            20

<210> SEQ ID NO 128
<211> LENGTH: 21
<212> TYPE: RNA
<213> ORGANISM: Artificial Sequence
<220> FEATURE:

<223> OTHER INFORMATION: oligonucleotide

<400> SEQUENCE: 128
uucagcuucu guuagccacu g							21

<210> SEQ ID NO 129
<211> LENGTH: 21
<212> TYPE: RNA
<213> ORGANISM: Artificial Sequence
<220> FEATURE:
<223> OTHER INFORMATION: oligonucleotide

<400> SEQUENCE: 129
ucagcuucug uuagccacug a							21

<210> SEQ ID NO 130
<211> LENGTH: 22
<212> TYPE: RNA
<213> ORGANISM: Artificial Sequence
<220> FEATURE:
<223> OTHER INFORMATION: oligonucleotide

<400> SEQUENCE: 130
uucagcuucu guuagccacu ga						22

<210> SEQ ID NO 131
<211> LENGTH: 21
<212> TYPE: RNA
<213> ORGANISM: Artificial Sequence
<220> FEATURE:
<223> OTHER INFORMATION: oligonucleotide

<400> SEQUENCE: 131
ucagcuucug uuagccacug a							21

<210> SEQ ID NO 132
<211> LENGTH: 22
<212> TYPE: RNA
<213> ORGANISM: Artificial Sequence
<220> FEATURE:
<223> OTHER INFORMATION: oligonucleotide

<400> SEQUENCE: 132
uucagcuucu guuagccacu ga						22

<210> SEQ ID NO 133
<211> LENGTH: 22
<212> TYPE: RNA
<213> ORGANISM: Artificial Sequence
<220> FEATURE:
<223> OTHER INFORMATION: oligonucleotide

<400> SEQUENCE: 133
ucagcuucug uuagccacug au						22

<210> SEQ ID NO 134
<211> LENGTH: 23
<212> TYPE: RNA
<213> ORGANISM: Artificial Sequence
<220> FEATURE:
<223> OTHER INFORMATION: oligonucleotide

<400> SEQUENCE: 134
uucagcuucu guuagccacu gau						23

```
<210> SEQ ID NO 135
<211> LENGTH: 23
<212> TYPE: RNA
<213> ORGANISM: Artificial Sequence
<220> FEATURE:
<223> OTHER INFORMATION: oligonucleotide

<400> SEQUENCE: 135
ucagcuucug uuagccacug auu                                            23

<210> SEQ ID NO 136
<211> LENGTH: 24
<212> TYPE: RNA
<213> ORGANISM: Artificial Sequence
<220> FEATURE:
<223> OTHER INFORMATION: oligonucleotide

<400> SEQUENCE: 136
uucagcuucu guuagccacu gauu                                           24

<210> SEQ ID NO 137
<211> LENGTH: 24
<212> TYPE: RNA
<213> ORGANISM: Artificial Sequence
<220> FEATURE:
<223> OTHER INFORMATION: oligonucleotide

<400> SEQUENCE: 137
ucagcuucug uuagccacug auua                                           24

<210> SEQ ID NO 138
<211> LENGTH: 24
<212> TYPE: RNA
<213> ORGANISM: Artificial Sequence
<220> FEATURE:
<223> OTHER INFORMATION: oligonucleotide

<400> SEQUENCE: 138
uucagcuucu guuagccacu gaua                                           24

<210> SEQ ID NO 139
<211> LENGTH: 25
<212> TYPE: RNA
<213> ORGANISM: Artificial Sequence
<220> FEATURE:
<223> OTHER INFORMATION: oligonucleotide

<400> SEQUENCE: 139
ucagcuucug uuagccacug auuaa                                          25

<210> SEQ ID NO 140
<211> LENGTH: 26
<212> TYPE: RNA
<213> ORGANISM: Artificial Sequence
<220> FEATURE:
<223> OTHER INFORMATION: oligonucleotide

<400> SEQUENCE: 140
uucagcuucu guuagccacu gauuaa                                         26

<210> SEQ ID NO 141
<211> LENGTH: 26
<212> TYPE: RNA
<213> ORGANISM: Artificial Sequence
<220> FEATURE:
<223> OTHER INFORMATION: oligonucleotide
```

```
<400> SEQUENCE: 141
ucagcuucug uuagccacug auuaaa                                      26

<210> SEQ ID NO 142
<211> LENGTH: 27
<212> TYPE: RNA
<213> ORGANISM: Artificial Sequence
<220> FEATURE:
<223> OTHER INFORMATION: oligonucleotide

<400> SEQUENCE: 142
uucagcuucu guuagccacu gauuaaa                                     27

<210> SEQ ID NO 143
<211> LENGTH: 19
<212> TYPE: RNA
<213> ORGANISM: Artificial Sequence
<220> FEATURE:
<223> OTHER INFORMATION: oligonucleotide

<400> SEQUENCE: 143
cagcuucugu uagccacug                                              19

<210> SEQ ID NO 144
<211> LENGTH: 21
<212> TYPE: RNA
<213> ORGANISM: Artificial Sequence
<220> FEATURE:
<223> OTHER INFORMATION: oligonucleotide

<400> SEQUENCE: 144
cagcuucugu uagccacuga u                                           21

<210> SEQ ID NO 145
<211> LENGTH: 21
<212> TYPE: RNA
<213> ORGANISM: Artificial Sequence
<220> FEATURE:
<223> OTHER INFORMATION: oligonucleotide

<400> SEQUENCE: 145
agcuucuguu agccacugau u                                           21

<210> SEQ ID NO 146
<211> LENGTH: 22
<212> TYPE: RNA
<213> ORGANISM: Artificial Sequence
<220> FEATURE:
<223> OTHER INFORMATION: oligonucleotide

<400> SEQUENCE: 146
cagcuucugu uagccacuga uu                                          22

<210> SEQ ID NO 147
<211> LENGTH: 22
<212> TYPE: RNA
<213> ORGANISM: Artificial Sequence
<220> FEATURE:
<223> OTHER INFORMATION: oligonucleotide

<400> SEQUENCE: 147
agcuucuguu agccacugau ua                                          22

<210> SEQ ID NO 148
<211> LENGTH: 23
```

```
<212> TYPE: RNA
<213> ORGANISM: Artificial Sequence
<220> FEATURE:
<223> OTHER INFORMATION: oligonculeotide

<400> SEQUENCE: 148
cagcuucugu uagccacuga uua                                               23

<210> SEQ ID NO 149
<211> LENGTH: 23
<212> TYPE: RNA
<213> ORGANISM: Artificial Sequence
<220> FEATURE:
<223> OTHER INFORMATION: oligonucleotide

<400> SEQUENCE: 149
agcuucuguu agccacugau uaa                                               23

<210> SEQ ID NO 150
<211> LENGTH: 24
<212> TYPE: RNA
<213> ORGANISM: Artificial Sequence
<220> FEATURE:
<223> OTHER INFORMATION: oligonucleotide

<400> SEQUENCE: 150
cagcuucugu uagccacuga uuaa                                              24

<210> SEQ ID NO 151
<211> LENGTH: 24
<212> TYPE: RNA
<213> ORGANISM: Artificial Sequence
<220> FEATURE:
<223> OTHER INFORMATION: oligonucleotide

<400> SEQUENCE: 151
agcuucuguu agccacugau uaaa                                              24

<210> SEQ ID NO 152
<211> LENGTH: 25
<212> TYPE: RNA
<213> ORGANISM: Artificial Sequence
<220> FEATURE:
<223> OTHER INFORMATION: oligonucleotide

<400> SEQUENCE: 152
cagcuucugu uagccacuga uuaaa                                             25

<210> SEQ ID NO 153
<211> LENGTH: 24
<212> TYPE: RNA
<213> ORGANISM: Artificial Sequence
<220> FEATURE:
<223> OTHER INFORMATION: oligonucleotide

<400> SEQUENCE: 153
agcuucuguu agccacugau uaaa                                              24

<210> SEQ ID NO 154
<211> LENGTH: 20
<212> TYPE: RNA
<213> ORGANISM: Artificial Sequence
<220> FEATURE:
<223> OTHER INFORMATION: oligonucleotide

<400> SEQUENCE: 154
```
agcuucuguu agccacugau                                            20

<210> SEQ ID NO 155
<211> LENGTH: 20
<212> TYPE: RNA
<213> ORGANISM: Artificial Sequence
<220> FEATURE:
<223> OTHER INFORMATION: oligonucleotide

<400> SEQUENCE: 155
gcuucuguua gccacugauu                                            20

<210> SEQ ID NO 156
<211> LENGTH: 21
<212> TYPE: RNA
<213> ORGANISM: Artificial Sequence
<220> FEATURE:
<223> OTHER INFORMATION: oligonucleotide

<400> SEQUENCE: 156
agcuucuguu agccacugau u                                          21

<210> SEQ ID NO 157
<211> LENGTH: 21
<212> TYPE: RNA
<213> ORGANISM: Artificial Sequence
<220> FEATURE:
<223> OTHER INFORMATION: oligonucleotide

<400> SEQUENCE: 157
gcuucuguua gccacugauu a                                          21

<210> SEQ ID NO 158
<211> LENGTH: 22
<212> TYPE: RNA
<213> ORGANISM: Artificial Sequence
<220> FEATURE:
<223> OTHER INFORMATION: oligonculeotide

<400> SEQUENCE: 158
agcuucuguu agccacugau ua                                         22

<210> SEQ ID NO 159
<211> LENGTH: 22
<212> TYPE: RNA
<213> ORGANISM: Artificial Sequence
<220> FEATURE:
<223> OTHER INFORMATION: oligonucleotide

<400> SEQUENCE: 159
gcuucuguua gccacugauu aa                                         22

<210> SEQ ID NO 160
<211> LENGTH: 23
<212> TYPE: RNA
<213> ORGANISM: Artificial Sequence
<220> FEATURE:
<223> OTHER INFORMATION: oligonucleotide

<400> SEQUENCE: 160
agcuucuguu agccacugau uaa                                        23

<210> SEQ ID NO 161
<211> LENGTH: 23
<212> TYPE: RNA
<213> ORGANISM: Artificial Sequence

```
<220> FEATURE:
<223> OTHER INFORMATION: oligonucleotide

<400> SEQUENCE: 161
gcuucuguua gccacugauu aaa                                            23

<210> SEQ ID NO 162
<211> LENGTH: 24
<212> TYPE: RNA
<213> ORGANISM: Artificial Sequence
<220> FEATURE:
<223> OTHER INFORMATION: oligonucleotide

<400> SEQUENCE: 162
agcuucuguu agccacugau uaaa                                           24

<210> SEQ ID NO 163
<211> LENGTH: 23
<212> TYPE: RNA
<213> ORGANISM: Artificial Sequence
<220> FEATURE:
<223> OTHER INFORMATION: oligonucleotide

<400> SEQUENCE: 163
gcuucuguua gccacugauu aaa                                            23

<210> SEQ ID NO 164
<211> LENGTH: 23
<212> TYPE: RNA
<213> ORGANISM: Artificial Sequence
<220> FEATURE:
<223> OTHER INFORMATION: oligonucleotide

<400> SEQUENCE: 164
ccauuuguau uuagcauguu ccc                                            23

<210> SEQ ID NO 165
<211> LENGTH: 20
<212> TYPE: RNA
<213> ORGANISM: Artificial Sequence
<220> FEATURE:
<223> OTHER INFORMATION: oligonucleotide

<400> SEQUENCE: 165
agauaccauu uguauuuagc                                                20

<210> SEQ ID NO 166
<211> LENGTH: 19
<212> TYPE: RNA
<213> ORGANISM: Artificial Sequence
<220> FEATURE:
<223> OTHER INFORMATION: oligonucleotide

<400> SEQUENCE: 166
gccauuucuc aacagaucu                                                 19

<210> SEQ ID NO 167
<211> LENGTH: 23
<212> TYPE: RNA
<213> ORGANISM: Artificial Sequence
<220> FEATURE:
<223> OTHER INFORMATION: oligonucleotide

<400> SEQUENCE: 167
gccauuucuc aacagaucug uca                                            23
```

```
<210> SEQ ID NO 168
<211> LENGTH: 23
<212> TYPE: RNA
<213> ORGANISM: Artificial Sequence
<220> FEATURE:
<223> OTHER INFORMATION: oligonucleotide

<400> SEQUENCE: 168
auucucagga auugugucu uuc                                              23

<210> SEQ ID NO 169
<211> LENGTH: 21
<212> TYPE: RNA
<213> ORGANISM: Artificial Sequence
<220> FEATURE:
<223> OTHER INFORMATION: oligonucleotide

<400> SEQUENCE: 169
ucucaggaau uugugucuuu c                                               21

<210> SEQ ID NO 170
<211> LENGTH: 18
<212> TYPE: RNA
<213> ORGANISM: Artificial Sequence
<220> FEATURE:
<223> OTHER INFORMATION: oligonucleotide

<400> SEQUENCE: 170
guucagcuuc uguuagcc                                                   18

<210> SEQ ID NO 171
<211> LENGTH: 21
<212> TYPE: RNA
<213> ORGANISM: Artificial Sequence
<220> FEATURE:
<223> OTHER INFORMATION: oligonucleotide

<400> SEQUENCE: 171
cugauuaaau aucuuuauau c                                               21

<210> SEQ ID NO 172
<211> LENGTH: 18
<212> TYPE: RNA
<213> ORGANISM: Artificial Sequence
<220> FEATURE:
<223> OTHER INFORMATION: oligonucleotide

<400> SEQUENCE: 172
gccgccauuu cucaacag                                                   18

<210> SEQ ID NO 173
<211> LENGTH: 18
<212> TYPE: RNA
<213> ORGANISM: Artificial Sequence
<220> FEATURE:
<223> OTHER INFORMATION: oligonucleotide

<400> SEQUENCE: 173
guauuuagca uguuccca                                                   18

<210> SEQ ID NO 174
<211> LENGTH: 18
<212> TYPE: RNA
<213> ORGANISM: Artificial Sequence
<220> FEATURE:
<223> OTHER INFORMATION: oligonucleotide
```

<400> SEQUENCE: 174
caggaauuug ugucuuuc                                                       18

<210> SEQ ID NO 175
<211> LENGTH: 25
<212> TYPE: RNA
<213> ORGANISM: Artificial Sequence
<220> FEATURE:
<223> OTHER INFORMATION: oligonucleotide

<400> SEQUENCE: 175
gcuuuucuuu uaguugcugc ucuuu                                               25

<210> SEQ ID NO 176
<211> LENGTH: 25
<212> TYPE: RNA
<213> ORGANISM: Artificial Sequence
<220> FEATURE:
<223> OTHER INFORMATION: oligonucleotide

<400> SEQUENCE: 176 cuuucuuuu aguugcugcu cuuuu                                                25

<210> SEQ ID NO 177
<211> LENGTH: 25
<212> TYPE: RNA
<213> ORGANISM: Artificial Sequence
<220> FEATURE:
<223> OTHER INFORMATION: oligonucleotide

<400> SEQUENCE: 177
uuuucuuuua guugcugcuc uuuuc                                               25

<210> SEQ ID NO 178
<211> LENGTH: 25
<212> TYPE: RNA
<213> ORGANISM: Artificial Sequence
<220> FEATURE:
<223> OTHER INFORMATION: oligonucleotide

<400> SEQUENCE: 178
uuucuuuuag uugcugcucu uuucc                                               25

<210> SEQ ID NO 179
<211> LENGTH: 25
<212> TYPE: RNA
<213> ORGANISM: Artificial Sequence
<220> FEATURE:
<223> OTHER INFORMATION: oligonucleotide

<400> SEQUENCE: 179
uucuuuuagu ugcugcucuu uucca                                               25

<210> SEQ ID NO 180
<211> LENGTH: 25
<212> TYPE: RNA
<213> ORGANISM: Artificial Sequence
<220> FEATURE:
<223> OTHER INFORMATION: oligonucleotide

<400> SEQUENCE: 180
ucuuuuaguu gcugcucuuu uccag                                               25

<210> SEQ ID NO 181

```
<211> LENGTH: 25
<212> TYPE: RNA
<213> ORGANISM: Artificial Sequence
<220> FEATURE:
<223> OTHER INFORMATION: oligonucleotide

<400> SEQUENCE: 181
cuuuuaguug cugcucuuuu ccagg                                              25

<210> SEQ ID NO 182
<211> LENGTH: 25
<212> TYPE: RNA
<213> ORGANISM: Artificial Sequence
<220> FEATURE:
<223> OTHER INFORMATION: oligonucleotide

<400> SEQUENCE: 182
uuuuaguugc ugcucuuuuc caggu                                              25

<210> SEQ ID NO 183
<211> LENGTH: 25
<212> TYPE: RNA
<213> ORGANISM: Artificial Sequence
<220> FEATURE:
<223> OTHER INFORMATION: oligonucleotide

<400> SEQUENCE: 183
uuuaguugcu gcucuuuucc agguu                                              25

<210> SEQ ID NO 184
<211> LENGTH: 25
<212> TYPE: RNA
<213> ORGANISM: Artificial Sequence
<220> FEATURE:
<223> OTHER INFORMATION: oligonucleotide

<400> SEQUENCE: 184
uuaguugcug cucuuuucca gguuc                                              25

<210> SEQ ID NO 185
<211> LENGTH: 25
<212> TYPE: RNA
<213> ORGANISM: Artificial Sequence
<220> FEATURE:
<223> OTHER INFORMATION: oligonucleotide

<400> SEQUENCE: 185
uaguugcugc ucuuuuccag guuca                                              25

<210> SEQ ID NO 186
<211> LENGTH: 25
<212> TYPE: RNA
<213> ORGANISM: Artificial Sequence
<220> FEATURE:
<223> OTHER INFORMATION: oligonucleotide

<400> SEQUENCE: 186
aguugcugcu cuuuuccagg uucaa                                              25

<210> SEQ ID NO 187
<211> LENGTH: 25
<212> TYPE: RNA
<213> ORGANISM: Artificial Sequence
<220> FEATURE:
<223> OTHER INFORMATION: oligonucleotide

<400> SEQUENCE: 187
```

| | |
|---|---|
| guugcugcuc uuuuccaggu ucaag | 25 |

<210> SEQ ID NO 188
<211> LENGTH: 25
<212> TYPE: RNA
<213> ORGANISM: Artificial Sequence
<220> FEATURE:
<223> OTHER INFORMATION: oligonucleotide

<400> SEQUENCE: 188

| | |
|---|---|
| uugcugcucu uuuccagguu caagu | 25 |

<210> SEQ ID NO 189
<211> LENGTH: 25
<212> TYPE: RNA
<213> ORGANISM: Artificial Sequence
<220> FEATURE:
<223> OTHER INFORMATION: oligonucleotide

<400> SEQUENCE: 189

| | |
|---|---|
| ugcugcucuu uuccagguuc aagug | 25 |

<210> SEQ ID NO 190
<211> LENGTH: 25
<212> TYPE: RNA
<213> ORGANISM: Artificial Sequence
<220> FEATURE:
<223> OTHER INFORMATION: oligonucleotide

<400> SEQUENCE: 190

| | |
|---|---|
| gcugcucuuu uccagguuca agugg | 25 |

<210> SEQ ID NO 191
<211> LENGTH: 25
<212> TYPE: RNA
<213> ORGANISM: Artificial Sequence
<220> FEATURE:
<223> OTHER INFORMATION: oligonucleotide

<400> SEQUENCE: 191

| | |
|---|---|
| cugcucuuuu ccagguucaa guggg | 25 |

<210> SEQ ID NO 192
<211> LENGTH: 25
<212> TYPE: RNA
<213> ORGANISM: Artificial Sequence
<220> FEATURE:
<223> OTHER INFORMATION: oligonucleotide

<400> SEQUENCE: 192

| | |
|---|---|
| ugcucuuuuc cagguucaag uggga | 25 |

<210> SEQ ID NO 193
<211> LENGTH: 25
<212> TYPE: RNA
<213> ORGANISM: Artificial Sequence
<220> FEATURE:
<223> OTHER INFORMATION: oligonucleotide

<400> SEQUENCE: 193

| | |
|---|---|
| gcucuuuucc agguucaagu gggac | 25 |

<210> SEQ ID NO 194
<211> LENGTH: 25
<212> TYPE: RNA

```
<213> ORGANISM: Artificial Sequence
<220> FEATURE:
<223> OTHER INFORMATION: oligonucleotide

<400> SEQUENCE: 194
cucuuuucca gguucaagug ggaua                                        25

<210> SEQ ID NO 195
<211> LENGTH: 25
<212> TYPE: RNA
<213> ORGANISM: Artificial Sequence
<220> FEATURE:
<223> OTHER INFORMATION: oligonucleotide

<400> SEQUENCE: 195
ucuuuuccag guucaagugg gauac                                        25

<210> SEQ ID NO 196
<211> LENGTH: 25
<212> TYPE: RNA
<213> ORGANISM: Artificial Sequence
<220> FEATURE:
<223> OTHER INFORMATION: oligonucleotide

<400> SEQUENCE: 196
cuuuuccagg uucaaguggg auacu                                        25

<210> SEQ ID NO 197
<211> LENGTH: 25
<212> TYPE: RNA
<213> ORGANISM: Artificial Sequence
<220> FEATURE:
<223> OTHER INFORMATION: oligonucleotide

<400> SEQUENCE: 197
uuuuccaggu ucaaguggga uacua                                        25

<210> SEQ ID NO 198
<211> LENGTH: 25
<212> TYPE: RNA
<213> ORGANISM: Artificial Sequence
<220> FEATURE:
<223> OTHER INFORMATION: oligonucleotide

<400> SEQUENCE: 198
uuuccagguu caagugggau acuag                                        25

<210> SEQ ID NO 199
<211> LENGTH: 25
<212> TYPE: RNA
<213> ORGANISM: Artificial Sequence
<220> FEATURE:
<223> OTHER INFORMATION: oligonucleotide

<400> SEQUENCE: 199
uuccagguuc aagugggaua cuagc                                        25

<210> SEQ ID NO 200
<211> LENGTH: 25
<212> TYPE: RNA
<213> ORGANISM: Artificial Sequence
<220> FEATURE:
<223> OTHER INFORMATION: oligonucleotide

<400> SEQUENCE: 200
uccagguuca agugggauac uagca                                        25
```

```
<210> SEQ ID NO 201
<211> LENGTH: 25
<212> TYPE: RNA
<213> ORGANISM: Artificial Sequence
<220> FEATURE:
<223> OTHER INFORMATION: oligonucleotide

<400> SEQUENCE: 201
ccagguucaa gugggauacu agcaa                                                25

<210> SEQ ID NO 202
<211> LENGTH: 25
<212> TYPE: RNA
<213> ORGANISM: Artificial Sequence
<220> FEATURE:
<223> OTHER INFORMATION: oligonucleotide

<400> SEQUENCE: 202
cagguucaag ugggauacua gcaau                                                25

<210> SEQ ID NO 203
<211> LENGTH: 25
<212> TYPE: RNA
<213> ORGANISM: Artificial Sequence
<220> FEATURE:
<223> OTHER INFORMATION: oligonucleotide

<400> SEQUENCE: 203
agguucaagu gggauacuag caaug                                                25

<210> SEQ ID NO 204
<211> LENGTH: 25
<212> TYPE: RNA
<213> ORGANISM: Artificial Sequence
<220> FEATURE:
<223> OTHER INFORMATION: oligonucleotide

<400> SEQUENCE: 204
gguucaagug ggauacuagc aaugu                                                25

<210> SEQ ID NO 205
<211> LENGTH: 25
<212> TYPE: RNA
<213> ORGANISM: Artificial Sequence
<220> FEATURE:
<223> OTHER INFORMATION: oligonucleotide

<400> SEQUENCE: 205
guucaagugg gauacuagca auguu                                                25

<210> SEQ ID NO 206
<211> LENGTH: 25
<212> TYPE: RNA
<213> ORGANISM: Artificial Sequence
<220> FEATURE:
<223> OTHER INFORMATION: oligonucleotide

<400> SEQUENCE: 206
uucaagnggg auacuagcaa uguua                                                25

<210> SEQ ID NO 207
<211> LENGTH: 25
<212> TYPE: RNA
<213> ORGANISM: Artificial Sequence
<220> FEATURE:
```

<223> OTHER INFORMATION: oligonucleotide

<400> SEQUENCE: 207
ucaaguggga uacuagcaau guuau                                              25

<210> SEQ ID NO 208
<211> LENGTH: 25
<212> TYPE: RNA
<213> ORGANISM: Artificial Sequence
<220> FEATURE:
<223> OTHER INFORMATION: oligonucleotide

<400> SEQUENCE: 208
caagugggau acuagcaaug uuauc                                              25

<210> SEQ ID NO 209
<211> LENGTH: 25
<212> TYPE: RNA
<213> ORGANISM: Artificial Sequence
<220> FEATURE:
<223> OTHER INFORMATION: oligonucleotide

<400> SEQUENCE: 209
aagugggaua cuagcaaugu uaucu                                              25

<210> SEQ ID NO 210
<211> LENGTH: 25
<212> TYPE: RNA
<213> ORGANISM: Artificial Sequence
<220> FEATURE:
<223> OTHER INFORMATION: oligonucleotide

<400> SEQUENCE: 210
agugggauac uagcaauguu aucug                                              25

<210> SEQ ID NO 211
<211> LENGTH: 25
<212> TYPE: RNA
<213> ORGANISM: Artificial Sequence
<220> FEATURE:
<223> OTHER INFORMATION: oligonucleotide

<400> SEQUENCE: 211
gugggauacu agcaauguua ucugc                                              25

<210> SEQ ID NO 212
<211> LENGTH: 25
<212> TYPE: RNA
<213> ORGANISM: Artificial Sequence
<220> FEATURE:
<223> OTHER INFORMATION: oligonucleotide

<400> SEQUENCE: 212
ugggauacua gcaauguuau cugcu                                              25

<210> SEQ ID NO 213
<211> LENGTH: 25
<212> TYPE: RNA
<213> ORGANISM: Artificial Sequence
<220> FEATURE:
<223> OTHER INFORMATION: oligonucleotide

<400> SEQUENCE: 213
gggauacuag caauguuauc ugcuu                                              25

```
<210> SEQ ID NO 214
<211> LENGTH: 25
<212> TYPE: RNA
<213> ORGANISM: Artificial Sequence
<220> FEATURE:
<223> OTHER INFORMATION: oligonucleotide

<400> SEQUENCE: 214
ggauacuagc aauguuaucu gcuuc                                      25

<210> SEQ ID NO 215
<211> LENGTH: 25
<212> TYPE: RNA
<213> ORGANISM: Artificial Sequence
<220> FEATURE:
<223> OTHER INFORMATION: oligonucleotide

<400> SEQUENCE: 215
gauacuagca auguuaucug cuucc                                      25

<210> SEQ ID NO 216
<211> LENGTH: 25
<212> TYPE: RNA
<213> ORGANISM: Artificial Sequence
<220> FEATURE:
<223> OTHER INFORMATION: oligonucleotide

<400> SEQUENCE: 216
auacuagcaa uguuaucugc uuccu                                      25

<210> SEQ ID NO 217
<211> LENGTH: 25
<212> TYPE: RNA
<213> ORGANISM: Artificial Sequence
<220> FEATURE:
<223> OTHER INFORMATION: oligonucleotide

<400> SEQUENCE: 217
uacuagcaau guuaucugcu uccuc                                      25

<210> SEQ ID NO 218
<211> LENGTH: 25
<212> TYPE: RNA
<213> ORGANISM: Artificial Sequence
<220> FEATURE:
<223> OTHER INFORMATION: oligonucleotide

<400> SEQUENCE: 218
acuagcaaug uuaucugcuu ccucc                                      25

<210> SEQ ID NO 219
<211> LENGTH: 25
<212> TYPE: RNA
<213> ORGANISM: Artificial Sequence
<220> FEATURE:
<223> OTHER INFORMATION: oligonucleotide

<400> SEQUENCE: 219
cuagcaaugu uaucugcuuc cucca                                      25

<210> SEQ ID NO 220
<211> LENGTH: 25
<212> TYPE: RNA
<213> ORGANISM: Artificial Sequence
<220> FEATURE:
<223> OTHER INFORMATION: oligonucleotide
```

```
<400> SEQUENCE: 220
uagcaauguu aucugcuucc uccaa                                      25

<210> SEQ ID NO 221
<211> LENGTH: 25
<212> TYPE: RNA
<213> ORGANISM: Artificial Sequence
<220> FEATURE:
<223> OTHER INFORMATION: oligonucleotide

<400> SEQUENCE: 221
agcaauguua ucugcuuccu ccaac                                      25

<210> SEQ ID NO 222
<211> LENGTH: 25
<212> TYPE: RNA
<213> ORGANISM: Artificial Sequence
<220> FEATURE:
<223> OTHER INFORMATION: oligonucleotide

<400> SEQUENCE: 222
gcaauguuau cugcuuccuc caacc                                      25

<210> SEQ ID NO 223
<211> LENGTH: 25
<212> TYPE: RNA
<213> ORGANISM: Artificial Sequence
<220> FEATURE:
<223> OTHER INFORMATION: oligonucleotide

<400> SEQUENCE: 223
caauguuauc ugcuuccucc aacca                                      25

<210> SEQ ID NO 224
<211> LENGTH: 25
<212> TYPE: RNA
<213> ORGANISM: Artificial Sequence
<220> FEATURE:
<223> OTHER INFORMATION: oligonucleotide

<400> SEQUENCE: 224
aauguuaucu gcuuccucca accau                                      25

<210> SEQ ID NO 225
<211> LENGTH: 25
<212> TYPE: RNA
<213> ORGANISM: Artificial Sequence
<220> FEATURE:
<223> OTHER INFORMATION: oligonucleotide

<400> SEQUENCE: 225
auguuaucug cuuccuccaa ccaua                                      25

<210> SEQ ID NO 226
<211> LENGTH: 25
<212> TYPE: RNA
<213> ORGANISM: Artificial Sequence
<220> FEATURE:
<223> OTHER INFORMATION: oligonucleotide

<400> SEQUENCE: 226
uguuaucugc uuccuccaac cauaa                                      25

<210> SEQ ID NO 227
<211> LENGTH: 25
```

<212> TYPE: RNA
<213> ORGANISM: Artificial Sequence
<220> FEATURE:
<223> OTHER INFORMATION: oligonucleotide

<400> SEQUENCE: 227
guuaucugcu uccuccaacc auaaa                                        25

<210> SEQ ID NO 228
<211> LENGTH: 19
<212> TYPE: RNA
<213> ORGANISM: Artificial Sequence
<220> FEATURE:
<223> OTHER INFORMATION: oligonucleotide

<400> SEQUENCE: 228
gcugcucuuu uccagguuc                                               19

<210> SEQ ID NO 229
<211> LENGTH: 20
<212> TYPE: RNA
<213> ORGANISM: Artificial Sequence
<220> FEATURE:
<223> OTHER INFORMATION: oligonucleotide

<400> SEQUENCE: 229
ucuuuuccag guucaagugg                                              20

<210> SEQ ID NO 230
<211> LENGTH: 19
<212> TYPE: RNA
<213> ORGANISM: Artificial Sequence
<220> FEATURE:
<223> OTHER INFORMATION: oligonucleotide

<400> SEQUENCE: 230
agguucaagu gggauacua                                               19

<210> SEQ ID NO 231
<211> LENGTH: 21
<212> TYPE: RNA
<213> ORGANISM: Artificial Sequence
<220> FEATURE:
<223> OTHER INFORMATION: oligonucleotide

<400> SEQUENCE: 231
caauuuuucc cacucaguau u                                            21

<210> SEQ ID NO 232
<211> LENGTH: 19
<212> TYPE: RNA
<213> ORGANISM: Artificial Sequence
<220> FEATURE:
<223> OTHER INFORMATION: oligonucleotide

<400> SEQUENCE: 232
uugaaguucc uggagucuu                                               19

<210> SEQ ID NO 233
<211> LENGTH: 22
<212> TYPE: RNA
<213> ORGANISM: Artificial Sequence
<220> FEATURE:
<223> OTHER INFORMATION: oligonucleotide

<400> SEQUENCE: 233

```
uccucaggag gcagcucuaa au                                              22

<210> SEQ ID NO 234
<211> LENGTH: 26
<212> TYPE: RNA
<213> ORGANISM: Artificial Sequence
<220> FEATURE:
<223> OTHER INFORMATION: oligonucleotide

<400> SEQUENCE: 234
gcgcugguca caaaauccug uugaac                                          26

<210> SEQ ID NO 235
<211> LENGTH: 27
<212> TYPE: RNA
<213> ORGANISM: Artificial Sequence
<220> FEATURE:
<223> OTHER INFORMATION: oligonucleotide

<400> SEQUENCE: 235
cacuugcuug aaaaggucua caaagga                                         27

<210> SEQ ID NO 236
<211> LENGTH: 26
<212> TYPE: RNA
<213> ORGANISM: Artificial Sequence
<220> FEATURE:
<223> OTHER INFORMATION: oligonucleotide

<400> SEQUENCE: 236
ggugaauaac uuacaaauuu ggaagc                                          26
```

METHODS AND MEANS FOR EFFICIENT SKIPPING OF EXON 45 IN DUCHENNE MUSCULAR DYSTROPHY PRE-MRNA

This application is a continuation application of U.S. application Ser. No. 16/283,458, filed Feb. 22, 2019, which is a continuation application of U.S. application Ser. Nos. 16/229,821 and 16/229,534, each filed Dec. 21, 2018, which are continuation applications of U.S. application Ser. No. 15/390,836, filed Dec. 27, 2016, which is a continuation application of U.S. application Ser. No. 14/542,183, filed Nov. 14, 2014, now U.S. Pat. No. 9,528,109, which is a continuation application of U.S. application Ser. No. 14/200,251, filed Mar. 7, 2014, which is a continuation application of U.S. application Ser. No. 14/134,971, filed Dec. 19, 2013, which is a continuation application of U.S. application Ser. No. 14/097,210, filed Dec. 4, 2013, which is a continuation application of U.S. application Ser. No. 13/094,548, filed Apr. 26, 2011, now U.S. Pat. No. 9,926,557, which is a continuation application of International Patent Application No. PCT/NL2009/050006 filed Jan. 13, 2009, which is a continuation-in-part application of International Patent Application No. PCT/NL2008/050673 filed Oct. 27, 2008.

FIELD

The invention relates to the field of genetics, more specifically human genetics. The invention in particular relates to the modulation of splicing of the human Duchenne Muscular Dystrophy pre-mRNA.

BACKGROUND OF THE INVENTION

Myopathies are disorders that result in functional impairment of muscles. Muscular dystrophy (MD) refers to genetic diseases that are characterized by progressive weakness and degeneration of skeletal muscles. Duchenne muscular dystrophy (DMD) and Becker muscular dystrophy (BMD) are the most common childhood forms of muscular dystrophy. They are recessive disorders and because the gene responsible for DMD and BMD resides on the X-chromosome, mutations mainly affect males with an incidence of about 1 in 3500 boys.

DMD and BMD are caused by genetic defects in the DMD gene encoding dystrophin, a muscle protein that is required for interactions between the cytoskeleton and the extracellular matrix to maintain muscle fiber stability during contraction. DMD is a severe, lethal neuromuscular disorder resulting in a dependency on wheelchair support before the age of 12 and DMD patients often die before the age of thirty due to respiratory- or heart failure. In contrast, BMD patients often remain ambulatory until later in life, and have near normal life expectancies. DMD mutations in the DMD gene are mainly characterized by frame shifting insertions or deletions or nonsense point mutations, resulting in the absence of functional dystrophin. BMD mutations in general keep the reading frame intact, allowing synthesis of a partly functional dystrophin.

During the last decade, specific modification of splicing in order to restore the disrupted reading frame of the DMD transcript has emerged as a promising therapy for Duchenne muscular dystrophy (DMD) (van Ommen, van Deutekom, Aartsma-Rus, Curr Opin Mol Ther. 2008; 10(2):140-9, Yokota, Duddy, Partidge, Acta Myol. 2007; 26(3):179-84, van Deutekom et al., N Engl J Med. 2007; 357(26):2677-86).

Using antisense oligonucleotides (AONs) interfering with splicing signals the skipping of specific exons can be induced in the DMD pre-mRNA, thus restoring the open reading frame and converting the severe DMD into a milder BMD phenotype (van Deutekom et al. Hum Mol Genet. 2001; 10: 1547-54; Aartsma-Rus et al., Hum Mol Genet 2003; 12(8):907-14.). In vivo proof-of-concept was first obtained in the mdx mouse model, which is dystrophin-deficient due to a nonsense mutation in exon 23. Intramuscular and intravenous injections of AONs targeting the mutated exon 23 restored dystrophin expression for at least three months (Lu et al. Nat Med. 2003; 8: 1009-14; Lu et al., Proc Natl Acad Sci U S A. 2005; 102(1):198-203). This was accompanied by restoration of dystrophin-associated proteins at the fiber membrane as well as functional improvement of the treated muscle. In vivo skipping of human exons has also been achieved in the hDMD mouse model, which contains a complete copy of the human DMD gene integrated in chromosome 5 of the mouse (Bremmer-Bout et al. Molecular Therapy. 2004; 10: 232-40; 't Hoen et al. J Biol Chem. 2008; 283: 5899-907).

As the majority of DMD patients have deletions that cluster in hotspot regions, the skipping of a small number of exons is applicable to relatively large numbers of patients. The actual applicability of exon skipping can be determined for deletions, duplications and point mutations reported in DMD mutation databases such as the Leiden DMD mutation database available at www.dmd.nl. Therapeutic skipping of exon 45 of the DMD pre-mRNA would restore the open reading frame of DMD patients having deletions including but not limited to exons 12-44, 18-44, 44, 46, 46-47, 46-48, 46-49, 46-51, 46-53, 46-55, 46-59, 46-60 of the DMD pre-mRNA, occurring in a total of 16% of all DMD patients with a deletion (Aartsma-Rus and van Deutekom, 2007, Antisense Elements (Genetics) Research Focus, 2007 Nova Science Publishers, Inc). Furthermore, for some DMD patients the simultaneous skipping of one of more exons in addition to exon 45, such as exons 51 or 53 is required to restore the correct reading frame. None-limiting examples include patients with a deletion of exons 46-50 requiring the co-skipping of exons 45 and 51, or with a deletion of exons 46-52 requiring the co-skipping of exons 45 and 53.

Recently, a first-in-man study was successfully completed where an AON inducing the skipping of exon 51 was injected into a small area of the tibialis anterior muscle of four DMD patients. Novel dystrophin expression was observed in the majority of muscle fibers in all four patients treated, and the AON was safe and well tolerated (van Deutekom et al. N Engl J Med. 2007; 357: 2677-86).

Most AONs studied contain up to 20 nucleotides, and it has been argued that this relatively short size improves the tissue distribution and/or cell penetration of an AON. However, such short AONs will result in a limited specificity due to an increased risk for the presence of identical sequences elsewhere in the genome, and a limited target binding or target affinity due to a low free energy of the AON-target complex. Therefore the inventors decided to design new and optionally improved oligonucleotides that would not exhibit all of these drawbacks.

DESCRIPTION OF THE INVENTION

Method

In a first aspect, the invention provides a method for inducing and/or promoting skipping of exon 45 of DMD pre-mRNA in a patient, preferably in an isolated cell of said patient, the method comprising providing said cell and/or said patient with a molecule that binds to a continuous stretch of at least 21 nucleotides within said exon.

Accordingly, a method is herewith provided for inducing and/or promoting skipping of exon 45 of DMD pre-mRNA, preferably in an isolated cell of a patient, the method comprising providing said cell and/or said patient with a molecule that binds to a continuous stretch of at least 21 nucleotides within said exon.

It is to be understood that said method encompasses an in vitro, in vivo or ex vivo method.

As defined herein a DMD pre-mRNA preferably means the pre-mRNA of a DMD gene of a DMD or BMD patient. The DMD gene or protein corresponds to the dystrophin gene or protein.

A patient is preferably intended to mean a patient having DMD or BMD as later defined herein or a patient susceptible to develop DMD or BMD due to his or her genetic background.

Exon skipping refers to the induction in a cell of a mature mRNA that does not contain a particular exon that is normally present therein. Exon skipping is achieved by providing a cell expressing the pre-mRNA of said mRNA with a molecule capable of interfering with sequences such as, for example, the splice donor or splice acceptor sequence that are both required for allowing the enzymatic process of splicing, or a molecule that is capable of interfering with an exon inclusion signal required for recognition of a stretch of nucleotides as an exon to be included in the mRNA. The term pre-mRNA refers to a non-processed or partly processed precursor mRNA that is synthesized from a DNA template in the cell nucleus by transcription.

Within the context of the invention inducing and/or promoting skipping of an exon as indicated herein means that at least 1%, 10%, 20%, 30%, 40%, 50%, 60%, 70%, 80%, 90% or more of the DMD mRNA in one or more (muscle) cells of a treated patient will not contain said exon. This is preferably assessed by PCR as described in the examples.

Preferably, a method of the invention by inducing or promoting skipping of exon 45 of the DMD pre-mRNA in one or more cells of a patient provides said patient with a functional dystrophin protein and/or decreases the production of an aberrant dystrophin protein in said patient. Therefore a preferred method is a method, wherein a patient or a cell of said patient is provided with a functional dystrophin protein and/or wherein the production of an aberrant dystrophin protein in said patient or in a cell of said patient is decreased Decreasing the production of an aberrant dystrophin may be assessed at the mRNA level and preferably means that 99%, 90%, 80%, 70%, 60%, 50%, 40%, 30%, 20%, 10%, 5% or less of the initial amount of aberrant dystrophin mRNA, is still detectable by RT PCR. An aberrant dystrophin mRNA or protein is also referred to herein as a non-functional dystrophin mRNA or protein. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein.

Increasing the production of a functional dystrophin in said patient or in a cell of said patient may be assessed at the mRNA level (by RT-PCR analysis) and preferably means that a detectable amount of a functional dystrophin mRNA is detectable by RT PCR. In another embodiment, 1%, 5%, 10%, 20%, 30%, 40%, 50%, 60%, 70%, 80%, 90% or more of the detectable dystrophin mRNA is a functional dystrophin mRNA. Increasing the production of a functional dystrophin in said patient or in a cell of said patient may be assessed at the protein level (by immunofluorescence and western blot analyses) and preferably means that a detectable amount of a functional dystrophin protein is detectable by immunofluorescence or western blot analysis. In another embodiment, 1%, 5%, 10%, 20%/a, 30%, 40%, 50%, 60%, 70%, 80%, 90% or more of the detectable dystrophin protein is a functional dystrophin protein.

As defined herein, a functional dystrophin is preferably a wild type dystrophin corresponding to a protein having the amino acid sequence as identified in SEQ ID NO: 1. A functional dystrophin is preferably a dystrophin, which has an actin binding domain in its N terminal part (first 240 amino acids at the N terminus), a cystein-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO: 1. In other words, a functional dystrophin is a dystrophin which exhibits at least to some extent an activity of a wild type dystrophin. "At least to some extent" preferably means at least 10%, 20%, 30%, 40%, 50%, 60%, 70%, 80%, 90%, 95% or 100% of a corresponding activity of a wild type functional dystrophin. In this context, an activity of a functional dystrophin is preferably binding to actin and to the dystrophin-associated glycoprotein complex (DGC) (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). Binding of dystrophin to actin and to the DGC complex may be visualized by either co-immunoprecipitation using total protein extracts or immunofluorescence analysis of cross-sections, from a muscle biopsy, as known to the skilled person.

Individuals or patients suffering from Duchenne muscular dystrophy typically have a mutation in the DMD gene that prevent synthesis of the complete dystrophin protein, i.e of a premature stop prevents the synthesis of the C-terminus. In Becker muscular dystrophy the DMD gene also comprises a mutation compared to the wild type gene but the mutation does typically not induce a premature stop and the C-terminus is typically synthesized. As a result a functional dystrophin protein is synthesized that has at least the same activity in kind as the wild type protein, not although not necessarily the same amount of activity. The genome of a BMD individual typically encodes a dystrophin protein comprising the N terminal part (first 240 amino acids at the N terminus), a cystein-rich domain (amino acid 3361 till 3685) and a C terminal domain (last 325 amino acids at the C terminus) but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). Exon-skipping for the treatment of DMD is typically directed to overcome a premature stop in the pre-mRNA by skipping an exon in the rod-shaped domain to correct the reading frame and allow synthesis of the remainder of the dystrophin protein including the C-terminus, albeit that the protein is somewhat smaller as a result of a smaller rod domain. In a preferred embodiment, an individual having DMD and being treated by a method as defined herein will be provided a dystrophin which exhibits at least to some extent an activity of a wild type dystrophin. More preferably, if said individual is a Duchenne patient or is suspected to be a Duchenne patient, a functional dystrophin is a dystrophin of an individual having BMD: typically said dystrophin is able to interact with both actin and the DGC, but its central rod shaped domain may be shorter than the one of a wild type dystrophin (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). The central rod-shaped domain of wild type dystrophin comprises 24 spectrin-like repeats (Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144). For example, a central rod-shaped domain of a dystrophin as provided herein may comprise 5 to 23, 10 to 22 or 12 to 18 spectrin-like repeats as long as it can bind to actin and to DGC.

A method of the invention may alleviate one or more characteristics of a muscle cell from a DMD patient comprising deletions including but not limited to exons 12-44, 18-44, 44, 46, 46-47, 46-48, 46-49, 46-51, 46-53, 46-55, 46-59, 46-60 of the DMD pre-mRNA of said patient (Aartsma-Rus and van Deutekom, 2007, Antisense Elements (Genetics) Research Focus, 2007 Nova Science Publishers, Inc) as well as from DMD patients requiring the simultaneous skipping of one of more exons in addition to exon 45 including but not limited to patients with a deletion of exons 46-50 requiring the co-skipping of exons 45 and 51, or with a deletion of exons 46-52 requiring the co-skipping of exons 45 and 53.

In a preferred method, one or more symptom(s) or characteristic(s) of a myogenic cell or muscle cell from a DMD patient is/are alleviated. Such symptoms or characteristics may be assessed at the cellular, tissue level or on the patient self.

An alleviation of one or more symptoms or characteristics may be assessed by any of the following assays on a myogenic cell or muscle cell from a patient: reduced calcium uptake by muscle cells, decreased collagen synthesis, altered morphology, altered lipid biosynthesis, decreased oxidative stress, and/or improved muscle fiber function, integrity, and/or survival. These parameters are usually assessed using immunofluorescence and/or histochemical analyses of cross sections of muscle biopsies.

The improvement of muscle fiber function, integrity and/or survival may also be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person.

Creatine kinase may be detected in blood as described in Hodgetts et al (Hodgetts S., et al, (2006), Neuromuscular Disorders, 16: 591-602.2006). A detectable decrease in creatine kinase may mean a decrease of 5%, 10%, 20%, 30%, 40%, 50%, 60%, 70%, 80%, 90% or more compared to the concentration of creatine kinase in a same DMD patient before treatment.

A detectable decrease of necrosis of muscle fibers is preferably assessed in a muscle biopsy, more preferably as described in Hodgetts et al (Hodgetts S., et al, (2006), Neuromuscular Disorders, 16: 591-602.2006) using biopsy cross-sections. A detectable decrease of necrosis may be a decrease of 5%, 10%0/, 20%, 30%, 40%, 50%, 60%, 70%, 80%, 90% or more of the area wherein necrosis has been identified using biopsy cross-sections. The decrease is measured by comparison to the necrosis as assessed in a same DMD patient before treatment.

A detectable increase of the homogeneity of the diameter of muscle fibers is preferably assessed in a muscle biopsy cross-section, more preferably as described in Hodgetts et al (Hodgetts S., et al, (2006), Neuromuscular Disorders, 16: 591-602.2006). The increase is measured by comparison to the homogeneity of the diameter of muscle fibers in a muscle biopsy cross-section of a same DMD patient before treatment.

An alleviation of one or more symptoms or characteristics may be assessed by any of the following assays on the patient self: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur at al (Manzur A Y et al, (2008), Glucocorticoid corticosteroids for Duchenne muscular dystrophy (review), Wiley publishers, The Cochrane collaboration.) gives an extensive explanation of each of these assays. For each of these assays, as soon as a detectable improvement or prolongation of a parameter measured in an assay has been found, it will preferably mean that one or more symptoms of Duchenne Muscular Dystrophy has been alleviated in an individual using a method of the invention. Detectable improvement or prolongation is preferably a statistically significant improvement or prolongation as described in Hodgetts et al (Hodgetts S., et al, (2006), Neuromuscular Disorders, 16: 591-602.2006). Alternatively, the alleviation of one or more symptom(s) of Duchenne Muscular Dystrophy may be assessed by measuring an improvement of a muscle fiber function, integrity and/or survival as later defined herein.

A treatment in a method according to the invention may have a duration of at least one week, at least one month, at least several months, at least one year, at least 2, 3, 4, 5, 6 years or more. The frequency of administration of an oligonucleotide, composition, compound of the invention may depend on several parameters such as the age of the patient, the type of mutation, the number of molecules (dose), the formulation of said molecule. The frequency may be ranged between at least once in a two weeks, or three weeks or four weeks or five weeks or a longer time period. Each molecule or oligonucleotide or equivalent thereof as defined herein for use according to the invention may be suitable for direct administration to a cell, tissue and/or an organ in vivo of individuals affected by or at risk of developing DMD and may be administered directly in vivo, ex vivo or in vitro. An oligonucleotide as used herein may be suitable for administration to a cell, tissue and/or an organ in vivo of individuals affected by or at risk of developing DMD, and may be administered in vivo, ex vivo or in vitro. Said oligonucleotide may be directly or indirectly administered to a cell, tissue and/or an organ in vivo of an individual affected by or at risk of developing DMD, and may be administered directly or indirectly in vivo, ex vivo or in vitro. As Duchenne muscular dystrophy has a pronounced phenotype in muscle cells, it is preferred that said cells are muscle cells, it is further preferred that said tissue is a muscular tissue and/or it is further preferred that said organ comprises or consists of a muscular tissue. A preferred organ is the heart.

Preferably said cells comprise a gene encoding a mutant dystrophin protein. Preferably said cells are cells of an individual suffering from DMD.

A molecule or oligonucleotide or equivalent thereof can be delivered as is to a cell. When administering said molecule, oligonucleotide or equivalent thereof to an individual, it is preferred that it is dissolved in a solution that is compatible with the delivery method. For intravenous, subcutaneous, intramuscular, intrathecal and/or intraventricular administration it is preferred that the solution is a physiological salt solution. Particularly preferred for a method of the invention is the use of an excipient that will further enhance delivery of said molecule, oligonucleotide or functional equivalent thereof as defined herein, to a cell and into a cell, preferably a muscle cell. Preferred excipient are defined in the section entitled "pharmaceutical composition". In vitro, we obtained very good results using polyethylenimine (PEI, ExGen500, MBI Fermentas) as shown in the example.

In a preferred method of the invention, an additional molecule is used which is able to induce and/or promote skipping of a distinct exon of the DMD pre-mRNA of a patient. Preferably, the second exon is selected from: exon 7, 44, 46, 51, 53, 59, 67 of the dystrophin pre-mRNA of a patient. Molecules which can be used are depicted in table 2. Preferred molecules comprise or consist of any of the oligonucleotides as disclosed in table 2. Several oligonucleotides may also be used in combination. This way, inclusion of two or more exons of a DMD pre-mRNA in mRNA produced from this pre-mRNA is prevented. This embodiment is further referred to as double- or multi-exon skipping (Aartsma-Rus A, Janson A A, Kaman W E, et al. Antisense-induced multiexon skipping for Duchenne muscular dystrophy makes more sense. Am J Hum Genet 2004; 74(1):83-92, Aartsma-Rus A, Kaman W E, Weij R, den Dunnen J T, van Ommen G J, van Deutekom J C. Exploring the frontiers of therapeutic exon skipping for Duchenne muscular dystrophy by double targeting within one or multiple exons. Mol Ther 2006; 14(3):401-7). In most cases double-exon skipping results in the exclusion of only the two targeted exons from the dystrophin pre-mRNA. However, in other cases it was found that the targeted exons and the entire region in between said exons in said pre-mRNA were not present in the produced mRNA even when other exons (intervening exons) were present in such region. This multi-skipping was notably so for the combination of oligonucleotides derived from the DMD gene, wherein one oligonucleotide for exon 45 and one oligonucleotide for exon 51 was added to a cell transcribing the DMD gene. Such a set-up resulted in mRNA being produced that did not contain exons 45 to 51. Apparently, the structure of the pre-mRNA in the presence of the mentioned oligonucleotides was such that the splicing machinery was stimulated to connect exons 44 and 52 to each other.

It is possible to specifically promote the skipping of also the intervening exons by providing a linkage between the two complementary oligonucleotides. Hence, in one embodiment stretches of nucleotides complementary to at least two dystrophin exons are separated by a linking moiety. The at least two stretches of nucleotides are thus linked in this embodiment so as to form a single molecule.

In case, more than one compounds are used in a method of the invention, said compounds can be administered to an individual in any order. In one embodiment, said compounds are administered simultaneously (meaning that said compounds are administered within 10 hours, preferably within one hour). This is however not necessary. In another embodiment, said compounds are administered sequentially.

Molecule

In a second aspect, there is provided a molecule for use in a method as described in the previous section entitled "Method". This molecule preferably comprises or consists of an oligonucleotide, Said oligonucleotide is preferably an antisense oligonucleotide (AON) or antisense oligoribonucleotide.

It was found by the present investigators that especially exon 45 is specifically skipped at a high frequency using a molecule that binds to a continuous stretch of at least 21 nucleotides within said exon. Although this effect can be associated with a higher binding affinity of said molecule, compared to a molecule that binds to a continuous stretch of less than 21 nucleotides, there could be other intracellular parameters involved that favor thermodynamic, kinetic, or structural characteristics of the hybrid duplex. In a preferred embodiment, a molecule that binds to a continuous stretch of at least 21, 25, 30, 35, 40, 45, 50 nucleotides within said exon is used.

In a preferred embodiment, a molecule or an oligonucleotide of the invention which comprises a sequence that is complementary to a part of exon 45 of DMD pre-mRNA is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% and most preferably up to 100%. "A part of exon 45" preferably means a stretch of at least 21 nucleotides. In a most preferred embodiment, an oligonucleotide of the invention consists of a sequence that is complementary to part of exon 45 dystrophin pre-mRNA as defined herein. Alternatively, an oligonucleotide may comprise a sequence that is complementary to part of exon 45 dystrophin pre-mRNA as defined herein and additional flanking sequences. In a more preferred embodiment, the length of said complementary part of said oligonucleotide is of at least 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. Several types of flanking sequences may be used. Preferably, additional flanking sequences are used to modify the binding of a protein to said molecule or oligonucleotide, or to modify a thermodynamic property of the oligonucleotide, more preferably to modify target RNA binding affinity. In another preferred embodiment, additional flanking sequences are complementary to sequences of the DMD pre-mRNA which are not present in exon 45. Such flanking sequences are preferably complementary to sequences comprising or consisting of the splice site acceptor or donor consensus sequences of exon 45. In a preferred embodiment, such flanking sequences are complementary to sequences comprising or consisting of sequences of an intron of the DMD pre-mRNA which is adjacent to exon 45; i.e. intron 44 or 45.

A continuous stretch of at least 21, 25, 30, 35, 40, 45, 50 nucleotides within exon 45 is preferably selected from the sequence: 5'-CCAGGAUGGCAUUGGGCAGCGGCAA-ACUGUUGUCAGA ACAUUGAAUGCAACUGGG-GAAGAAAUAAUUCAGCAAUC-3' (SEQ ID NO 2).

It was found that a molecule that binds to a nucleotide sequence comprising or consisting of a continuous stretch of at least 21, 25, 30, 35, 40, 45, 50 nucleotides of SEQ ID NO. 2 results in highly efficient skipping of exon 45 in a cell provided with this molecule. Molecules that bind to a nucleotide sequence comprising a continuous stretch of less than 21 nucleotides of SEQ ID NO:2 were found to induce exon skipping in a less efficient way than the molecules of the invention. Therefore, in a preferred embodiment, a method is provided wherein a molecule binds to a continuous stretch of at least 21, 25, 30, 35 nucleotides within SEQ ID NO:2. Contrary to what was generally thought, the inventors surprisingly found that a higher specificity and efficiency of exon skipping may be reached using an oligonucleotides having a length of at least 21 nucleotides. None of the indicated sequences is derived from conserved parts of splice-junction sites. Therefore, said molecule is not likely to mediate differential splicing of other exons from the DMD pre-mRNA or exons from other genes.

In one embodiment, a molecule of the invention capable of interfering with the inclusion of exon 45 of the DMD pre-mRNA is a compound molecule that binds to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are for example disclosed in PCT/NL01/00697 and U.S. Pat. No. 6,875,736, which are herein enclosed by reference. Methods for designing RNA-binding Zinc-finger proteins that bind specific nucleotide sequences are disclosed by Friesen and Darby, Nature Structural Biology 5: 543-546 (1998) which is herein enclosed by reference.

In a further embodiment, a molecule of the invention capable of interfering with the inclusion of exon 45 of the DMD pre-mRNA comprises an antisense oligonucleotide that is complementary to and can base-pair with the coding strand of the pre-mRNA of the DMD gene. Said antisense oligonucleotide preferably contains a RNA residue, a DNA residue, and/or a nucleotide analogue or equivalent, as will be further detailed herein below.

A preferred molecule of the invention comprises a nucleotide-based or nucleotide or an antisense oligonucleotide sequence of between 21 and 50 nucleotides or bases, more preferred between 21 and 40 nucleotides, more preferred between 21 and 30 nucleotides, such as 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, 35 nucleotides, 36 nucleotides, 37 nucleotides, 38 nucleotides, 39 nucleotides, 40 nucleotides, 41 nucleotides, 42 nucleotides, 43 nucleotides, 44 nucleotides, 45 nucleotides, 46 nucleotides, 47 nucleotides, 48 nucleotides, 49 nucleotides or 50 nucleotides.

A most preferred molecule of the invention comprises a nucleotide-based sequence of 25 nucleotides.

In a preferred embodiment, a molecule of the invention binds to a continuous stretch of or is complementary to or is antisense to at least a continuous stretch of at least 21 nucleotides within the nucleotide sequence SEQ ID NO:2.

In a certain embodiment, the invention provides a molecule comprising or consisting of an antisense nucleotide sequence selected from the antisense nucleotide sequences as depicted in Table 1, except SEQ ID NO:68. A molecule of the invention that is antisense to the sequence of SEQ ID NO 2, which is present in exon 45 of the DMD gene preferably comprises or consists of the antisense nucleotide sequence of SEQ ID NO 3; SEQ ID NO 4, SEQ ID NO 5, SEQ ID NO 6, SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, SEQ ID NO 26, SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 51, SEQ ID NO 52, SEQ ID NO 53, SEQ ID NO 54, SEQ ID NO 55, SEQ ID NO 56, SEQ ID NO 57, SEQ ID NO 58, SEQ ID NO 59, SEQ ID NO 60, SEQ ID NO 61, SEQ ID NO 62, SEQ ID NO 63, SEQ ID NO 64, SEQ ID NO 65, SEQ ID NO 66 and/or SEQ ID NO:67.

In a more preferred embodiment, the invention provides a molecule comprising or consisting of the antisense nucleotide sequence of SEQ ID NO 3; SEQ ID NO 4, SEQ ID NO 5, SEQ ID NO 6, SEQ ID NO 7 and/or SEQ ID NO 8.

In a most preferred embodiment, the invention provides a molecule comprising or consisting of the antisense nucleotide sequence of SEQ ID NO 3. It was found that this molecule is very efficient in modulating splicing of exon 45 of the DMD pre-mRNA in a muscle cell.

A nucleotide sequence of a molecule of the invention may contain a RNA residue, a DNA residue, a nucleotide analogue or equivalent as will be further detailed herein below. In addition, a molecule of the invention may encompass a functional equivalent of a molecule of the invention as defined herein.

It is preferred that a molecule of the invention comprises a or at least one residue that is modified to increase nuclease resistance, and/or to increase the affinity of the antisense nucleotide for the target sequence. Therefore, in a preferred embodiment, an antisense nucleotide sequence comprises a or at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, a nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between a residue in a backbone does not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of at least one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, aryl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; aminoxy, methoxyethoxy; -dimethylaminooxyethoxy; and -dimethylaminoethoxyethoxy. The sugar moiety can be a pyranose or derivative thereof, or a deoxypyranose or derivative thereof, preferably a ribose or a derivative thereof, or deoxyribose or derivative thereof. Such preferred derivatized sugar moieties comprise Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred antisense oligonucleotide according to the invention comprises a 2'-O-alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

A most preferred antisense oligonucleotide according to the invention comprises a 2'-O-methyl phosphorothioate ribose.

A functional equivalent of a molecule of the invention may be defined as an oligonucleotide as defined herein wherein an activity of said functional equivalent is retained to at least some extent. Preferably, an activity of said functional equivalent is inducing exon 45 skipping and providing a functional dystrophin protein. Said activity of said functional equivalent is therefore preferably assessed by detection of exon 45 skipping and quantifying the amount of a functional dystrophin protein. A functional dystrophin is herein preferably defined as being a dystrophin able to bind actin and members of the DGC protein complex. The assessment of said activity of an oligonucleotide is preferably done by RT-PCR or by immunofluorescence or Western blot analysis. Said activity is preferably retained to at least some extent when it represents at least 50%, or at least 60%, or at least 70% or at least 80% or at least 90% or at least 95% or more of corresponding activity of said oligonucleotide the functional equivalent derives from. Throughout this application, when the word oligonucleotide is used it may be replaced by a functional equivalent thereof as defined herein.

It will also be understood by a skilled person that distinct antisense oligonucleotides can be combined for efficiently skipping of exon 45 of the human DMD pre-mRNA. In a preferred embodiment, a combination of at least two antisense oligonucleotides are used in a method of the invention, such as two distinct antisense oligonucleotides, three distinct antisense oligonucleotides, four distinct antisense oligonucleotides, or five distinct antisense oligonucleotides or even more. It is also encompassed by the present invention to combine several oligonucleotides or molecules as depicted in table 1 except SEQ ID NO:68.

An antisense oligonucleotide can be linked to a moiety that enhances uptake of the antisense oligonucleotide in cells, preferably myogenic cells or muscle cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

A preferred antisense oligonucleotide comprises a peptide-linked PMO.

A preferred antisense oligonucleotide comprising one or more nucleotide analogs or equivalents of the invention modulates splicing in one or more muscle cells, including heart muscle cells, upon systemic delivery. In this respect, systemic delivery of an antisense oligonucleotide comprising a specific nucleotide analog or equivalent might result in targeting a subset of muscle cells, while an antisense oligonucleotide comprising a distinct nucleotide analog or equivalent might result in targeting of a different subset of muscle cells. Therefore, in one embodiment it is preferred to use a combination of antisense oligonucleotides comprising different nucleotide analogs or equivalents for modulating skipping of exon 45 of the human DMD pre-mRNA.

A cell can be provided with a molecule capable of interfering with essential sequences that result in highly efficient skipping of exon 45 of the human DMD pre-mRNA by plasmid-derived antisense oligonucleotide expression or viral expression provided by viral-based vector. Such a viral-based vector comprises an expression cassette that drives expression of an antisense molecule as defined herein. Preferred virus-based vectors include adenovirus- or adeno-associated virus-based vectors. Expression is preferably driven by a polymerase III promoter, such as a U1, a U6, or a U7 RNA promoter. A muscle or myogenic cell can be provided with a plasmid for antisense oligonucleotide expression by providing the plasmid in an aqueous solution. Alternatively, a plasmid can be provided by transfection using known transfection agentia such as, for example, LipofectAMINE™ 2000 (Invitrogen) or polyethyleneimine (PEI; ExGen500 (MBI Fermentas)), or derivatives thereof.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of exon 45 of the DMD pre-mRNA.

A preferred AAV-based vector comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of one or more antisense sequences of the invention for inducing skipping of exon 45 of the human DMD pre-mRNA.

Pharmaceutical Composition

If required, a molecule or a vector expressing an antisense oligonucleotide of the invention can be incorporated into a pharmaceutically active mixture or composition by adding a pharmaceutically acceptable carrier.

Therefore, in a further aspect, the invention provides a composition, preferably a pharmaceutical composition comprising a molecule comprising an antisense oligonucleotide according to the invention, and/or a viral-based vector expressing the antisense sequence(s) according to the invention and a pharmaceutically acceptable carrier.

A preferred pharmaceutical composition comprises a molecule as defined herein and/or a vector as defined herein, and a pharmaceutical acceptable carrier or excipient, optionally combined with a molecule and/or a vector which is able to modulate skipping of exon 7, 44, 46, 51, 53, 59, 67 of the DMD pre-mRNA.

Preferred excipients include excipients capable of forming complexes, vesicles and/or liposomes that deliver such a molecule as defined herein, preferably an oligonucleotide complexed or trapped in a vesicle or liposome through a cell membrane. Many of these excipients are known in the art. Suitable excipients comprise polyethylenimine and derivatives, or similar cationic polymers, including polypropyleneimine or polyethylenimine copolymers (PECs) and derivatives, synthetic amphiphils, Lipofectin™, DOTAP and/or viral capsid proteins that are capable of self assembly into particles that can deliver such molecule, preferably an oligonucleotide as defined herein to a cell, preferably a muscle cell. Such excipients have been shown to efficiently deliver (oligonucleotide such as antisense) nucleic acids to a wide variety of cultured cells, including muscle cells. We obtained very good results using polyethylenimine (PEI, ExGen500, MBI Fermentas) as shown in the example. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver a molecule or a compound as defined herein, preferably an oligonucleotide across cell membranes into cells.

In addition to these common nanoparticle materials, the cationic peptide protamine offers an alternative approach to formulate a compound as defined herein, preferably an oligonucleotide as colloids. This colloidal nanoparticle system can form so called proticles, which can be prepared by a simple self-assembly process to package and mediate intracellular release of a compound as defined herein, preferably an oligonucleotide. The skilled person may select and adapt any of the above or other commercially available alternative excipients and delivery systems to package and deliver a compound as defined herein, preferably an oligonucleotide for use in the current invention to deliver said compound for the treatment of Duchenne Muscular Dystrophy in humans.

In addition, a compound as defined herein, preferably an oligonucleotide could be covalently or non-covalently linked to a targeting ligand specifically designed to facilitate the uptake in to the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an a compound as defined herein, preferably an oligonucleotide from vesicles, e.g. endosomes or lysosomes.

Therefore, in a preferred embodiment, a compound as defined herein, preferably an oligonucleotide are formulated in a medicament which is provided with at least an excipient and/or a targeting ligand for delivery and/or a delivery device of said compound to a cell and/or enhancing its intracellular delivery. Accordingly, the invention also encompasses a pharmaceutically acceptable composition comprising a compound as defined herein, preferably an oligonucleotide and further comprising at least one excipient and/or a targeting ligand for delivery and/or a delivery device of said compound to a cell and/or enhancing its intracellular delivery.

It is to be understood that a molecule or compound or oligonucleotide may not be formulated in one single composition or preparation. Depending on their identity, the skilled person will know which type of formulation is the most appropriate for each compound.

In a preferred embodiment, an in vitro concentration of a molecule or an oligonucleotide as defined herein, which is ranged between 0.1 nM and 1 µM is used. More preferably, the concentration used is ranged between 0.3 to 400 nM, even more preferably between 1 to 200 nM. molecule or an oligonucleotide as defined herein may be used at a dose which is ranged between 0.1 and 20 mg/kg, preferably 0.5 and 10 mg/kg. If several molecules or oligonucleotides are used, these concentrations may refer to the total concentration of oligonucleotides or the concentration of each oligonucleotide added. The ranges of concentration of oligonucleotide(s) as given above are preferred concentrations for in vitro or ex vivo uses. The skilled person will understand that depending on the oligonucleotide(s) used, the target cell to be treated, the gene target and its expression levels, the medium used and the transfection and incubation conditions, the concentration of oligonucleotide(s) used may further vary and may need to be optimised any further.

More preferably, a compound preferably an oligonucleotide and an adjunct compound to be used in the invention to prevent, treat DMD are synthetically produced and administered directly to a cell, a tissue, an organ and/or patients in formulated form in a pharmaceutically acceptable composition or preparation. The delivery of a pharmaceutical composition to the subject is preferably carried out by one or more parenteral injections, e.g. intravenous and/or subcutaneous and/or intramuscular and/or intrathecal and/or intraventricular administrations, preferably injections, at one or at multiple sites in the human body.

Use

In yet a further aspect, the invention provides the use of an antisense oligonucleotide or molecule according to the invention, and/or a viral-based vector that expresses one or more antisense sequences according to the invention and/or a pharmaceutical composition, for inducing and/or promoting splicing of the DMD pre-mRNA. The splicing is preferably modulated in a human myogenic cell or a muscle cell in vitro. More preferred is that splicing is modulated in human a myogenic cell or muscle cell in vivo.

Accordingly, the invention further relates to the use of the molecule as defined herein and/or the vector as defined herein and/or the pharmaceutical composition as defined herein for inducing and/or promoting splicing of the DMD pre-mRNA or for the preparation of a medicament for the treatment of a DMD patient.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a molecule or a viral-based vector or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each embodiment as identified herein may be combined together unless otherwise indicated. All patent and literature references cited in the present specification are hereby incorporated by reference in their entirety.

The following examples are offered for illustrative purposes only, and are not intended to limit the scope of the present invention in any way.

LEGENDS TO THE FIGURE

FIG. 1. In human control myotubes, a series of AONs (PS220 to PS225; SEQ ID NO: 3 to 8), all binding to a continuous stretch of at least 21 nucleotides within a specific sequence of exon 45 (i.e. SEQ ID NO:2), were tested at two different concentrations (200 and 500 nM). All six AONs were effective in inducing specific exon 45 skipping, as confirmed by sequence analysis (not shown). PS220 (SEQ ID NO:3) however, reproducibly induced highest levels of exon 45 skipping (see FIG. 2). (NT: non-treated cells, M: size marker).

Figure 2:
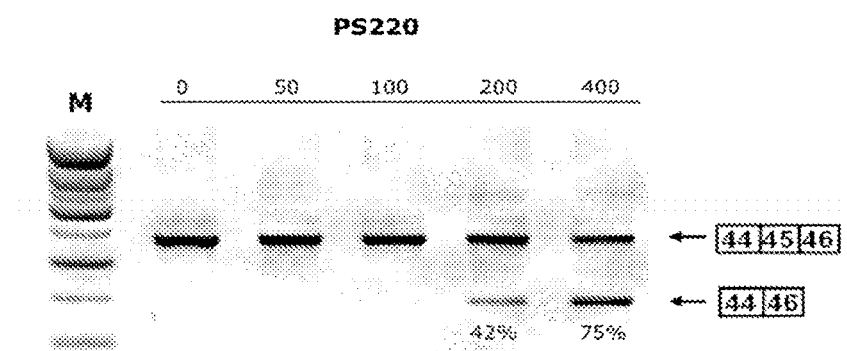

FIG. 2. In human control myotubes, 25-mer PS220 (SEQ ID NO: 3) was tested at increasing concentration. Levels of exon 45 skipping of up to 75% (at 400 nM) were observed reproducibly, as assessed by Agilent LabChip Analysis.

Figure 3:
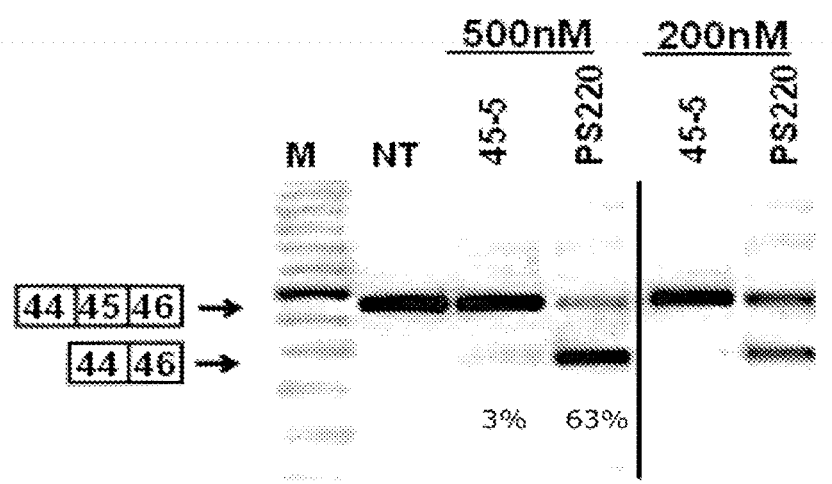

FIG. 3. In human control myotubes, the efficiencies of a "short" 17-mer AON45-5 (SEQ ID NO:68) and its overlapping "long" 25-mer counterpart PS220 were directly compared at 200 nM and 500 nM. PS220 was markedly more efficient at both concentrations: 63% when compared to 3% obtained with 45-5. (NT: non-treated cells, M: size marker).

EXAMPLES

Examples 1 and 2

Materials and Methods

AON design was based on (partly) overlapping open secondary structures of the target exon RNA as predicted by the m-fold program (Zuker, M. (2003) Mfold web server for nucleic acid folding and hybridization prediction. *Nucleic Acids Res.*, 31, 3406-3415), and on (partly) overlapping putative SR-protein binding sites as predicted by numerous software programs such as ESEfinder (Cartegni, L. et al. (2003) ESEfinder: A web resource to identify exonic splicing enhancers. *Nucleic Acids Res,* 31, 3568-71; Smith, P. J. et al. (2006) An increased specificity score matrix for the prediction of SF2/ASF-specific exonic splicing enhancers. *Hum. Mol. Genet.,* 15, 2490-2508) that predicts binding sites for the four most abundant SR proteins (SF2/ASF, SC35, SRp40 and SRp55). AONs were synthesized by Prosensa Therapeutics B.V. (Leiden, Netherlands), and contain 2'-O-methyl RNA and full-length phosphorothioate (PS) backbones.

Tissue Culturing, Transfection and RT-PCR Analysis

Myotube cultures derived from a healthy individual ("human control") were obtained as described previously (Aartsma-Rus et al. Hum Mol Genet 2003; 12(8): 907-14). For the screening of AONs, myotube cultures were transfected with 0 to 500 nM of each AON. The transfection reagent polyethylenimine (PEI, ExGen500 MBI Fermentas) was used according to manufacturer's instructions, with 2 µl PEI per µg AON. Exon skipping efficiencies were determined by nested RT-PCR analysis using primers in the exons flanking exon 45. PCR fragments were isolated from agarose gels for sequence verification. For quantification, the PCR products were analyzed using the Agilent DNA 1000 LabChip Kit and the Agilent 2100 bioanalyzer (Agilent Technologies, USA).

Results

A series of AONs targeting sequences within SEQ ID NO:2 within exon 45 were designed and tested in normal myotube cultures, by transfection and subsequent RT-PCR and sequence analysis of isolated RNA. PS220 (SEQ ID NO: 3) reproducibly induced highest levels of exon 45 skipping, when compared to PS221-PS225 (FIG. 1). High levels of exon 45 skipping of up to 75% were already obtained at 400 nM PS220 (FIG. 2). In a direct comparison, PS220 (a 25-mer) was reproducibly more efficient in inducing exon 45 skipping than its shorter 17-mer counterpart AON 45-5 (SEQ ID NO: 68; previously published as h45AON5 (Aartsma-Rus et al. Am J Hum Genet 2004; 74: 83-92)), at both AON concentrations of 200 nM and 500 nM and with 63% versus 3% respectively at 500 nM (FIG. 3). This result is probably due to the fact that the extended length of PS220, in fact completely overlapping AON 45-5, increases the free energy of the AON-target complex such that the efficiency of inducing exon 45 skipping is also increased.

TABLE 1

AONs in exon 45

| | |
|---|---|
| SEQ ID NO 3 (PS220) | UUUGCCGCUGCCCAAUGCCAUCCUG |
| SEQ ID NO 4 (PS221) | AUUCAAUGUUCUGACAACAGUUUGC |
| SEQ ID NO 5 (PS222) | CCAGUUGCAUUCAAUGUUCUGACAA |
| SEQ ID NO 6 (PS223) | CAGUUGCAUUCAAUGUUCUGAC |
| SEQ ID NO 7 (PS224) | AGUUGCAUUCAAUGUUCUGA |
| SEQ ID NO 8 (PS225) | GAUUGCUGAAUUAUUUCUUCC |
| SEQ ID NO 9 | GAUUGCUGAAUUAUUUCUUCCCCAG |
| SEQ ID NO 10 | AUUGCUGAAUUAUUUCUUCCCCAGU |
| SEQ ID NO 11 | UUGCUGAAUUAUUUCUUCCCCAGUU |
| SEQ ID NO 12 | UGCUGAAUUAUUUCUUCCCCAGUUG |
| SEQ ID NO 13 | GCUGAAUUAUUUCUUCCCCAGUUGC |
| SEQ ID NO 14 | CUGAAUUAUUUCUUCCCCAGUUGCA |
| SEQ ID NO 15 | UGAAUUAUUUCUUCCCCAGUUGCAU |
| SEQ ID NO 16 | GAAUUAUUUCUUCCCCAGUUGCAUU |
| SEQ ID NO 17 | AAUUAUUUCUUCCCCAGUUGCAUUC |
| SEQ ID NO 18 | AUUAUUUCUUCCCCAGUUGCAUUCA |
| SEQ ID NO 19 | UUAUUUCUUCCCCAGUUGCAUUCAA |
| SEQ ID NO 20 | UAUUUCUUCCCCAGUUGCAUUCAAU |
| SEQ ID NO 21 | AUUUCUUCCCCAGUUGCAUUCAAUG |
| SEQ ID NO 22 | UUUCUUCCCCAGUUGCAUUCAAUGU |
| SEQ ID NO 23 | UUCUUCCCCAGUUGCAUUCAAUGUU |
| SEQ ID NO 24 | UCUUCCCCAGUUGCAUUCAAUGUUC |
| SEQ ID NO 25 | CUUCCCCAGUUGCAUUCAAUGUUCU |
| SEQ ID NO 26 | UUCCCCAGUUGCAUUCAAUGUUCUG |
| SEQ ID NO 27 | UCCCCAGUUGCAUUCAAUGUUCUGA |
| SEQ ID NO 28 | CCCCAGUUGCAUUCAAUGUUCUGAC |
| SEQ ID NO 29 | CCCAGUUGCAUUCAAUGUUCUGACA |
| SEQ ID NO 30 | CCAGUUGCAUUCAAUGUUCUGACAA |
| SEQ ID NO 31 | CAGUUGCAUUCAAUGUUCUGACAAC |
| SEQ ID NO 32 | AGUUGCAUUCAAUGUUCUGACAACA |
| SEQ ID NO 33 | UCCUGUAGAAUACUGGCAUC |
| SEQ ID NO 34 | UGCAGACCUCCUGCCACCGCAGAUUCA |
| SEQ ID NO 35 | UUGCAGACCUCCUGCCACCGCAGAUUCAGGCUUC |
| SEQ ID NO 36 | GUUGCAUUCAAUGUUCUGACAACAG |
| SEQ ID NO 37 | UUGCAUUCAAUGUUCUGACAACAGU |
| SEQ ID NO 38 | UGCAUUCAAUGUUCUGACAACAGUU |
| SEQ ID NO 39 | GCAUUCAAUGUUCUGACAACAGUUU |
| SEQ ID NO 40 | CAUUCAAUGUUCUGACAACAGUUUG |
| SEQ ID NO 41 | AUUCAAUGUUCUGACAACAGUUUGC |
| SEQ ID NO 42 | UCAAUGUUCUGACAACAGUUUGCCG |
| SEQ ID NO 43 | CAAUGUUCUGACAACAGUUUGCCGC |
| SEQ ID NO 44 | AAUGUUCUGACAACAGUUUGCCGCU |
| SEQ ID NO 45 | AUGUUCUGACAACAGUUUGCCGCUG |
| SEQ ID NO 46 | UGUUCUGACAACAGUUUGCCGCUGC |
| SEQ ID NO 47 | GUUCUGACAACAGUUUGCCGCUGCC |
| SEQ ID NO 48 | UUCUGACAACAGUUUGCCGCUGCCC |
| SEQ ID NO 49 | UCUGACAACAGUUUGCCGCUGCCCA |
| SEQ ID NO 50 | CUGACAACAGUUUGCCGCUGCCCAA |
| SEQ ID NO 51 | UGACAACAGUUUGCCGCUGCCCAAU |
| SEQ ID NO 52 | GACAACAGUUUGCCGCUGCCCAAUG |
| SEQ ID NO 53 | ACAACAGUUUGCCGCUGCCCAAUGC |
| SEQ ID NO 54 | CAACAGUUUGCCGCUGCCCAAUGCC |
| SEQ ID NO 55 | AACAGUUUGCCGCUGCCCAAUGCCA |
| SEQ ID NO 56 | ACAGUUUGCCGCUGCCCAAUGCCAU |
| SEQ ID NO 57 | CAGUUUGCCGCUGCCCAAUGCCAUC |
| SEQ ID NO 58 | AGUUUGCCGCUGCCCAAUGCCAUCC |
| SEQ ID NO 59 | GUUUGCCGCUGCCCAAUGCCAUCCU |
| SEQ ID NO 60 | UUUGCCGCUGCCCAAUGCCAUCCUG |
| SEQ ID NO 61 | UUGCCGCUGCCCAAUGCCAUCCUGG |
| SEQ ID NO 62 | UGCCGCUGCCCAAUGCCAUCCUGGA |
| SEQ ID NO 63 | GCCGCUGCCCAAUGCCAUCCUGGAG |

TABLE 1-continued

AONs in exon 45

| | |
|---|---|
| SEQ ID NO 64 | CCGCUGCCCAAUGCCAUCCUGGAGUU |
| SEQ ID NO 65 | CGCUGCCCAAUGCCAUCCUGGAGUU |
| SEQ ID NO 66 | UGUUUUGAGGAUUGCUGAA |
| SEQ ID NO 67 | UGUUCUGACAACAGUUUGCCGCUGCCCAAUGCCAUCCUGG |
| SEQ ID NO 68 (45-5) | GCCCAAUGCCAUCCUGG |

TABLE 2

AONs in exons 51, 53, 7, 44, 46, 59, and 67

DMD Gene Exon 51

| | |
|---|---|
| SEQ ID NO 69 | AGAGCAGGUACCUCCAACAUCAAGG |
| SEQ ID NO 70 | GAGCAGGUACCUCCAACAUCAAGGA |
| SEQ ID NO 71 | AGCAGGUACCUCCAACAUCAAGGAA |
| SEQ ID NO 72 | GCAGGUACCUCCAACAUCAAGGAAG |
| SEQ ID NO 73 | CAGGUACCUCCAACAUCAAGGAAGA |
| SEQ ID NO 74 | AGGUACCUCCAACAUCAAGGAAGAU |
| SEQ ID NO 75 | GGUACCUCCAACAUCAAGGAAGAUG |
| SEQ ID NO 76 | GUACCUCCAACAUCAAGGAAGAUGG |
| SEQ ID NO 77 | UACCUCCAACAUCAAGGAAGAUGGC |
| SEQ ID NO 78 | ACCUCCAACAUCAAGGAAGAUGGCA |
| SEQ ID NO 79 | CCUCCAACAUCAAGGAAGAUGGCAU |
| SEQ ID NO 80 | CUCCAACAUCAAGGAAGAUGGCAUU |
| SEQ ID NO 81 | CUCCAACAUCAAGGAAGAUGGCAUUUCUAG |
| SEQ ID NO 82 | UCCAACAUCAAGGAAGAUGGCAUUU |
| SEQ ID NO 83 | CCAACAUCAAGGAAGAUGGCAUUUC |
| SEQ ID NO 84 | CAACAUCAAGGAAGAUGGCAUUUCU |
| SEQ ID NO 85 | AACAUCAAGGAAGAUGGCAUUUCUA |
| SEQ ID NO 86 | ACAUCAAGGAAGAUGGCAUUUCUAG |
| SEQ ID NO 87 | ACAUCAAGGAAGAUGGCAUUUCUAGUUUGG |
| SEQ ID NO 88 | ACAUCAAGGAAGAUGGCAUUUCUAG |
| SEQ ID NO 89 | CAUCAAGGAAGAUGGCAUUUCUAGU |
| SEQ ID NO 90 | AUCAAGGAAGAUGGCAUUUCUAGUU |
| SEQ ID NO 91 | UCAAGGAAGAUGGCAUUUCUAGUUU |
| SEQ ID NO 92 | UCAAGGAAGAUGGCAUUUCU |
| SEQ ID NO 93 | CAAGGAAGAUGGCAUUUCUAGUUUG |
| SEQ ID NO 94 | AAGGAAGAUGGCAUUUCUAGUUUGG |
| SEQ ID NO 95 | AGGAAGAUGGCAUUUCUAGUUUGGA |
| SEQ ID NO 96 | GGAAGAUGGCAUUUCUAGUUUGGAG |
| SEQ ID NO 97 | GAAGAUGGCAUUUCUAGUUUGGAGA |
| SEQ ID NO 98 | AAGAUGGCAUUUCUAGUUUGGAGAU |
| SEQ ID NO 99 | AGAUGGCAUUUCUAGUUUGGAGAUG |
| SEQ ID NO 100 | GAUGGCAUUUCUAGUUUGGAGAUGG |
| SEQ ID NO 101 | AUGGCAUUUCUAGUUUGGAGAUGGC |
| SEQ ID NO 102 | UGGCAUUUCUAGUUUGGAGAUGGCA |
| SEQ ID NO 103 | GGCAUUUCUAGUUUGGAGAUGGCAG |
| SEQ ID NO 104 | GCAUUUCUAGUUUGGAGAUGGCAGU |
| SEQ ID NO 105 | CAUUUCUAGUUUGGAGAUGGCAGUU |
| SEQ ID NO 106 | AUUUCUAGUUUGGAGAUGGCAGUUU |
| SEQ ID NO 107 | UUUCUAGUUUGGAGAUGGCAGUUUC |
| SEQ ID NO 108 | UUCUAGUUUGGAGAUGGCAGUUUCC |

DMD Gene Exon 53

| | |
|---|---|
| SEQ ID NO 109 | CCAUUGUGUUGAAUCCUUUAACAUU |
| SEQ ID NO 110 | CCAUUGUGUUGAAUCCUUUAAC |
| SEQ ID NO 111 | AUUGUGUUGAAUCCUUUAAC |
| SEQ ID NO 112 | CCUGUCCUAAGACCUGCUCA |
| SEQ ID NO 113 | CUUUGGAUUGCAUCUACUGUAUAG |
| SEQ ID NO 114 | CAUUCAACUGUUGCCUCCGGUUCUG |
| SEQ ID NO 115 | CUGUUGCCUCCGGUUCUGAAGGUG |
| SEQ ID NO 116 | CAUUCAACUGUUGCCUCCGGUUCUGAAGGUG |
| SEQ ID NO 117 | CUGAAGGUGUUCUUGUACUUCAUCC |
| SEQ ID NO 118 | UGUAUAGGGACCCUCCUUCCAUGACUC |
| SEQ ID NO 119 | AUCCCACUGAUUCUGAAUUC |

TABLE 2-continued

AONs in exons 51, 53, 7, 44, 46, 59, and 67

| | |
|---|---|
| SEQ ID NO 120 | UUGGCUCUGGCCUGUCCUAAGA |
| SEQ ID NO 121 | AAGACCUGCUCAGCUUCUUCCUUAGCUUCCAGCCA |

DMD Gene Exon 7

| | |
|---|---|
| SEQ ID NO 122 | UGCAUGUUCCAGUCGUUGUGUGG |
| SEQ ID NO 123 | CACUAUUCCAGUCAAAUAGGUCUGG |
| SEQ ID NO 124 | AUUUACCAACCUUCAGGAUCGAGUA |
| SEQ ID NO 125 | GGCCUAAAACACAUACACAUA |

DMD Gene Exon 44

| | |
|---|---|
| SEQ ID NO 126 | UCAGCUUCUGUUAGCCACUG |
| SEQ ID NO 127 | UUCAGCUUCUGUUAGCCACU |
| SEQ ID NO 128 | UUCAGCUUCUGUUAGCCACUG |
| SEQ ID NO 129 | UCAGCUUCUGUUAGCCACUGA |
| SEQ ID NO 130 | UUCAGCUUCUGUUAGCCACUGA |
| SEQ ID NO 131 | UCAGCUUCUGUUAGCCACUGA |
| SEQ ID NO 132 | UUCAGCUUCUGUUAGCCACUGA |
| SEQ ID NO 133 | UCAGCUUCUGUUAGCCACUGAU |
| SEQ ID NO 134 | UUCAGCUUCUGUUAGCCACUGAU |
| SEQ ID NO 135 | UCAGCUUCUGUUAGCCACUGAUU |
| SEQ ID NO 136 | UUCAGCUUCUGUUAGCCACUGAUU |
| SEQ ID NO 137 | UCAGCUUCUGUUAGCCACUGAUUA |
| SEQ ID NO 138 | UUCAGCUUCUGUUAGCCACUGAUA |
| SEQ ID NO 139 | UCAGCUUCUGUUAGCCACUGAUUAA |
| SEQ ID NO 140 | UUCAGCUUCUGUUAGCCACUGAUUAA |
| SEQ ID NO 141 | UCAGCUUCUGUUAGCCACUGAUUAAA |
| SEQ ID NO 142 | UUCAGCUUCUGUUAGCCACUGAUUAAA |
| SEQ ID NO 143 | CAGCUUCUGUUAGCCACCG |
| SEQ ID NO 144 | CAGCUUCUGUUAGCCACCGAU |
| SEQ ID NO 145 | AGCUCCUGUCAGCCACUGACU |
| SEQ ID NO 146 | CAGCUUCUGUUAGCCACUGAUU |
| SEQ ID NO 147 | AGCUCCUGUUAGCCACUGACUA |
| SEQ ID NO 148 | CAGCUUCUGUUAGCCACCGAUUA |
| SEQ ID NO 149 | AGCUCCUGUUAGCCACUGACUAA |
| SEQ ID NO 150 | CAGCUUCUGUUAGCCACCGAUUAA |
| SEQ ID NO 151 | AGCUUCUGUCAGCCACUGAUUAAA |
| SEQ ID NO 152 | CAGCUUCUGUUAGCCACCGAUUAAA |
| SEQ ID NO 153 | AGCUUCUGUCAGCCACUGAUUAAAA |
| SEQ ID NO 154 | AGCUUCUGUUAGCCACUGAU |
| SEQ ID NO 155 | GCUUCUGUUAGCCACUGAUU |
| SEQ ID NO 156 | AGCUUCUGUCAGCCACUGAUU |
| SEQ ID NO 157 | GCUUCUGUUAGCCACUGAUUA |
| SEQ ID NO 158 | AGCUUCUGUCAGCCACUGAUUA |
| SEQ ID NO 159 | GCUUCUGUUAGCCACUGAUUAA |
| SEQ ID NO 160 | AGCUUCUGUCAGCCACUGAUUAA |
| SEQ ID NO 161 | GCUUCUGUUAGCCACUGAUUAAA |
| SEQ ID NO 162 | AGCUUCUGUCAGCCACUGAUUAAA |
| SEQ ID NO 163 | GCUUCUGUUAGCCACUGAUUAAAA |
| SEQ ID NO 164 | CCAUUUGUACUUAGCAUGUUCCA |
| SEQ ID NO 165 | AGAUACCAUCUGUAUUCAGC |
| SEQ ID NO 166 | GCCAUUUCUCAACGAUCU |
| SEQ ID NO 167 | GCCAUUUCUCAACAGAUCUGUCA |
| SEQ ID NO 168 | AUUCUCAGGAAUUUGUGUCUUUC |
| SEQ ID NO 169 | UCUCAGGAAUUUGUGUCUUUC |
| SEQ ID NO 170 | GUUCAGCUUCUGUUAGCC |
| SEQ ID NO 171 | CUGAUUAAAUAUCUUUAUAUC |
| SEQ ID NO 172 | GCCGCCAUUUCUCAACAG |
| SEQ ID NO 173 | GUAUUAGCAUGUUCCCA |
| SEQ ID NO 174 | CAGGAAUUUGUGUCUUCC |

DMD Gene Exon 46

| | |
|---|---|
| SEQ ID NO 175 | GCUUUUCUUUUAGUUGCUGCUCUUU |
| SEQ ID NO 176 | CUUUUCUUUUAGUUGCUGCUCUUUU |
| SEQ ID NO 177 | UUUUCUUUUAGUUGCUGCUCUUUUC |
| SEQ ID NO 178 | UUUCUUUUAGUUGCUGCUCUUUUCC |
| SEQ ID NO 179 | UUCUUUUAGUUGCUGCUCUUUUCCA |
| SEQ ID NO 180 | UCUUUUAGUUGCUGCUCUUUUCCAG |
| SEQ ID NO 181 | CUUUUAGUUGCUGCUCUUUUCCAGG |
| SEQ ID NO 182 | UUUUAGUUGCUGCUCUUUUCCAGGU |
| SEQ ID NO 183 | UUUAGUUGCUGCUCUUUUCCAGGUU |
| SEQ ID NO 184 | UUAGUUGCUGCUCUUUUCCAGGUUC |
| SEQ ID NO 185 | UAGUUGCUGCUCUUUUCCAGGUUCA |
| SEQ ID NO 186 | AGUUGCUGCUCUUUUCCAGGUUCAA |
| SEQ ID NO 187 | GUUGCUGCUCUUUUCCAGGUUCAAG |

TABLE 2-continued

AONs in exons 51, 53, 7, 44, 46, 59, and 67

| | |
|---|---|
| SEQ ID NO 188 | UUGCUGCUCUUUUCCAGGUUCAAGU |
| SEQ ID NO 189 | UGCUGCUCUUUUCCAGGUUCAAGUG |
| SEQ ID NO 190 | GCUGCUCUUUUCCAGGUUCAAGUGG |
| SEQ ID NO 191 | CUGCUCUUUUCCAGGUUCAAGUGGG |
| SEQ ID NO 192 | UGCUCUUUUCCAGGUUCAAGUGGGA |
| SEQ ID NO 193 | GCUCUUUUCCAGGUUCAAGUGGGAC |
| SEQ ID NO 194 | CUCUUUUCCAGGUUCAAGUGGGAUA |
| SEQ ID NO 195 | UCUUUUCCAGGUUCAAGUGGGAUAC |
| SEQ ID NO 196 | CUUUUCCAGGUUCAAGUGGGAUACU |
| SEQ ID NO 197 | UUUUCCAGGUUCAAGUGGGAUACUA |
| SEQ ID NO 198 | UUUCCAGGUUCAAGUGGGAUACUAG |
| SEQ ID NO 199 | UUCCAGGUUCAAGUGGGAUACUAGC |
| SEQ ID NO 200 | UCCAGGUUCAAGUGGGAUACUAGCA |
| SEQ ID NO 201 | CCAGGUUCAAGUGGGAUACUAGCAA |
| SEQ ID NO 202 | CAGGUUCAAGUGGGAUACUAGCAAU |
| SEQ ID NO 203 | AGGUUCAAGUGGGAUACUAGCAAUG |
| SEQ ID NO 204 | GGUUCAAGUGGGAUACUAGCAAUGU |
| SEQ ID NO 205 | GUUCAAGUGGGAUACUAGCAAUGUU |
| SEQ ID NO 206 | UUCAAGUGGGAUACUAGCAAUGUUA |
| SEQ ID NO 207 | UCAAGUGGGAUACUAGCAAUGUUAU |
| SEQ ID NO 208 | CAAGUGGGAUACUAGCAAUGUUAUC |
| SEQ ID NO 209 | AAGUGGGAUACUAGCAAUGUUAUCU |
| SEQ ID NO 210 | AGUGGGAUACUAGCAAUGUUAUCUG |
| SEQ ID NO 211 | GUGGGAUACUAGCAAUGUUAUCUGC |
| SEQ ID NO 212 | UGGGAUACUAGCAAUGUUAUCUGCU |
| SEQ ID NO 213 | GGGAUACUAGCAAUGUUAUCUGCUU |
| SEQ ID NO 214 | GGAUACUAGCAAUGUUAUCUGCUUC |
| SEQ ID NO 215 | GAUACUAGCAAUGUUAUCUGCUUCC |
| SEQ ID NO 216 | AUACUAGCAAUGUUAUCUGCUUCCU |
| SEQ ID NO 217 | UACUAGCAAUGUUAUCUGCUUCCUC |
| SEQ ID NO 218 | ACUAGCAAUGUUAUCUGCUUCCUCC |
| SEQ ID NO 219 | CUAGCAAUGUUAUCUGCUUCCUCCA |
| SEQ ID NO 220 | UAGCAAUGUUAUCUGCUUCCUCCAA |
| SEQ ID NO 221 | AGCAAUGUUAUCUGCUUCCUCCAAC |
| SEQ ID NO 222 | GCAAUGUUAUCUGCUUCCUCCAACC |
| SEQ ID NO 223 | CAAUGUUAUCUGCUUCCUCCAACCA |
| SEQ ID NO 224 | AAUGUUAUCUGCUUCCUCCAACCAU |
| SEQ ID NO 225 | AUGUUAUCUGCUUCCUCCAACCAUA |
| SEQ ID NO 226 | UGUUAUCUGCUUCCUCCAACCAUAA |
| SEQ ID NO 227 | GUUAUCUGCUUCCUCCAACCAUAAA |
| SEQ ID NO 228 | GCUGCUCUUUUCCAGGUUC |
| SEQ ID NO 229 | UCUUUUCCAGGUUCAAGUGG |
| SEQ ID NO 230 | AGGUUCAAGUGGGAUACUA |

DMD Gene Exon 59

| | |
|---|---|
| SEQ ID NO 231 | CAAUUUUUCCCACUCAGUAUU |
| SEQ ID NO 232 | UUGAAGUUCCUGGAGUCUU |
| SEQ ID NO 233 | UCCUCAGGAGGCAGCUCUAAAU |

DMD Gene Exon 67

| | |
|---|---|
| SEQ ID NO 234 | GCGCUGGUCACAAAAUCCUGUUGAAC |
| SEQ ID NO 235 | CACUUGCUUGAAAAGGUCUACAAAGGA |
| SEQ ID NO 236 | GGUGAAUAACUUACAAAUUUGGAAGC |

---

The invention claimed is:

1. A molecule that binds to a continuous stretch of at least 21 nucleotides within exon 45 of DMD pre-mRNA, wherein the molecule comprises or consists of a 2'-O-alkyl phosphorothioate antisense oligonucleotide sequence selected from SEQ ID NOS: 4, 5, 6 and 8.

2. The molecule according to claim 1, whereby said molecule binds to a continuous stretch of at least 25 nucleotides within said exon.

3. The molecule according to claim 1, whereby said molecule comprises an antisense oligonucleotide of between 21 and 30 bases.

4. The molecule according to claim 1, whereby said molecule comprises an antisense oligonucleotide of 25 bases.

5. The molecule according to claim 1, whereby said molecule binds to a continuous stretch of at least 21 nucleotides within the following nucleotide sequence:

(SEQ ID NO: 2)
5-CCAGGAUGGCAUUGGGCAGCGGCAAACUGUUGUCAGAACAUUGAAUGC

AACUGGGGAAGAAAUAAUUCAGCAAUC.

6. The molecule according to claim 1, comprising a 2'-O-methyl phosphorothioate ribose.

7. A viral-based vector, comprising an expression cassette that drives expression of the molecule as defined in claim 1.

8. A pharmaceutical composition comprising the molecule as defined in claim 1, a pharmaceutically acceptable carrier, and optionally a molecule having a base sequence selected from the base sequence of SEQ ID NOS: 69-80, 82-85, 89-91, 93-113, 121, 131, 132, 153, 156, 158, 160, 162, 163, 175, 177, 178, 179, 180, 182-200, 202-205, 207-220, 223-229, 235 and 236 which is able to induce or promote skipping of exon 7, 44, 46, 51, 53, 59, or 67 of the DMD pre-mRNA of a patient.

9. A method for inducing or promoting skipping of exon 45 of DMD pre-mRNA in a patient, the method comprising providing said patient with the molecule of claim 1.

10. The method according to claim 9, wherein the patient is provided with a functional dystrophin protein and/or wherein the production of an aberrant dystrophin protein in said patient is decreased, wherein the level of said functional dystrophin is assessed by comparison to the level of said dystrophin in said patient at the onset of the method.

* * * * *